US008222239B2

(12) United States Patent
Whiteford

(10) Patent No.: US 8,222,239 B2
(45) Date of Patent: *Jul. 17, 2012

(54) BRIDGED POLYCYCLIC COMPOUND BASED COMPOSITIONS FOR THE INHIBITION AND AMELIORATION OF DISEASE

(75) Inventor: Jeffery A. Whiteford, Belmont, CA (US)

(73) Assignee: AllAccem, Inc., San Carlos, CA (US)

( * ) Notice: Subject to any disclaimer, the term of this patent is extended or adjusted under 35 U.S.C. 154(b) by 172 days.

This patent is subject to a terminal disclaimer.

(21) Appl. No.: 12/035,351

(22) Filed: Feb. 21, 2008

(65) Prior Publication Data
US 2008/0275141 A1 Nov. 6, 2008

Related U.S. Application Data

(60) Provisional application No. 60/902,577, filed on Feb. 21, 2007, provisional application No. 60/964,312, filed on Aug. 10, 2007, provisional application No. 60/965,154, filed on Aug. 17, 2007, provisional application No. 61/029,332, filed on Feb. 16, 2008.

(51) Int. Cl.
*A61K 31/33* (2006.01)
*C07D 245/00* (2006.01)

(52) U.S. Cl. ........................... 514/183; 540/472

(58) Field of Classification Search .................. None
See application file for complete search history.

(56) References Cited

U.S. PATENT DOCUMENTS

| | | | |
|---|---|---|---|
| 2,455,807 A | 12/1948 | Redmon et al. | |
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee et al. | |
| 3,926,906 A | 12/1975 | Lee et al. | |
| 4,321,268 A | 3/1982 | Scherm et al. | |
| 4,544,359 A | 10/1985 | Waknine | |
| 4,547,531 A | 10/1985 | Waknine | |
| 4,666,896 A | 5/1987 | Warner, Jr. et al. | |
| RE32,581 E | 1/1988 | Scherm et al. | |
| 4,853,987 A | 8/1989 | Jaworski | |
| 4,946,942 A | 8/1990 | Fuller et al. | |
| 5,064,613 A | 11/1991 | Higgs et al. | |
| 5,084,096 A | 1/1992 | Stovicek | |
| 5,118,729 A | 6/1992 | Piechocki | |
| 5,145,853 A | 9/1992 | Metzger et al. | |
| 5,158,766 A | 10/1992 | Greenwald et al. | |
| 5,212,318 A | 5/1993 | Buckland | |
| 5,230,842 A | 7/1993 | Munde | |
| 5,276,068 A | 1/1994 | Waknine | |
| 5,344,856 A | 9/1994 | Klein | |
| 5,348,988 A | 9/1994 | Suh et al. | |
| 5,350,814 A | 9/1994 | McGarry et al. | |
| 5,386,018 A | 1/1995 | Au et al. | |
| 5,389,703 A | 2/1995 | Lee | |
| 5,393,516 A | 2/1995 | Rheinberger et al. | |
| 5,414,878 A | 5/1995 | Booth | |
| 5,494,987 A | 2/1996 | Imazato et al. | |
| 5,496,545 A | 3/1996 | Holmes-Farley et al. | |
| 5,521,246 A | 5/1996 | Tien et al. | |
| 5,534,565 A | 7/1996 | Zupancic et al. | |
| 5,587,023 A | 12/1996 | Booth | |
| 5,597,560 A | 1/1997 | Bergamini et al. | |
| 5,602,193 A | 2/1997 | Stark | |
| 5,658,994 A | 8/1997 | Burgoyne, Jr. et al. | |
| 5,667,775 A | 9/1997 | Holmes-Farley et al. | |
| 5,698,657 A | 12/1997 | Conner et al. | |
| 5,703,231 A | 12/1997 | Randall et al. | |
| 5,753,268 A | 5/1998 | Stolle et al. | |
| 5,753,269 A | 5/1998 | Groh et al. | |
| 5,824,734 A | 10/1998 | Yang | |
| 5,874,516 A | 2/1999 | Burgoyne, Jr. et al. | |
| 5,948,390 A | 9/1999 | Nelson et al. | |
| 5,990,110 A | 11/1999 | Firestone | |
| 6,008,313 A | 12/1999 | Walker et al. | |
| 6,020,370 A | 2/2000 | Horwell et al. | |
| 6,080,170 A | 6/2000 | Nash et al. | |
| 6,187,248 B1 | 2/2001 | O'Neill et al. | |
| 6,190,650 B1 | 2/2001 | Matthews et al. | |
| 6,218,455 B1 | 4/2001 | Smith et al. | |
| 6,235,811 B1 | 5/2001 | Robeson et al. | |
| 6,242,526 B1 | 6/2001 | Siddiqui et al. | |

(Continued)

FOREIGN PATENT DOCUMENTS

| | | |
|---|---|---|
| GB | 599722 | 1/1947 |
| JP | 2005154379 | 6/2005 |
| WO | 2007/070801 | 6/2007 |
| WO | 2008/103847 | 8/2008 |

OTHER PUBLICATIONS http://www.bio.brandeis.edu/classes/biochem104/hydrophobic_effect.pdf, 2007.
Chen, D. et al. "The synthesis of new binucleating polyaza macrocyclic and macrobicyclic ligands: dioxygen affinities of the cobalt complexes" Tetrahedron, vol. 47, Issue 34, Aug. 19, 1991, 6895-6902.
Rosenbaum, D. P. et al. "Effect of RenaGel, a non-absorbable, crosslinked, polymeric phosphate binder, on urinary phosphorus excretion in rats" Nephrol Dial Transplant, (1997) 12, 961-964.
Chertow, G. M. et al. "Poly[allylamine hydrochloride] (RenaGel): a noncalcemic phosphate binder for the treatment of hyperphosphatemia in chronic renal failure" Am J Kidney Dis., (1997), 29, 66-71.
David, S. k et al. "Towards a rational development of anti-endotoxin agents: novel approaches to sequestration of bacterial endotoxins with small molecules" J. Mol. Recognit. (2001); 14: 370-387.
March, Advanced Organic Chemistry, 1992, reaction 6-14, pp. 896-897.

(Continued)

*Primary Examiner* — Noble Jarrell
(74) *Attorney, Agent, or Firm* — Meyertons, Hood, Kivlin, Kowert & Goetzel, P.C.; Eric B. Meyertons

(57) ABSTRACT

A pharmaceutically active agent, a pharmaceutically active agent carrier and method of use thereof are described. In some embodiments, a system may include a composition. The composition may include one or more bridged polycyclic compounds. At least one of the bridged polycyclic compounds may include at least two cyclic groups, and at least two pharmaceutically active agents may be associated with the bridged polycyclic compound. In some embodiments, a bridged polycyclic compound may be pharmaceutically active. In some embodiments, a bridged polycyclic compound may be function as a carrier for pharmaceutically active agents.

47 Claims, 4 Drawing Sheets

U.S. PATENT DOCUMENTS

| | | | |
|---|---|---|---|
| 6,267,590 B1 | 7/2001 | Barry et al. |
| 6,268,126 B1 | 7/2001 | Neenan et al. |
| 6,309,221 B1 | 10/2001 | Jensen |
| 6,316,044 B2 | 11/2001 | Ottersbach et al. |
| 6,326,417 B1 | 12/2001 | Jia |
| 6,350,397 B1 | 2/2002 | Heikkila et al. |
| 6,416,546 B1 | 7/2002 | Kimura et al. |
| 6,436,419 B1 | 8/2002 | Sun et al. |
| 6,440,405 B1 | 8/2002 | Cooper et al. |
| 6,455,134 B1 | 9/2002 | Rabasco |
| 6,458,876 B1 | 10/2002 | Rabasco et al. |
| 6,464,971 B1 | 10/2002 | Matthews et al. |
| 6,465,042 B2 | 10/2002 | Saitoh et al. |
| 6,468,953 B1 | 10/2002 | Hitchems et al. |
| 6,492,445 B2 | 12/2002 | Siddiqui et al. |
| 6,500,004 B2 | 12/2002 | Jensen et al. |
| 6,538,143 B1 | 3/2003 | Pinschmidt, Jr. et al. |
| 6,562,329 B2 | 5/2003 | Hadvary et al. |
| 6,593,395 B2 | 7/2003 | Angeletakis et al. |
| 6,608,131 B1 | 8/2003 | Winterowd et al. |
| 6,617,142 B2 | 9/2003 | Keogh et al. |
| 6,632,291 B2 | 10/2003 | Rabon et al. |
| 6,716,955 B2 | 4/2004 | Burgoyne, Jr. |
| 6,720,368 B2 | 4/2004 | Field |
| 6,756,364 B2 | 6/2004 | Barbier et al. |
| 6,803,077 B2 | 10/2004 | Yu |
| 6,858,203 B2 | 2/2005 | Holmes-Farley et al. |
| 6,887,517 B1 | 5/2005 | Cook et al. |
| 6,900,265 B2 | 5/2005 | Schultz et al. |
| 6,908,609 B2 | 6/2005 | Simon et al. |
| 6,924,325 B2 | 8/2005 | Qian |
| 6,929,705 B2 | 8/2005 | Meyers et al. |
| 6,936,640 B2 | 8/2005 | McQueen et al. |
| 7,014,846 B2 | 3/2006 | Holmes-Farley et al. |
| 7,314,857 B2 | 1/2008 | Madhyastha |
| 7,342,083 B2 | 3/2008 | Chang et al. |
| 7,385,012 B2 | 6/2008 | Chang et al. |
| 7,713,955 B2 | 5/2010 | Whiteford et al. |
| 8,067,402 B2 | 11/2011 | Whiteford et al. |
| 8,067,403 B2 | 11/2011 | Whiteford et al. |
| 8,153,617 B2 | 4/2012 | Whiteford |
| 8,153,618 B2 | 4/2012 | Whiteford |
| 2001/0009931 A1 | 7/2001 | Pflug et al. |
| 2002/0151570 A1 | 10/2002 | Kretschik et al. |
| 2002/0177828 A1 | 11/2002 | Batich et al. |
| 2003/0091641 A1 | 5/2003 | Tiller et al. |
| 2003/0134933 A1 | 7/2003 | Jin et al. |
| 2003/0149149 A1 | 8/2003 | Carlisle et al. |
| 2003/0175659 A1 | 9/2003 | Tiba et al. |
| 2003/0190820 A1 | 10/2003 | Hill et al. |
| 2003/0199605 A1 | 10/2003 | Fischer |
| 2004/0092896 A1 | 5/2004 | Thompson |
| 2004/0199994 A1 | 10/2004 | Sherif et al. |
| 2004/0267009 A1 | 12/2004 | Redko et al. |
| 2005/0008763 A1 | 1/2005 | Schachter |
| 2005/0008777 A1 | 1/2005 | McCleskey et al. |
| 2005/0118911 A1 | 6/2005 | Oles et al. |
| 2005/0129937 A1 | 6/2005 | Patton et al. |
| 2005/0158252 A1 | 7/2005 | Romanowski et al. |
| 2005/0175966 A1 | 8/2005 | Falsafi et al. |
| 2005/0208249 A1 | 9/2005 | Wen et al. |
| 2005/0249818 A1 | 11/2005 | Sawan et al. |
| 2005/0252413 A1 | 11/2005 | Kangas et al. |
| 2005/0256223 A1 | 11/2005 | Kolb et al. |
| 2005/0265931 A1 | 12/2005 | Qian |
| 2005/0271780 A1 | 12/2005 | Schroeder et al. |
| 2007/0202342 A1 | 8/2007 | Whiteford et al. |
| 2008/0020127 A1 | 1/2008 | Whiteford et al. |
| 2008/0021212 A1 | 1/2008 | Whiteford et al. |
| 2008/0207581 A1 | 8/2008 | Whiteford et al. |
| 2009/0054528 A1 | 2/2009 | Whiteford |
| 2009/0069435 A1 | 3/2009 | Whiteford |
| 2009/0074833 A1 | 3/2009 | Whiteford |
| 2009/0105262 A1 | 4/2009 | Whiteford |
| 2009/0270005 A1 | 10/2009 | Takahashi et al. |
| 2010/0004218 A1 | 1/2010 | Whiteford |
| 2010/0016270 A1 | 1/2010 | Whiteford |
| 2011/0015300 A1 | 1/2011 | Whiteford et al. |

OTHER PUBLICATIONS

Dayagi, S. et al. "Methods of formation of the carbon-nitrogen double bond", chapter 2 of The Chemistry of the Carbon-Nitrogen Double Bond, editor Saul Patai, 1970, pp. 61-69.

Savica, V. et al. "Phosphate binders and management of hyperphosphataemia in end-stage renal disease" Nephrol Dial Transplant (2006) 21: 2065-2068.

Co-Pending U.S. Appl. No. 12/035,351 entitled "Bridged Polycyclic Compound Based Compositions for the Inhibition and Amelioration of Disease" to Whiteford filed Feb. 21, 2008.

Hossain, M. A. et al. "Parallels in Cation and Anion Coordination: A New Class of Cascade Complexes" Angew. Chem. Int. Ed., vol. 41, No. 13, 2335-2338, 2002.

Chen, Q. Y. et al. "Synthesis, crystal structure and properties of the first trinuclear copper(II) cryptate bridged by an imidazole anion" J. Chem. Soc., Dalton Trans., 1315-1318, 2002.

Chen, Q. Y. et al. "A study on the heterodinuclear cryptates [LnCuL(DMF)](ClO4)2•MeCN (LN=Gd, Eu, Tb, Dy, Y)—synthesis, characterization, magnetic and electrochemical properties" J. Chem. Soc., Dalton Trans., 2873-2878, 2002.

Kang, S. G. et al. "Template Synthesis and Crystal Structure of a Novel Mononuclear Nickel(II) Complex with a Face-ti-Face Bis(macrocyclic) Ligand" Inorg. Chem., vol. 36, No. 11, 2478-2481, 1997.

Conejo-Garcia, A. et al. "Synthesis and NMR Studies on a C3-Symmetrical Triquinolina Triscationic Bicyclophane" J. Org. Chem., vol. 70, 5748-5751, 2005.

Shintani, H. "Modification of Medical Device Surface to attain Anti-Infection" Trends Biomater. Artif. Organs, vol. 18 (1), 1-8, 2004.

Kickelbick, G. "Concepts for the incorporation of inorganic building blocks into organic polymers on a nanoscale" Prog. Polym. Sci., vol. 28, 83-114, 2003.

Kull, F. C. et al. "Mixtures of Quaternary Ammonium Compounds and Long-chain Fatty Acids as Antifungal Agents" Appl. Microbiol., vol. 9, No. 6, 538-541, 1961.

Skold, K. et al. "Effect of a chlorhexidine/thymol-containing varnish on prostaglandin E2 levels in gingival crevicular fluid" Eur. J. Oral Sci.., vol. 106, 571-575, 1998.

Co-Pending U.S. Appl. No. 12/228,262 entitled, "Bridged Polycyclic Compound Based Compositions for Coating Oral Surfaces in Pets" to Whitedford filed Aug. 11, 2008.

Co-Pending U.S. Appl. No. 12/228,263 entitled, "Bridged Polycyclic Compound Based Compositions for Coating Oral Surfaces in Humans" to Whiteford filed Aug. 11, 2008.

Co-Pending U.S. Appl. No. 12/228,264 entitled, "Bridged Polycyclic Compound Based Compositions for Topical Applications for Pets" to Whiteford filed Aug. 11, 2008.

Co-Pending U.S. Appl. No. 12/193,529 entitled, "Bridged Polycyclic Compound Based Compositions for Controlling Bone Resorption" to Whiteford filed Aug. 18, 2008.

Zhuang, X.-M. et al. "Cyanide and imidazolate bridged macrocyclic dinuclear CuII complexes: Synthesis, structure and magnetic properties" Inorganica Chimica Acta 358 (2005) 2129-2134.

Pierre, J. L. et al. "Synthesis of a Novel Macrobicyclic Cavity Possessing Six Convergent Hydroxyl Groups and Acting as a Siderophore" Angew. Chem. Int. Ed. Engl. 30 (1991) No. 1, 85-86.

Shin, C. et al. "Novel Synthesis of the Main Central 2,3,6-Trisubstituted Pyridine Skeleton [Fragment A-B-C] of a Macrobicyclic Antibiotic, Cyclothiazomycin" Bull. Chem. Soc. Jpn. 75, (2002) 1583-1596.

Dirksen, A. et al. "Nucleophilic Catalysis of Oxime Ligation" Angew. Chem. Int. Ed. (2006) 45, 7581-7584.

Marcil, V. et.al. "Butyrate Impairs Lipid Transport by Inhibiting Microsomal Triglyceride Transfer Protein in Caco-2 Cells" J. Nutr. 2003, 133: 2180-2183.

Wren et al. "Dirlotapide: a review of its properties and role in the management of obesity in dogs" 2007 J. vet. Pharmacol. Therap. 30 (Suppl. 1), 11-16.

Hussain, M. M. et.al. "Microsomal triglyceride transfer protein and its role inapoB-lipoprotein assembly" Journal of Lipid Research, 2003, vol. 44, 22-32.

Ni, B. et al. "Design and Synthesis of Pyridinium Chiral Ionic Liquids Tethered to a Urea Functionality", J. Org. Chem. 2006, 71, 26, 9857-9860.

Curd, F. H. S. et al. "Synthetic Antimalarials, Part X, Some Aryldiguanide (-biguanide) Derivatives" J. Chem. Soc. 729-737 (1946).

Chandler, C.E. et al. "CP-346086: an MTP inhibitor that lowers plasma cholesterol and triglycerides in experimental animals and in humans" Journal of Lipid Research, vol. 44, 1887-1901, Oct. 2003.

Curd, F. H. S. et al. "Synthetic Antimalarials, Part XXVIII, An alternative route to N1-aryl-N5-alkyldiguanides" J. Chem. Soc. 1630-1636 (1948).

Chand, D. K. et al. "Synthesis of a Heteroditopic Cryptand Capable of Imposing a Distorted Coordination Geometry onto Cu(II): Crystal Structures of the Cryptand (L), [Cu(L)(CN)](picrate), and [Cu(L)(NCS)](picrate) and Spectroscopic Studies of the Cu(II) Complexes" Inorg. Chem., 1996, vol. 35, 3380-3387.

Chen, C. Z. et.al. "Quaternary Ammonium Functionalized Poly(propylene imine) Dendrimers as Effective Antimicrobials: Structure-Activity Studies" Biomacromolecules, 2000, vol. 1, No. 3, 473-480.

Cunliffe, D. et al., "Bacterial Adhesion at Synthetic Surfaces" Applied and Environmental Microbiology, Nov. 1999, vol. 65, No. 11, 4995-5002.

Dibrov, P. et al. "Chemiosmotic Mechanism of Antimicrobial Activity of Ag+ in Vibrio cholerae" Antimicrobial Agents and Chemotherapy, Aug. 2002, vol. 46, No. 8, 2668-2670.

Drew, M. G. B. et al., "d10 Cations within triple-helical cryptand hosts; a structural and modelling study" J. Chem. Soc., Dalton Trans., 2000, 1513-1519.

Gibb, B. C. "Strict Self-Assembly and Self-Assembly with Covalent Modifications" Encyclopedia of Supramolecular Chemistry, Aug. 17, 2004, 1372-1378, DOI: 10.10811E-ESMC-120012781.

Gomez, R. et al., "Synthesis, characterization and photocativity of nanosized sol-gel TiO2-ZrO2 mixed oxides." The 13th International Congress on Catalysis, Jul. 10-15, 2004.

Han, S. et al., "Low-Temperature Synthesis of Highly Crystalline TiO2 Nanocrystals and their Application to Photocatalysis" Small, 2005, vol. 1, No. 8-9, 812-816.

Huang, J. et al., "Thermomechanical properties of polyimide-epoxy nanocomposites from cubic silsesquioxane epoxides" J. Mater. Chem., 2004, vol. 14, 2858-2863.

Imhof, A. "Preparation and Characterization of Titania-Coated Polystyrene Spheres and Hollow Titania Shells" Langmuir, 2001, vol. 17, 3579-3585.

Kraft, A. et al. "Electroluminescent Conjugated Polymers-Seeing Polymers in a New Light" Angew. Chem. Int. Ed., 1998, vol. 37, 402-428.

Lawrence, N. J. et al., "Polymethylhydrosiloxane: a versatile reducing agent for organic synthesis" J. Chem. Soc., Perkin Trans. 1, 1999, 3381-3391.

Lin, J. et al. "Insights into bactericidal action of surface-attached poly(vinyl-N-hexylpyridinium) chains" Biotechnology Letters, 2002, vol. 24, 801-805.

Lin, J. et al. "Making thin polymeric materials, including fabrics, microbicidal and also water-repellent" Biotechnology Letters, 2003, vol. 25, 1661-1665.

Maness, P. et al. "Bactericidal Activity of Photocatalytic TiO2 Reaction: toward an Understanding of Its Killing Mechanism" Applied and Environmental Microbiology, Sep. 1999, vol. 65, No. 9, 4094-4098.

Marlin, D. S. et al. "Complexation-Induced Translational Isomerism: Shuttling through Stepwise Competitive Binding" Angewandte Chemie, 2006, vol. 45, pp. 77-83.

Ming, W. et al., "Superhydrophobic Films from Raspberry-like Particles" Nano. Lett, Oct. 1, 2005, vol. 5, No. 11, 2298-2301.

Ni, B. et al. "Design and Synthesis of Pyridinium Chiral Ionic Liquids Tethered to a Urea Functionality" J. Org. Chem., 2006, vol. 71, 9857-9860.

Pernak, J. et al., "Synthesis and anti-microbial activities of some pyridinium salts with alkoxymethyl hydrophobic group" Eur. J. Med. Chem., 2001, vol. 36, 899-907.

Rivas, F. M. et al. "Aromatic Amination/Imination Approach to Chiral Benzimidazoles" J. Org. Chem., 2002, vol. 67, 1708-1711.

Rowan, S. J. et al. "Dynamic Covalent Chemistry" Angew Chem Int Ed Engl., 2002, vol. 41, No. 6, 898-952.

Salvatore, R. N. et al., "Synthesis of secondary amines" Tetrahedron, 2001, vol. 57, 7785-7811.

Schweizer, H. P. "Efflux as a mechanism of resistance to antimicrobials in Pseudomonas aeruginosa and related bacteria: unanswered questions" Genetics and Molecular Research, Mar. 31, 2003, vol. 2, No. 1, 48-62.

Slack, J. M. et al. "Identification of Actinomyces and Related Bacteria in Dental Calculus by the Fluorescent Antibody Technique" J. Dent. Res., 1971, vol. 50, No. 1, 78-82.

Strachan, J. "Synthesis and Characterization of Tetrachlorodiarylethyne-Linked Porphyrin dimers. Effects of Linker Architecture on Intradimer Electronic Communication" Inorg. Chem., 1998, vol. 37, 1191-1201.

Thorsteinsson, T. et.al. "Soft Antimicrobial Agents: Synthesis and Activity of Labile Environmentally Friendly Long Chain Quaternary Ammonium Compounds" J. Med. Chem., 2003, vol. 46, 4173-4181.

Tiller, J. C. et al. "Designing surfaces that kill bacteria on contact" PNAS, 2001, vol. 98, No. 11, 5981-5985.

Tom, R. T. et al., "Freely Dispersible Au@TiO2, Au@ZrO2, Ag@TiO2, and Ag@ZrO2 Core-Shell Nanoparticles: One-Step Synthesis, Characterization, Spectroscopy, and Optical Limiting Properties" Langmuir, 2003, vol. 19, 3439-3445.

Trentler, T. J. et al., "Epoxy Resin-Photopolymer Composites for Volume Holography" Chem. Mater., 2000, vol. 12, 1431-1438.

Waschinski, C. J. et al. "Poly(oxazoline)s with Telechelic Antimicrobial Functions" Biomacromolecules, 2005, vol. 6, 235-243.

Zhang, X. "From Supramolecular Vanadate Receptors to Enzyme Models of Vanadium Haloperoxidase" Philosophisch-Naturwissenschaftlichen Fakultat der Universitat Basel, Feb. 2005.

Zhisheng, C. et al "Recent Advances in Antimicrobial Dendrimers", Advanced Materials 2000, vol. 12, No. 11, 843-846.

International Search Report and Written Opinion for PCT/US06/61936 mailed Sep. 12, 2007.

Co-Pending U.S. Appl. No. 11/800,052 entitled, "Methods and Systems for Coating a Surface" to Whiteford et al. filed May 2, 2007.

Co-Pending U.S. Appl. No. 12/775,277 entitled, "Methods and Systems for Coating a Surface" to Whiteford et al. filed May 6, 2010.

Examination Report for Patent Application No. 569756 mailed Feb. 26, 2010.

Examination Report for New Zealand Patent Application No. 579785 mailed Oct. 8, 2010 pp. 2.

Written Opinion for European Application No. 08 730 417.6-1216 mailed Aug. 5, 2010.

Office Action for U.S. Appl. No. 11/638,327 mailed on Oct. 2, 2008.
Office Action for U.S. Appl. No. 11/638,327 mailed on May 29, 2009.
Office Action for U.S. Appl. No. 11/638,327 mailed on Nov. 16, 2009.
Office Action for U.S. Appl. No. 11/638,327 mailed on Jun. 1, 2010.
Advisory Action for U.S. Appl. No. 11/638,327 mailed on Sep. 14, 2010.
Office Action for U.S. Appl. No. 11/800,052 mailed on Mar. 5, 2009.
Office Action for U.S. Appl. No. 11/800,052 mailed on Oct. 29, 2009.
Office Action for U.S. Appl. No. 11/800,069 mailed on Aug. 18, 2009.
Office Action for U.S. Appl. No. 11/800,069 mailed on Mar. 22, 2010.
Advisory Action for U.S. Appl. No. 11/800,069 mailed on Jun. 9, 2010.

Bhattacharjee, M. et al. "Synthesis of a New Macrocyclic Ligand with Six Amide Receptor Sites" Tetrahedron Letters (1996) vol. 37, No. 20, 3579-3580.

Office Action for U.S. Appl. No. 11/638,327 mailed on Jan. 20, 2011.
Non-Final Office Action for U.S. Appl. No. 12/228,264 mailed on Mar. 31, 2011.
Final Office Action for U.S. Appl. No. 12/035,351 mailed on Feb. 3, 2011.
Non-Final Office Action for U.S. Appl. No. 12/228,262 mailed on Mar. 31, 2011.

International Preliminary Report on Patentability for PCT/US2009/053464 mailed Feb. 24, 2011.
Non-Final Office Action for U.S. Appl. No. 12/228,263 mailed on Mar. 31, 2011.
Advisory Action for U.S. Appl. No. 11/638,327 mailed on Jul. 28, 2011.
Notice of Allowance for U.S. Appl. No. 11/638,327 mailed on Aug. 24, 2011.
Non-Final Office Action for U.S. Appl. No. 11/800,066 mailed on Aug. 1, 2011.
Final Office Action for U.S. Appl. No. 11/800,069 mailed on Sep. 16, 2011.
Notice of Allowance for U.S. Appl. No. 11/800,069 mailed on Oct. 4, 2011.
Examination Report for New Zealand Patent Application No. 579785 mailed Aug. 1, 2011 pp. 2.
Non-Final Office Action for U.S. Appl. No. 12/035,351 mailed on Oct. 24, 2011.
Final Office Action for U.S. Appl. No. 12/228,262 mailed on Dec. 27, 2011.
Final Office Action for U.S. Appl. No. 12/228,263 mailed on Oct. 18, 2011.
Notice of Allowance for U.S. Appl. No. 12/228,263 mailed on Nov. 25, 2011.
Final Office Action for U.S. Appl. No. 12/228,264 mailed on Oct. 18, 2011.
Notice of Allowance for U.S. Appl. No. 12/228,264 mailed on Nov. 25, 2011.
Final Office Action for U.S. Appl. No. 11/638,327 mailed on Jul. 11, 2011.
CC75—Examination Report for Patent Application No. 569756 mailed Apr. 5, 2011.
Advisory Action for U.S. Appl. No. 12/035,351 mailed on May 20, 2011.
Non-Final Office Action for U.S. Appl. No. 12/193,529 mailed on May 27, 2011.
Office Action for U.S. Appl. No. 11/800,069 mailed on Jan. 6, 2011.
CC78—Examination Report for Australian Patent Application No: 2006325820 mailed Feb. 2 and 13, 2012. pp. 4.
Notice of Allowance for U.S. Appl. No. 12/035,351 mailed on Mar. 20, 2012.
CC79—Examination Report for New Zealand Patent Application No. 579785 mailed Mar. 13, 2012. pp. 1.
Notice of Allowance for U.S. Appl. No. 12/228,262 mailed on Feb. 8, 2012.
CC81—Examination Report for New Zealand Patent Application No. 579785 mailed Apr. 12, 2012. pp. 1.

BRIDGED POLYCYCLIC COMPOUND BASED COMPOSITIONS FOR THE INHIBITION AND AMELIORATION OF DISEASE This application claims priority to U.S. Provisional Patent Application No. 60/902,577 entitled "BRIDGED POLYCYCLIC COMPOUND BASED COMPOSITIONS FOR THE INHIBITION AND AMELIORATION OF DISEASE" filed on Feb. 21, 2007, U.S. Provisional Patent Application No. 60/964,312 entitled "BRIDGED POLYCYCLIC COMPOUND BASED COMPOSITIONS FOR COATING SURFACES" filed on Aug. 10, 2007, U.S. Provisional Patent Application No. 60/965,154 entitled "BRIDGED POLYCYCLIC POLYMER BASED COMPOSITIONS FOR THE INHIBITION AND AMELIORATION OF DISEASE" filed on Aug. 17, 2007, and U.S. Provisional Patent Application No. 61/029,332 entitled "BRIDGED POLYCYCLIC COMPOUND BASED COMPOSITIONS FOR COATING SURFACES" filed on Feb. 16, 2008, all of which are incorporated by reference herein.

BACKGROUND OF THE INVENTION

1. Field of the Invention

The present disclosure generally relates to bridged polycyclic based compounds for the inhibition and amelioration of disease. More particularly, the disclosure generally relates to systems and methods for formulating antiviral, antibacterial, antifungal, antidisease compositions using these bridged polycyclic based compounds.

2. Description of the Relevant Art

Dendrimers are basically branched polymers with densely packed end-functional groups that may be used to attach the dendrimers to biologically molecules (e.g., drugs, targeting ligands and imaging agents). Cancer is one of the applications of these unique materials. Since a significant portion of administered dose of pharmaceutical drugs (e.g., anticancer, antiviral) is lost in the circulation due to impaired uptake by the cells especially in the case of drug resistance cells, the actual concentration of the drug inside the cells is much less than what is present extracellularly. Hence, to accomplish highly effective treatment of diseases (e.g., cancer) it is crucial to increase the intracellular amount of the drug. Dendrimers have already been used as a carrier agent for several known anticancer and antiviral agents. Attaching these known agents to a dendrimer has been shown to increase the activity of the agent verses using the agent alone and uncoupled to a dendrimer. However, there are practical problems associated with using dendrimers, especially when upscaling production to commercial quantities.

At least two methods exist for the synthesis of dendrimers: a divergent approach, where the dendrimer is assembled in a totally linear manner or a convergent method where fragments of the dendrimer are condensed together. These two methods both suffer from problems when it comes to practical synthesis. In particular, problems include the necessity for repeated and time-consuming purifications.

Additional problems associated with the synthesis of dendrimers include defects in the molecular structure, and molecular structures and typically unavoidable encapsulation of other molecules within the dendrimer Therefore there is a need for a pharmaceutical composition comprising a compound which increases the intracellular amount of pharmaceutical drugs but which is easier and cheaper to synthesize than dendrimers and which are capable of attaching different functionalities more easily.

In the field of dentistry, the increased average age of patients and improvements in the treatment of teeth have resulted in an increased average age of teeth which need to be treated.

The prevention of cavities and periodontitis can therefore not be limited to children and adolescents as the lifelong conservation of teeth demands a preventive approach also for middle-aged and elderly patients. Otherwise there is the risk that the positive results of early preventive measures will be lost within a few years ending up with tooth loss at old age.

Dental applications are challenging and require top performance from dental care providers and materials technology. Materials used in these applications need to be comfortable, hard, wear resistant, strong and yet also visibly appealing. Poorly formulated dental materials can result in discomfort, complications, and increased health care cost to consumers.

All types of teeth and gum diseases can lead to serious health problems in pets. Dogs and cats make use of their teeth more than humans do. Therefore, toothache, dental disease and loss of teeth can all have serious consequences for pets. Damage to the teeth and gums in pets to date is permanent and irreversible.

Maintenance of good oral health and prevention of oral disease is a necessity for both humans and animals. Unlike animals humans have the ability to exercise control over oral and dental hygiene by using proper preventative techniques. Humans still experience oral problems ranging from cavities to more severe cases of gum disease.

According to the American Veterinary Dental Society, eighty percent of dogs and seventy percent of cats have periodontal (gum) disease by the age of three. Proper dental care could increase the life of these animals by two to five years.

There are clear indications that oral health status has an effect on a subject's general health. Periodontal disease may result in bacteria and toxins entering the bloodstream with potentially detrimental effects on one or more internal organs. Conversely, poor systemic health may manifest in the oral cavity in various ways and may also exacerbate periodontal disease. An animal's dental examination is therefore not always limited to the oral cavity but frequently includes a general physical examination. Laboratory examinations, to evaluate systemic disease concerns, are also commonly performed. Some dogs and cats suffer from chronic oral infection or stomatitis, a poorly understood condition that is frustratingly difficult to treat.

What is needed therefore is an easy to use, effective system for maintaining good general health as well as preventing and treating disease. Preferably such methods and compositions should be easy-to-use and comprise antimicrobial agents. Such methods and compositions should be affordable, safe and easy to use on a regular basis.

SUMMARY

The present invention solves the problems described above by providing novel compositions and methods for reducing and/or ameliorating maladies associated with an oral cavity and/or an otic cavity. Unlike currently available products, the present invention provides unique methods and compositions that are safe and effective for regular use by both humans and animals.

In some embodiments, a chemical composition may include a chemical compound. The chemical compound may include one or more bridged polycyclic compounds. At least one of the bridged polycyclic compounds may include at least two cyclic groups. At least two pharmaceutically active agents may be coupled to the bridged polycyclic compound.

In some embodiments, at least one of the pharmaceutically active agents may include an anticancer agent, an anti-inflammatory agent, an antimicrobial agent, a lipase inhibitor, a bile acid sequestrant, a cholesterol reduction agent, a periodontal disease inhibitor, a periodontal bacteria attachment inhibitor, a periodontal disease enzyme inhibitor, and/or a periodontal disease enzyme attachment inhibitor.

In some embodiments, a chemical composition may include a chemical compound, wherein the chemical compound has a general structure (Ia):

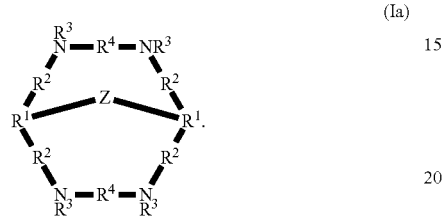

Each $R^1$ may be independently an alkyl group, a substituted alkyl group, an aryl group, a substituted aryl group, N, $N^+R^3$, a heterocycle group, or a substituted heterocycle group. Each $R^2$ may be independently an alkyl group, a substituted alkyl group, an aryl group, a substituted aryl group, a heterocycle group, a substituted heterocycle group, a covalent bond, or an alkene. Each $R^3$ may be independently a pharmaceutically active agent, an alkyl group, a substituted alkyl group, an aryl group, a substituted aryl group, a heterocycle group, a substituted heterocycle group, an alkene, an ether, a PEG, or a PEI. Each $R^4$ may be independently an alkyl group, a substituted alkyl group, an aryl group, a substituted aryl group, a heterocycle group, a substituted heterocycle group, an ether, an amide, an alcohol, an ester, a sulfonamide, a sulfanilamide, or an alkene. Z may include at least one bridge. At least one of the bridges may be $-R^2-N^+R^4-NR^3{}_2-R^2-$, $-R^2-NR^3-R^4-N^+R^3{}_2-R^2$, $R^2-NR^3-R^4-NR^3-R^2-$ or $-R^2-N=R^4=N-R^2-$. Each bridge may independently couple $R^1$ to $R^1$. The chemical compound may include one or more negatively charged counter ions.

In some embodiments, a bridged polycyclic compound may include a salt of compound Ia.

In some embodiments, a chemical composition may include a chemical compound, wherein the chemical compound has a general structure:

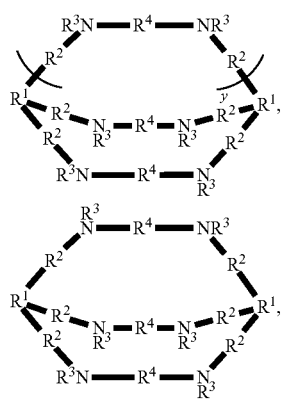

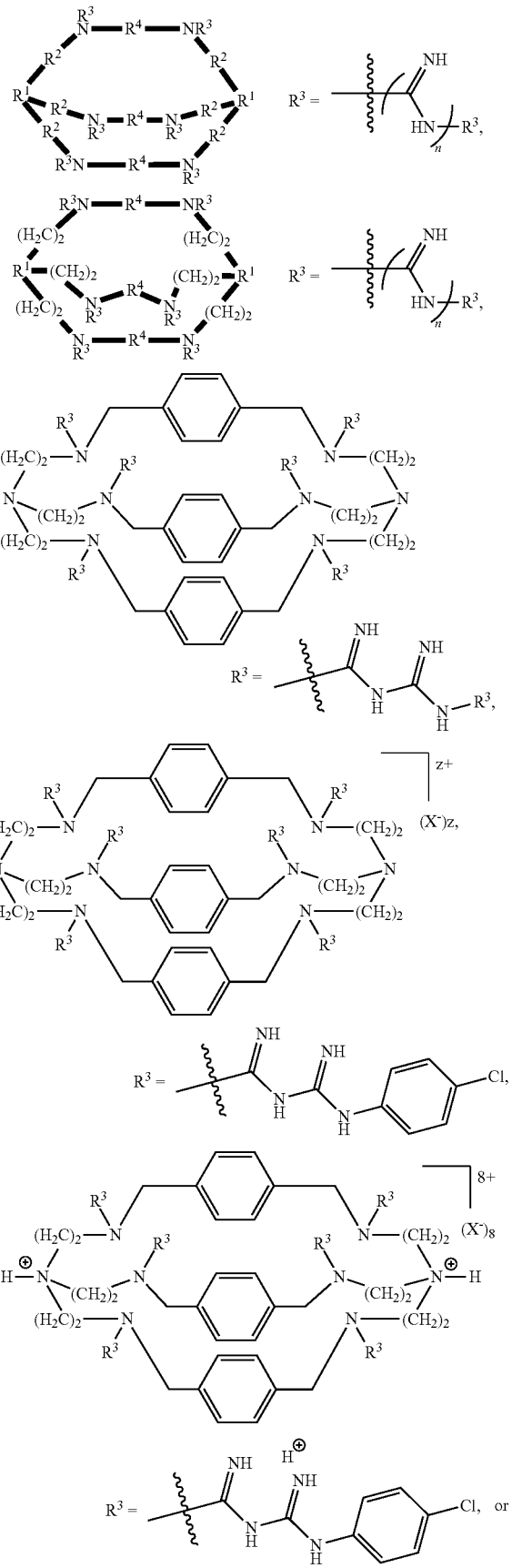

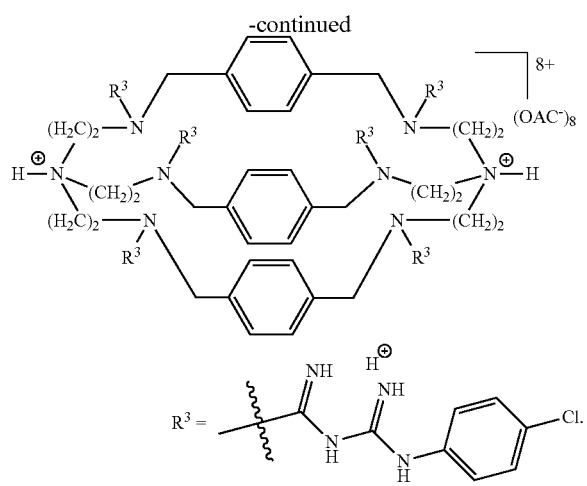

In some embodiments, $R^3$ may include a guanidine moiety and/or a halogenated aryl moiety.

In some embodiments, a chemical compound is a salt of the chemical compound. At least one counterion forming the salt may include an acetate ion.

In some embodiments, a chemical composition may include a polymer or a prepolymer. At least one polymer is poly(vinyl acetate-co-crotonic acid).

In some embodiments, a z may represent a charge on the chemical compound and an appropriate number of counterions. z may range from 1-16, 2-14, 6-14, or 8-14.

In some embodiments, y may represent a number of bridges coupling the Nitrogens of the chemical compound. y may range from 3-8, 3-5, or 3-4.

In some embodiments, a chemical composition may include at least one solvent.

In some embodiments, a chemical composition may include water and/or an alcohol (e.g., ethanol).

In some embodiments, a chemical composition may include a pharmaceutically acceptable viscous liquid (e.g., glycerin).

In some embodiments, a protective coating composition may include a compound. A compound may include a bridged polycyclic compound. A bridged polycyclic compound may be a cavitand. Portions of the bridged polycyclic compound may include two or more quaternary ammonium moieties. The coating composition may be antimicrobial.

In some embodiments, a protective coating composition may be antimicrobial.

In some embodiments, a chemical composition may include a chemical compound, wherein the chemical compound has a general structure (I):

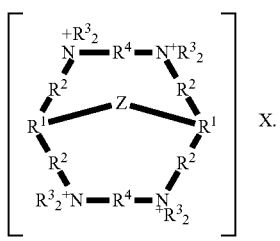

In some embodiments, a chemical composition may include one or more polymerizable compounds.

In some embodiments, a chemical composition may include one or more polymerizable compounds, wherein the chemical composition is configured such that, when the chemical composition is applied to a surface and cured, then at least a portion of the composition forms an antimicrobial coating over at least a portion of the surface.

In some embodiments, at least one $R^3$ may include at least one phenol moiety.

In some embodiments, at least one $R^3$ may include at least one azole moiety.

In some embodiments, at least one $R^3$ is a benzyl group.

In some embodiments, at least one $R^3$ includes a halogen substituted aryl group.

In some embodiments, at least one X is an anion. In some embodiments, at least one X is a polymer. In some embodiments, at least one X is a monomer. In some embodiments, at least one X is a halogen. In some embodiments, at least one X is iodine, bromine, or chlorine. In some embodiments, at least one X contains boron. In some embodiments, at least one X is a borate. In some embodiments, at least one X is a tetrafluoroborate. In some embodiments, at least one X contains nitrogen. In some embodiments, at least one X is a nitrate. In some embodiments, at least one X is $PY_6$, wherein Y is a halogen. In some embodiments, at least one X is hexafluorophosphate. In some embodiments, at least one X is $NTf_2$, and wherein Tf is bis(trifluoromethanesulfonyl)imide.

In some embodiments, Z is one bridge such that the chemical compound has a general structure (II):

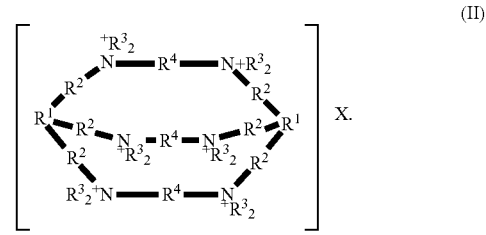

In some embodiments, Z is one bridge such that the chemical compound has a general structure (IIa):

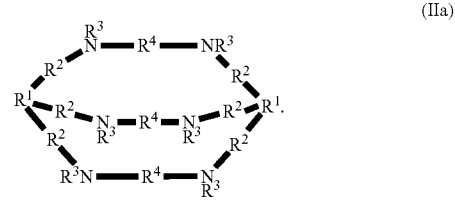

In some embodiments, Z is two bridges such that the chemical compound has a general structure (III):

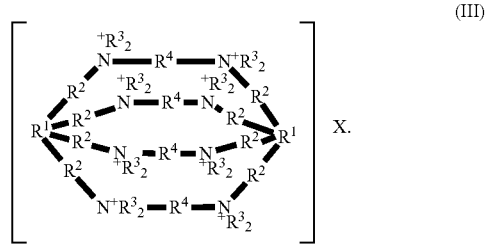

In some embodiments, Z is two bridges such that the chemical compound has a general structure (IIIa):

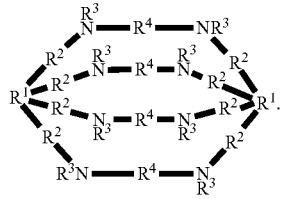
(IIIa)

In some embodiments, Z is one bridge such that the chemical compound has a general structure (IV):

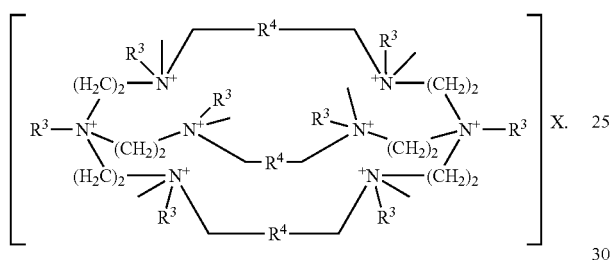
(IV)

At least one $R^3$ may be a methyl group. At least one $R^3$ may be a $C_5$-$C_7$ alkyl group or a $C_5$-$C_7$ substituted alkyl group. At least one $R^4$ may be an aryl group or a substituted aryl group.

In some embodiments, Z is one bridge such that the chemical compound has a general structure (IVa):

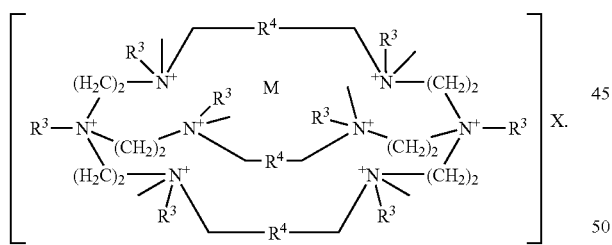
(IVa)

At least one $R^3$ may be a methyl group. At least one $R^3$ may be a $C_5$-$C_7$ alkyl group or a $C_5$-$C_7$ substituted alkyl group. At least one $R^4$ may be an aryl group or a substituted aryl group. M may include one or more guest molecules associated with one or more portions of compound (IVa).

In some embodiments, a compound may include a shape with a substantially curved surface.

In some embodiments, a coating may inhibit microbial adhesion.

In some embodiments, a compound may have a minimum inhibitory concentration of less than 0.1 mg/mL.

In some embodiments, a composition may have a minimum inhibitory concentration of less than 0.05 mg/mL.

In some embodiments, at least one $R^1$ is $N^+R^3$. In some embodiments, at least one $R^1$ is

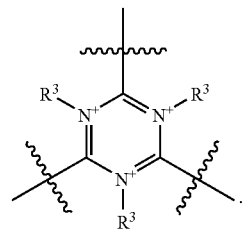

In some embodiments, at least one $R^3$ is hydrophilic. In some embodiments, at least one $R^3$ is a polymer.

In some embodiments, at least one $R^3$ is an oxazoline polymer. In some embodiments, at least one $R^3$ is hydrophobic.

In some embodiments, at least one $R^4$ may be

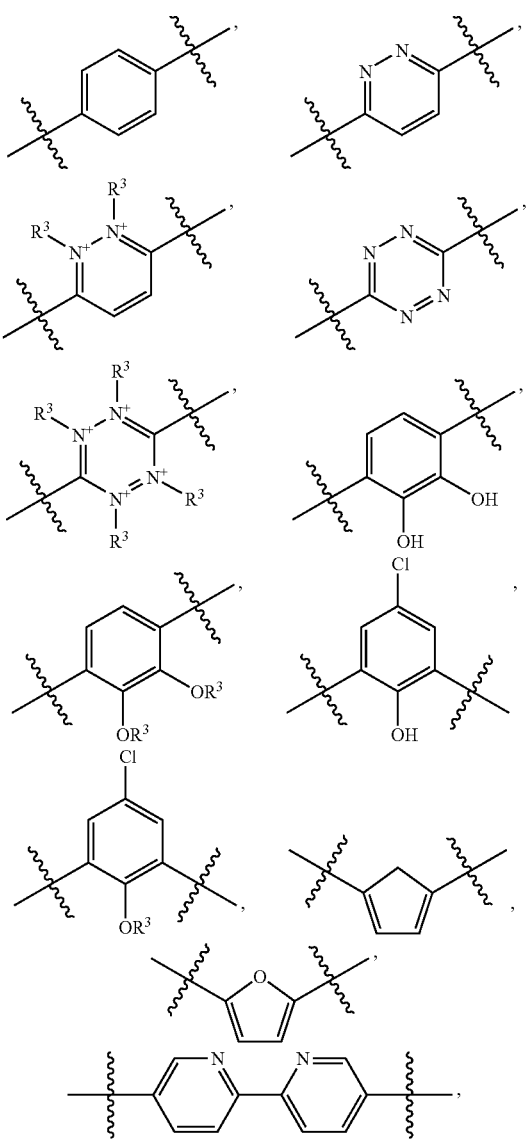

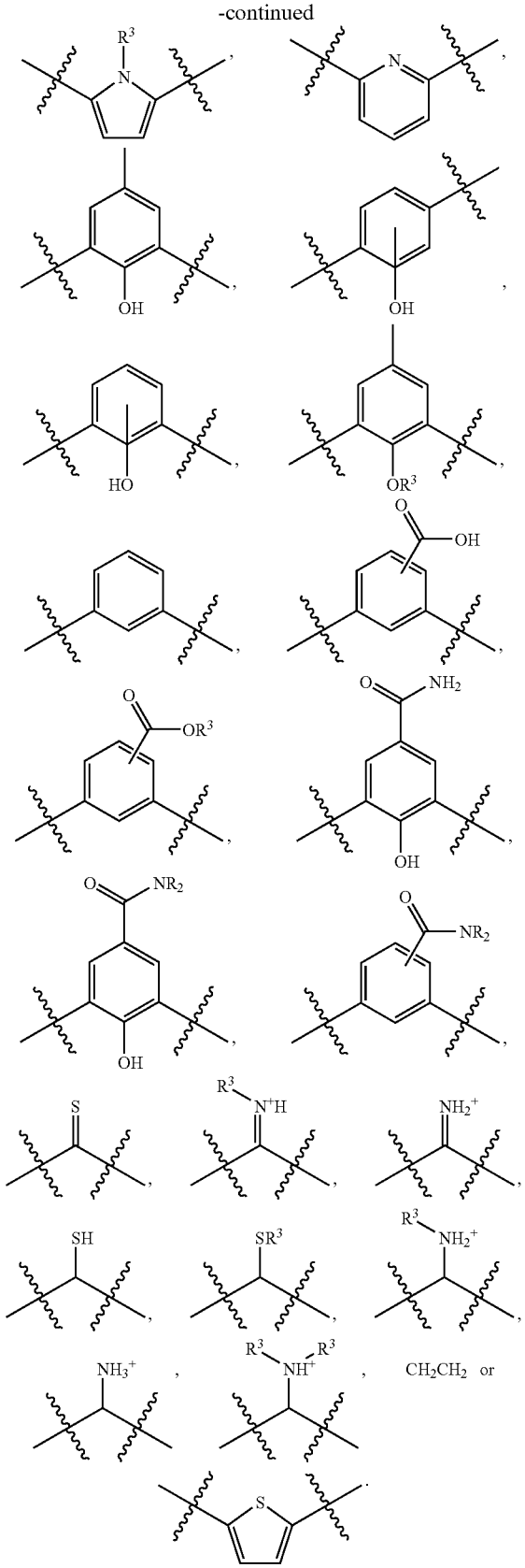

In some embodiments, a composition may include at least one metal (M) coordinated to at least a portion of the compound. At least one M may include a cation. At least one M may be positioned inside a space defined by $R^2$ and $R^4$, and wherein at least one M is coordinated to one or more $N^+R^3{}_2$'s.

In some embodiments, at least one X may include a halogen ion.

In some embodiments, at least one X may include one or more elements with antimicrobial activity.

In some embodiments, at least one X may include one or more elements with anti-inflammatory activity.

In some embodiments, at least one X may include boron.

In some embodiments, a composition may include one or more metals and/or metal ions with antimicrobial properties.

In some embodiments, a composition may include one or more metals and/or metal ions with anti-inflammatory properties.

In some embodiments, a composition may include one or more metals and/or metal ions, and wherein one or more of the metals are light activated such that activating the metal with light increases the antimicrobial activity of the metal.

In some embodiments, a composition may include one or more metals and/or metal ions, and wherein at least one metals and/or metal ions is silver. At least one metals and/or metal ions may be zinc, copper, gold, or cesium. At least one metals and/or metal ions may be silver, zinc, copper, gold, calcium, nickel, cobalt, barium, strontium, lead, lanthanum, iron, manganese, cadmium, magnesium, Y, La, Ce, Pr, Nd, Eu, Gd, Tb, Dy, Ho, Er, Tm, Yb, Ce, or alkaline earth metals.

In some embodiments, at least a portion of a chemical composition may form an antimicrobial coating over at least a portion of a surface. The chemical composition may include one or more bridged polycyclic compounds. At least one of the bridged polycyclic compounds may include at least two cyclic groups.

In some embodiments, a compound and/or a composition may have a minimum inhibitory concentration of greater than 900 µM (e.g., 900 µM-1500 µM, 900 µM-2000 µM, 1500 µM-2500 µM, etc.). In some embodiments, a compound and/or a coating composition may have a minimum inhibitory concentration of less than 10.0 mg/mL, less than 5.0 mg/mL, less than 1.0 mg/mL, less than 0.1 mg/mL, or less than 0.05 mg/mL. In such compositions, antimicrobial properties may not be the primary function of a coating composition.

In some embodiments, a method of coating a surface may include coating an otic surface.

In some embodiments, a method of coating a surface may include coating a dermal surface.

In some embodiments, a method of coating an oral surface may include applying a composition to a surface of an oral surface. The composition may include one or more bridged polycyclic compounds. At least one of the bridged polycyclic compounds may include at least two cyclic groups. At least one cyclic group may be defined in part by quaternary ammonium moieties. The method may include forming an antimicrobial coating over at least a portion of the surface.

The method may include using the composition as a bonding agent, as a resin cement, as a sealant, as a varnish, and/or as a resin.

The oral surface may include at least a portion of a tooth surface, at least a portion of a gum, at least a portion of soft tissue, or at least a portion of a dental fixture. A dental fixture may include a filling, at least a portion of a bridge, or at least a portion of a denture.

The composition may be in the form of a gel, a sealant, a varnish, a resin, and/or a coating.

In some embodiments, a composition may include a coalescing solvent.

In some embodiments, an oral surface may be coated with a coating. The coating may include a chemical composition at least a portion of which forms an antimicrobial coating over at least a portion of the oral surface. The coating may include a chemical composition at least a portion of which forms an antiinflammatory coating over at least a portion of the oral surface. The coating may include a chemical composition at least a portion of which decreases bleeding over at least a portion of the oral surface. The coating may include a chemical composition at least a portion of which decreases inflammation over at least a portion of the oral surface. The coating may include a chemical composition at least a portion of decreases bacterial, viral and/or fungal infection over at least a portion of the oral surface. The coating may include a chemical composition at least a portion of which decreases infection over at least a portion of the oral surface. The chemical composition may include one or more bridged polycyclic compounds. At least one of the bridged polycyclic compounds may include at least two cyclic groups. At least two cyclic groups may be defined in part by quaternary ammonium moieties.

In some embodiments, a method of inhibiting or ameliorating a disease may include administering to a subject an effective amount of a pharmaceutically acceptable formulation comprising a chemical composition as described herein.

In some embodiments, a subject may include a mammal (e.g., canine, feline) and/or a human.

In some embodiments, a method may include administering the pharmaceutically acceptable formulation to a subject parenterally, intracoronary administration, subcutaneously, orally, and/or topically. Topical administration may be in the form of a gel (e.g., a vaginal gel) and/or by self-administration of a topical formula (e.g., in the form of a gel using a one-dose disposable applicator).

In some embodiments, a method may include administering at least two pharmaceutically active agents associated (e.g., covalently bound, noncovalently bound) with a bridged polycyclic compound. In some embodiments, a method may include administering at least two different pharmaceutically active agents. The agents may be coupled to the same and/or different bridged polycyclic compounds.

In some embodiments, a chemical compound may decompose during use, wherein one or more of the products of the decomposition may be more biologically active relative to the chemical compound.

In some embodiments, a method may include administering the pharmaceutically acceptable formulation to a subject in the form of an emulsion.

In some embodiments, at least one pharmaceutically active agent may be bile acid sequestrants, a cholesterol reduction agent, and/or a statin. A statin may include Atorvastatin, Cerivastatin, Ezetimibe, Fluvastatin, Lovastatin, Mevastatin, Niacin, Pitavastatin, Pravastatin, Rosuvastatin, Simvastatin, or derivatives thereof. A statin may include pravastatin, fluvastatin, atorvastatin, or derivatives thereof.

In some embodiments, at least one pharmaceutically active agent may function to inhibit and/or ameliorate otic maladies. A pharmaceutically active agent may include a quinolone or a derivative thereof. A quinolone may include endrofloxicin or derivatives thereof.

In some embodiments, at least one pharmaceutically active agent may function to inhibit and/or ameliorate at least one renal malady (e.g., by binding phosphates). A chemical composition may include a polymeric acid (e.g., a polyethyleneglycol acid (e.g., Methoxypolyethylene glycol 5,000 acetic acid and/or Methoxypolyethylene glycol 5,000 propionic acid)).

In some embodiments, at least one pharmaceutically active agent may function to inhibit and/or ameliorate parrot fever and/or other maladies associated with avians. A pharmaceutically active agent may include a quinolonecarboxylic acid or derivatives thereof. A quinolonecarboxylic acid may include nalidixic acid or derivatives thereof.

In some embodiments, a method may include regulating fat absorption (e.g., intestinal fat absorption). A pharmaceutically active agent may include an MTP inhibitor or derivatives thereof.

In some embodiments, at least one pharmaceutically active agent may function to inhibit and/or ameliorate at least one periodontal disease.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
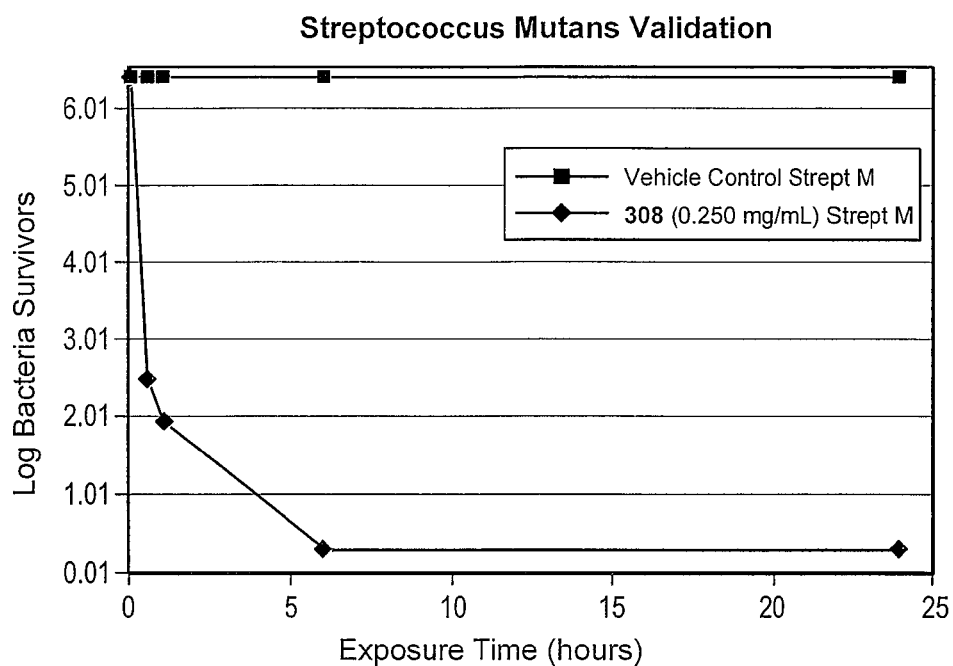
FIG. 1 depicts a graphical representation of time kill assay tests for a bridged polycyclic compound tested against *Streptococcus Mutans*.
Figure 2:
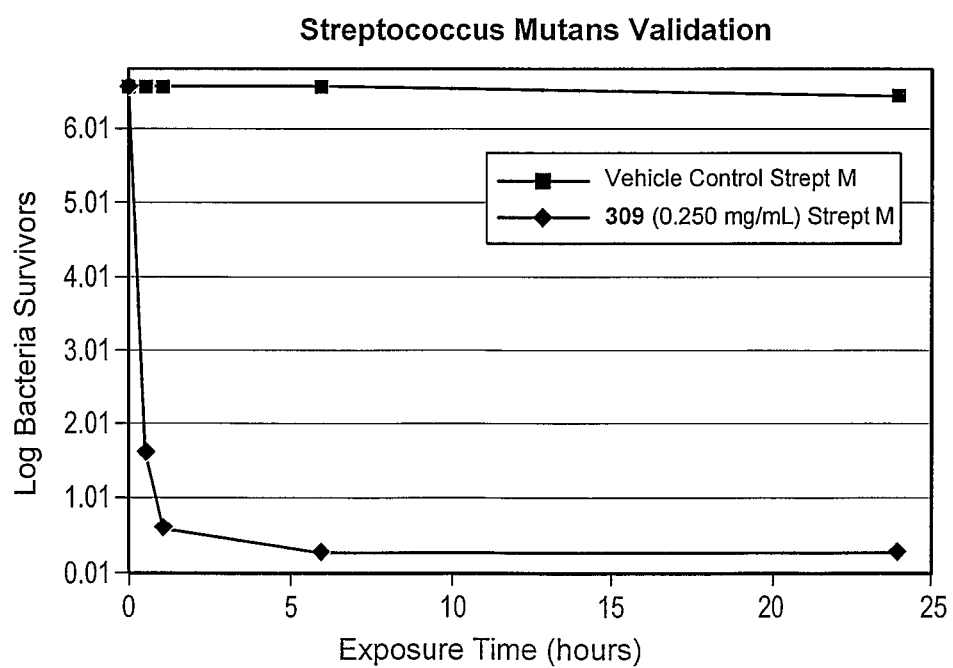
FIG. 2 depicts a graphical representation of time kill assay tests for a bridged polycyclic compound tested against *Streptococcus Mutans*.
Figure 3:
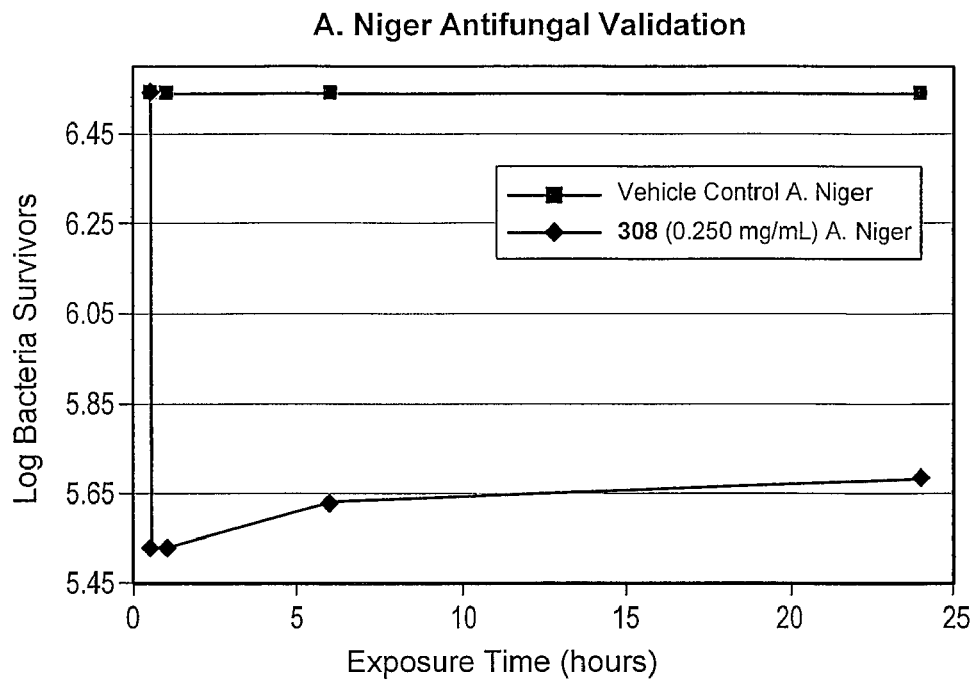
FIG. 3 depicts a graphical representation of time kill assay tests for a bridged polycyclic compound tested against *Aspergillus niger*.
Figure 4:
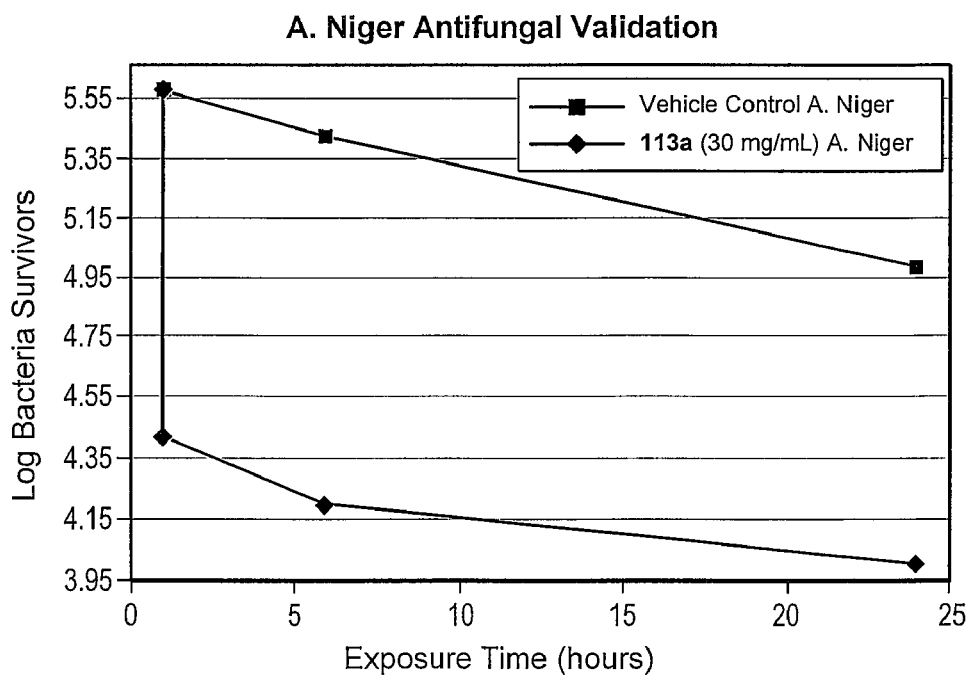
FIG. 4 depicts a graphical representation of time kill assay tests for a bridged polycyclic compound tested against *Aspergillus niger*.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DEFINITIONS

Unless defined otherwise, all technical and scientific terms used herein have the same meaning as commonly understood by one of ordinary skill in the art.

The term "accelerator" as used herein generally refers to a substance that speeds a chemical reaction.

The term "acyl" as used herein generally refers to a carbonyl substituent, —C(O)R, where R is alkyl or substituted alkyl, aryl, or substituted aryl, which may be called an alkanoyl substituent when R is alkyl.

The terms "administration," "administering," or the like, as used herein when used in the context of providing a pharmaceutical, cosmoceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intraperitoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "aldehyde" as used herein generally refers to any of a class of organic compounds containing the group —CHO

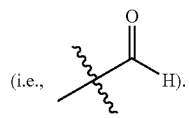

The term "aldehyde forming moiety" as used herein generally refers to any of a class of organic compounds which form an aldehyde in solution or react in an equivalent manner to an aldehyde such that an at least similar chemical product is achieved as would have been achieved with an aldehyde.

The terms "alkenyl" and "alkene" as used herein generally refer to any structure or moiety having the unsaturation C=C. As used herein, the term "alkynyl" generally refers to any structure or moiety having the unsaturation

The term "alkoxy" generally refers to an —OR group, where R is an alkyl, substituted lower alkyl, aryl, substituted aryl. Alkoxy groups include, for example, methoxy, ethoxy, phenoxy, substituted phenoxy, benzyloxy, phenethyloxy, t-butoxy, and others.

The term "alkyl" as used herein generally refers to a chemical substituent containing the monovalent group $C_nH_{2n}$, where n is an integer greater than zero. Alkyl includes a branched or unbranched monovalent hydrocarbon radical. An "n-mC" alkyl or "(nC-mC)alkyl" refers to all alkyl groups containing from n to m carbon atoms. For example, a 1-4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. The term alkyl may include substituted alkyls.

The term "alkyl-aryl" as used herein generally refers to a chemical substituent containing an alkyl group coupled to an aryl group or a substituted aryl group.

The terms "amino" or "amine" as used herein generally refer to a group —NRR', where R and R' may independently include, but are not limited to, hydrogen, alkyl, substituted alkyl, aryl, substituted aryl or acyl.

The terms "amine forming moiety" as used herein generally refers to any of a class of organic compounds which form an amine in solution or react in an equivalent manner to an amine such that an at least similar chemical product is achieved as would have been achieved with an amine.

The terms "amphiphile" or "amphiphilic" as used herein generally refer to a molecule or species which exhibits both hydrophilic and lipophilic character. In general, an amphiphile contains a lipophilic moiety and a hydrophilic moiety. The terms "lipophilic" and "hydrophobic" are interchangeable as used herein. An amphiphile may form a Langmuir film.

Non-limiting examples of hydrophobic groups or moieties include lower alkyl groups, alkyl groups having 6, 7, 8, 9, 10, 11, 12, or more carbon atoms, including alkyl groups with 14-30, or 30 or more carbon atoms, substituted alkyl groups, alkenyl groups, alkynyl groups, aryl groups, substituted aryl groups, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms. The hydrophobic moieties may be linear, branched, or cyclic.

Non-limiting examples of hydrophilic groups or moieties include hydroxyl, methoxy, phenyl, carboxylic acids and salts thereof, methyl, ethyl, and vinyl esters of carboxylic acids, amides, amino, cyano, isocyano, nitrile, ammonium salts, sulfonium salts, phosphonium salts, mono- and di-alkyl substituted amino groups, polypropyleneglycols, polyethylene glycols, glycosyl groups, sugars, epoxy groups, acrylates, sulfonamides, nitro, —OP(O)(OCH$_2$CH$_2$N$^+$RRR)O$^−$, guanidinium, aminate, acrylamide, pyridinium, piperidine, and combinations thereof, wherein each R is independently selected from H or alkyl. Further examples include polymethylene chains substituted with alcohol, carboxylate, acrylate, or methacrylate. Hydrophilic moieties may also include alkyl chains having internal amino or substituted amino groups, for example, internal —NH—, —NC(O)R—, or —NC(O)CH=CH$_2$— groups, wherein R is H or alkyl. Hydrophilic moieties may also include polycaprolactones, polycaprolactone diols, poly(acetic acid)s, poly(vinyl acetates)s, poly(2-vinyl pyridine)s, cellulose esters, cellulose hydroxylethers, poly(L-lysine hydrobromide)s, poly(itaconic acid)s, poly(maleic acid)s, poly(styrenesulfonic acid)s, poly(aniline)s, or poly(vinyl phosphonic acid)s. A hydrophilic group may contain some hydrophobic groups or substituents insofar as the hydrophilic character of the group is not outweighed.

The term "animal" as used herein generally refers to any member of the kingdom Animalia, comprising multicellular organisms that have a well-defined shape and usually limited growth, can move voluntarily, actively acquire food and digest it internally, and have sensory and nervous systems that allow them to respond rapidly to stimuli: some classification schemes also include protozoa and certain other single-celled eukaryotes that have motility and animal-like nutritional modes. Generally the term animal as used herein does not refer to humans.

The term "antiinflammatory" as used herein generally refers to a substance acting to reduce certain signs of inflammation (e.g., swelling, tenderness, fever, and pain).

The term "antimicrobial" as used herein generally refers to a substance capable of destroying or inhibiting the growth of microbes, prevents the development of microbes, and/or inhibits the pathogenic action of microbes as well as viruses, fungi, and bacteria.

The term "aryl" as used herein generally refers to a chemical substituent containing an aromatic group (e.g., phenyl). An aromatic group may be a single aromatic ring or multiple aromatic rings which are fused together, coupled covalently, or coupled to a common group such as a methylene, ethylene, or carbonyl, and includes polynuclear ring structures. An aromatic ring or rings may include, but is not limited to, substituted or unsubstituted phenyl, naphthyl, biphenyl, diphenylmethyl, and benzophenone groups. The term "aryl" includes substituted aryls The term "avian" as used herein generally refers to any of the biological family Aves including a class of vertebrates comprising the birds. Aves are generally characterized by have a complete double circulation, oviparous, reproduction, front limbs peculiarly modified as wings; and they bear feathers. All existing birds have a horny beak, without teeth.

The term "bridged polycyclic compound" as used herein generally refers to a compound that is composed of two or more cyclic systems that share two or more atoms. A cyclic system is formed from a group of atoms which together form a continuous loop. A bridged polycyclic compound may include a bridging atom or group of atoms that connects two or more non-adjacent positions of the same ring. An example of a bridged bicyclic system (i.e., a compound composed of two cyclic systems) with two atoms (atoms "A") common to both cyclic systems is depicted below. One of the linking groups "L" represents a bridging atom or group of atoms.

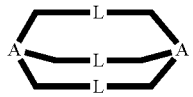

The term "building substrate" as used herein generally refers to a natural or synthetic material used in the construction of a residential or commercial structure.

The term "cancer" as used herein generally refers to any of various malignant neoplasms characterized by the proliferation of anaplastic cells that tend to invade surrounding tissue and metastasize to new body sites.

The term "canine" as used herein generally refers to any of the biological family Canidae including carnivorous mammals including wolves, jackals, foxes, coyote, and the domestic dog.

The term "cavitand" as used herein generally refers to a natural or synthetic molecular compound with enforced cavities large enough to complex complementary compounds or ions. More specifically, a cavitand may be generally defined as a three-dimensional compound that maintains a substantially rigid structure and binds a variety of molecules in the cavities produced by the structure of the three-dimensional compound.

The term "chelating agent or complexing agent" as used herein generally refers to any of various compounds that combine with metals to form chelates.

The term "coalescing agents or solvents" as used herein generally refers to any of various compounds that are used in coatings to promote film formation (e.g., in architectural and industrial latex coating).

The terms "coupling" and "coupled" with respect to molecular moieties or species, atoms, synthons, cyclic compounds, and nanoparticles refers to their attachment or association with other molecular moieties or species, atoms, synthons, cyclic compounds, and nanoparticles. The attachment or association may be specific or non-specific, reversible or non-reversible, the result of chemical reaction, or complexation or charge transfer. The bonds formed by a coupling reaction are often covalent bonds, or polar-covalent bonds, or mixed ionic-covalent bonds, and may sometimes be Coulombic forces, ionic or electrostatic forces or interactions.

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal typically does not extend beyond the boundaries of the crystal. In this case, "long-range ordering" will mean substantial order across at least the majority of the dimension of the nanostructure. In some instances, a nanostructure may bear an oxide or other coating, or may be comprised of a core and at least one shell. In such instances it will be appreciated that the oxide, shell(s), or other coating need not exhibit such ordering (e.g., it may be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, etc., as long as the structure exhibits substantial long range ordering (e.g., order over at least about 80% of the length of at least one axis of the nanostructure or its core). It may be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "cyclic" as used herein generally refers to compounds wherein at least some of the atoms are arranged in a ring or closed-chain structure.

The term "dental compositions" as used herein generally refers to any substances typically associated with any type of dental work and/or in related fields and includes, but is not limited to, dental primers, adhesives, surface sealants, liners, luting cements, varnishes, impression materials, equipment and impression systems, and composite restoratives.

The term "dental fixture" as used herein generally refers to an at least partially synthetic material configured to be positioned in and/or coupled to at least a portion of an oral cavity. For example a dental fixture may include, but is not limited to, a filling, a bridge, a false tooth, a cap, or denture.

The term "disease" as used herein generally refers to a disordered or incorrectly functioning organ, part, structure, or system of the body resulting from the effect of genetic or developmental errors, infection, poisons, nutritional deficiency or imbalance, toxicity, or unfavorable environmental factors; illness; sickness; ailment.

The terms "effective concentration" or "effective amount" as used herein generally refers to a sufficient amount of the pharmaceutically active agent is added to decrease, prevent or inhibit the growth of a virus and/or cancerous growth. The amount will vary for each compound and upon known factors related to the item or use to which the pharmaceutically active agent is applied.

The phrase "enteric coating" as used herein generally refers to a barrier applied to oral medication that controls the location in the digestive system where it is absorbed. Enteric refers to the small intestine, therefore enteric coatings prevent release of medication before it reaches the small intestine. Most enteric coatings work by presenting a surface that is stable at the highly acidic pH found in the stomach, but breaks down rapidly at a less acidic (relatively more basic) pH. For example, they will not dissolve in the acidic juices of the stomach (pH 3), but they will in the higher pH (above pH 5.5) environment present in the small intestine.

The term "feline" as used herein generally refers to any of the biological family Felidae including lithe-bodied carnivorous mammals (as the lion, lynx, and cheetah, as well as the common house cat) having often strikingly patterned fur, comparatively short limbs with soft pads on the feet, usually sharp curved retractile claws, a broad and somewhat rounded head with short but powerful jaws equipped with teeth suited to grasping, tearing, and shearing through flesh, erect ears, and typically eyes with narrow or elliptical pupils and especially adapted for seeing in dim light.

The terms "functionalized" or "functional group" as used herein generally refers to the presence of a reactive chemical moiety or functionality. A functional group may include, but is not limited to, chemical groups, biochemical groups, organic groups, inorganic groups, organometallic groups, aryl groups, heteroaryl groups, cyclic hydrocarbon groups, amino (—NH$_2$), hydroxyl (—OH), cyano

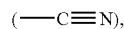

nitro (NO$_2$), carboxyl (—COOH), formyl (—CHO), keto (—CH$_2$C(O)CH$_2$—), ether (—CH$_2$—O—CH$_2$—), thioether (—CH$_2$—S—CH$_2$—), alkenyl (—C=C—), alkynyl,

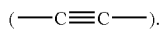

epoxy

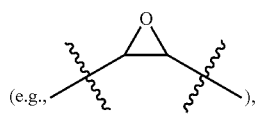

metalloids (functionality containing Si and/or B) and halo (F, Cl, Br, and I) groups. In some embodiments, the functional group is an organic group.

The term "gram-negative bacteria" or "gram-negative bacterium" as used herein generally refers to bacteria which have been classified by the Gram stain as having a red stain. Gram-negative bacteria have thin walled cell membranes consisting of a single layer of peptidoglycan and an outer layer of lipopolysaccharide, lipoprotein, and phospholipid. Exemplary organisms include, but are not limited to, Enterobacteriaceae consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary gram-negative organisms not in the family Enterobacteriaceae include, but are not limited to, *Pseudomonas aeruginosa, Stenotrophomonas maltophilia, Burkholderia, Cepacia, Gardenerella, Vaginalis*, and *Acinetobacter* species.

The term "gram-positive bacteria" or "gram-positive bacterium" as used herein refers to bacteria, which have been classified using the Gram stain as having a blue stain. Gram-positive bacteria have a thick cell membrane consisting of multiple layers of peptidoglycan and an outside layer of teichoic acid. Exemplary organisms include, but are not limited to, *Staphylococcus aureus*, coagulase-negative staphylococci, streptococci, enterococci, *corynebacteria*, and *Bacillus* species.

The term "heteroaryl" generally refers to a completely unsaturated heterocycle.

The term "heterocycle" as used herein generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogues of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, and xanthenyl. Also included are fused ring and spiro compounds containing, for example, the above heterocycles.

The term "initiator" as used herein generally refers to a substance that initiates a chemical reaction.

The term "ion" as used herein generally refers to an atom(s), radical, or molecule(s) that has lost or gained one or more electrons and has thus acquired an electric charge.

The terms "in need of treatment" or "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The term "malady" as used herein generally refers to any disorder or disease of the body or any undesirable or disordered condition including, but not limited to, illness, sickness, affliction, complaint, ailment, indisposition, virus, disease, fungus, infection, disease, etc.

The term "mammal" as used herein generally refers to any vertebrate of the class Mammalia, having the body more or less covered with hair, nourishing the young with milk from the mammary glands, and, with the exception of the egg-laying monotremes, giving birth to live young. Generally the term mammal as used herein does not refer to humans.

The term "matrix" generally refers to a material, often a polymeric material and/or a prepolymeric material, into which a second material (e.g., a nanostructure) is embedded, surrounded, or otherwise associated. A matrix is typically composed of one or more monomers, but may include other matrix components/constituents. Often the matrix constituents include one or more "addressable" components or complementary binding pairs, that optionally promote assembly and/or cross-linkage of the matrix.

The term "medical device" as used herein generally refers to a device used which pertains to treating or determining the state of one's health. Medical devices are any article that contacts subjects or are used in health care, and may be for use either internally or externally.

The term "microbe" as used herein generally refers to a minute life form; a microorganism. In some embodiments, a microbe may include a bacterium that causes disease.

The term "modulate," as used herein, generally refers to a change or an alteration in the magnitude of a be used herein to biological parameter such as, for example, foci formation, tumorigenic or neoplastic potential, apoptosis, growth kinetics, expression of one or more genes or proteins of interest, metabolism, oxidative stress, replicative status, intercellular communication, or the like. "Modulation" may refer to a net increase or a net decrease in the biological parameter.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

The terms "monofunctional", "bifunctional", "trifunctional", and "multifunctional" generally refers to a number of attachment sites a particular compound, molecule, atom, etc. may include (monofunctional having one site, bifunctional having two sites, trifunctional having three sites, and multifunctional having more than one site).

The term "nanocrystal" as used herein generally refers to a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 mm. The region or characteristic dimension may be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, etc. Nanostructures may be substantially homogeneous in material properties, or in certain embodiments may be heterogeneous (e.g., heterostructures). Optionally, a nanocrystal may comprise one or more surface ligands (e.g., surfactants). The nanocrystal is optionally substantially single crystal in structure (a "single crystal nanostructure" or a "monocrystalline nanostructure"). Nanostructures may be fabricated from essentially any convenient material or material, the nanostructure may be prepared from an inorganic material, e.g., an inorganic conductive or semiconductive material. A conductive or semi-conductive nanostructure often displays 1-dimensional quantum confinement, e.g., an electron may often travel along only one dimension of the structure. Nanocrystals may be substantially homogeneous in material properties, or in certain embodiments may be heterogeneous (e.g., heterostructures). The term "nanocrystal" is intended to encompass substantially monocrystalline nanostructures comprising various defects, stacking faults, atomic substitutions, etc., as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals may be fabricated from essentially any convenient material or materials.

The terms "nanostructure" or "nanoparticle" are used herein to generally refer to a structure having at least one region or characteristic dimension with a dimension of less than about 500 nm, e.g., less than about 200 nm, less than about 100 nm, less than about 50 nm, or even less than about 20 nm. The region or characteristic dimension may be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), etc. Nanostructures may be substantially homogeneous in material properties, or in certain embodiments may be heterogeneous (e.g., heterostructures). Nanostructures may be, e.g., substantially crystalline, substantially monocrystalline, polycrystalline, amorphous, or a combination thereof. In one aspect, each of the three dimensions of the nanostructure has a dimension of less than about 500 nm, e.g., less than about 200 nm, less than about 100 nm, less than about 50 nm, or even less than about 20 nm. Nanostructures may comprise one or more surface ligands (e.g., surfactants).

The term "nonsystemic" as used herein, generally refers to a compound or composition which is not substantially absorbable into the bloodstream of a human or animal.

The terms "oligomeric" and "polymeric" as used herein are generally used interchangeably herein to generally refer to multimeric structures having more than one component monomer or subunit.

The term "organ" is used herein to generally refer to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

The term "opthalmic" as used herein generally is of or relating to or resembling the eye; "ocular muscles"; "an ocular organ"; "ocular diseases".

The term "oral surface" as used herein generally refers to a portion of the mouth and/or something positioned in and/or coupled to a portion of the mouth. For example an oral surface may include, but is not limited to, at least a portion of a tooth, at least a portion of the gum, at least a portion of the tongue, or at least a portion of a dental fixture (e.g., a filling, a bridge, a cap a false tooth).

The term "otic" as used herein generally is of, relating to, or located near the ear; auricular.

The term "pharmaceutically acceptable salts" as used herein generally includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The term "pharmaceutically active agent" as used herein generally refers to a drug or other substance that has therapeutic value to a living organism including without limitation antithrombotics, anticoagulants, antiplatelet agents, thrombolytics, antiproliferatives, antiviral, antitumor, anticancer, antimicrobial, antifungal, anti-inflammatories, agents that inhibit restenosis, smooth muscle cell inhibitors, antibiotics, and the like, and mixtures thereof.

Terms such as "pharmaceutical composition," "pharmaceutical formulation," "pharmaceutical preparation," or the like, are used herein to generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

The term "pharmacologically inert," as used herein, generally refers to a compound, additive, binder, vehicle, and the like, that is substantially free of any pharmacologic or "drug-like" activity.

The term "polycyclic," as used herein, generally refers to a chemical compound having two or more atomic rings in a molecule. Steroids are polycyclic compounds. The term "polymerizable compound," as used herein, generally refers to a chemical compound, substituent or moiety capable of undergoing a self-polymerization and/or co-polymerization reaction (e.g., vinyl derivatives, butadienes, trienes, tetraenes, dialkenes, acetylenes, diacetylenes, styrene derivatives).

By "prophylactically effective amount" is meant an amount of a pharmaceutical composition that will substantially prevent, delay or reduce the risk of occurrence of the biological or physiological event in a cell, a tissue, a system, animal or human that is being sought by a researcher, veterinarian, physician or other caregiver.

The term "quaternary ammonium moiety," as used herein, generally refers to a tetravalent charged nitrogen (e.g., $N^+R^3_4$).

The terms "R"" in a chemical formula refer to a hydrogen or a functional group, each independently selected, unless stated otherwise. In some embodiments, the functional group may be an organic group. In some embodiments, the functional group may be an alkyl group. In some embodiments, the functional group may be a hydrophobic or hydrophilic group.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "subject" as used herein generally refers to a mammal (e.g., felines, canines), and in particular to a human.

The term "sealant," as used herein, generally refers to any of various liquids, paints, chemicals, or soft substances that may be applied to a surface or circulated through a system of pipes or the like, drying to form a hard, substantially watertight coating. When used in the context of dentistry sealant generally refers to any of several transparent synthetic resins applied to the chewing surfaces of an oral cavity as a preventive measure against tooth decay in the occlusal pits and fissures.

The term "statin," as used herein, generally refers to any of a class of lipid-lowering drugs that reduce serum cholesterol levels by, for example, inhibiting a key enzyme involved in the biosynthesis of cholesterol.

The term "substituted alkyl" as used herein generally refers to an alkyl group with an additional group or groups attached to any carbon of the alkyl group. Substituent groups may include one or more functional groups such as alkyl, lower alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and other organic groups.

The term "substituted alkyl-aryl" as used herein generally refers to an alkyl-aryl group with an additional group or groups attached to any carbon of the alkyl-aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted aryl" as used herein generally refers to an aryl group with an additional group or groups attached to any carbon of the aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted heterocycle" as used herein generally refers to a heterocyclic group with an additional group or groups attached to any element of the heterocyclic group. Additional groups may include one or more functional groups such as lower alkyl, aryl, acyl, halogen, alkylhalos, hydroxy, amino, alkoxy, alkylamino, acylamino, acyloxy, aryloxy, aryloxyalkyl, thioether, heterocycles, both saturated and unsaturated cyclic hydrocarbons which are fused to the heterocyclic ring(s), coupled covalently or coupled to a common group such as a methylene or ethylene group, or a carbonyl coupling group such as in cyclohexyl phenyl ketone, and others.

The term "substrate" as used herein generally refers to a body or base layer or material (e.g., onto which other layers are deposited).

The phrase "therapeutically effective amount" generally refers to an amount of a drug or pharmaceutical composition that will elicit at least one desired biological or physiological response of a cell, a tissue, a system, animal or human that is being sought by a researcher, veterinarian, physician or other caregiver.

The term "thioether" as used herein generally refers to the general structure R—S—R' in which R and R' are the same or different and may be alkyl, aryl or heterocyclic groups. The group —SH may also be referred to as "sulfhydryl" or "thiol" or "mercapto."

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

The term "topical" as used herein generally is of, pertaining to, or applied externally to a particular part of the body; local.

The term "virus" as used herein generally refers to an ultramicroscopic (20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

Bridged Polycyclic Compounds

New antimicrobials are required to combat the new antimicrobial resistant microbes. New antimicrobials may be effective verses microbes which are currently resistant to currently known antimicrobials. New antimicrobials may resist leaching off into the environment beyond a predetermined amount to inhibit polluting the environment unnecessarily (which may concurrently increase the occurrence of antimicrobial resistant microbes from overexposure of antimicrobials).

One strategy for combating antimicrobial resistant organisms is by modifying known antimicrobials to increase their effectiveness. In some embodiments, quaternary ammonium compounds may be modified to increase their effectiveness. It is typically thought that quaternary ammonium compounds denature the proteins of the bacterial or fungal cell, affect the metabolic reactions of the cell and allow vital substances to leak out of the cell, finally causing death. In addition, quaternary ammonium compounds are not known to be toxic towards higher forms of life (e.g., humans).

One of the main considerations in examining the mode of action is the characterization of quaternary ammonium compounds as cationic surfactants. This class of chemical reduces the surface tension at interfaces, and is attracted to negatively charged surfaces, including microorganisms. Quaternary ammonium compounds denature the proteins of the bacterial or fungal cell, affect the metabolic reactions of the cell and allow vital substances to leak out of the cell, resulting in the death of the cell.

Most uses of quaternary ammonium compounds as antimicrobials involve formulations of disinfectants and sanitizes which are not bound to a surface, resulting in effluent stream pollution and contamination. They are simply wetted onto the surface such as in disinfecting wipes which are primarily ammonium salts as their liquid active ingredient. When they are incorporated into surfaces they are not crosslinked but are allowed to float to the surface thereby becoming depleted over time the same way silver and triclosan are incorporated in plastics. Coupling quaternary ammonium compounds to a surface or formation within a polymer matrix may inherently reduce the effectiveness of the quaternary ammonium compounds, by decreasing the accessibility of microbes to the most active cationic portion of the molecule. Increasing accessibility to the quaternary ammonium compounds within a surface coating or with any use increases the effectiveness of the quaternary ammonium compound.

In some embodiments, the effectiveness of an antimicrobial (e.g., quaternary ammonium compound) may be increased by coupling the antimicrobial within or on a curved surface, where the curved surface is on a molecular scale. For example, a curved surface may be created using nanoparticles (e.g., spherical nanoparticles). Nanoparticles may incorporate into their structure antimicrobial compounds with greater exposed surface area due to the curved surface of the nanoparticle.

In some embodiments, a compound may include a nanoparticle. The nanoparticle may include a bridged polycyclic compound. A compound may be formed using self-assembly techniques and principles. A compound may be formed from portions which are themselves antimicrobial (e.g., quaternary ammonium compounds). A compound may bind moieties to at least portions of itself which have, for example, antimicrobial properties.

In some embodiments, a protective coating composition may include a compound. A compound may be a bridged polycyclic compound. A bridged polycyclic compound may be a cavitand. Portions of the bridged polycyclic compound may include two or more quaternary ammonium moieties. The protective coating composition may be antimicrobial.

New carrier agents are required to more effectively deliver existing and future pharmaceutical agents.

One strategy for more effectively delivering pharmaceutical agents is to couple a multitude of pharmaceutical agents (e.g., a single type of agent or a combination of different agents) to a single molecular entity.

In some embodiments, the effectiveness of a pharmaceutically active agent may be increased by coupling the agent within or on a curved surface, where the curved surface is on a molecular scale. For example, a curved surface may be created using nanoparticles (e.g., spherical nanoparticles). Nanoparticles may incorporate into their structure pharmaceutically active agent with greater exposed surface area due to the curved surface of the nanoparticle.

In some embodiments, a compound may include a nanoparticle. The nanoparticle may include a bridged polycyclic compound. A compound may be formed using self-assembly techniques and principles. A compound may be formed from portions which are pharmaceutically active agents. A compound may bind moieties to at least portions of itself which are pharmaceutically active agents.

In some embodiments, a composition may include one or more bridged polycyclic compounds. At least one of the bridged polycyclic compounds may include at least two cyclic groups. A general example of a bridged polycyclic compound including only two cyclic groups may include, but is not limited to, a compound 100 having a general structure

In some embodiments, at least two cyclic groups may be defined in part by quaternary ammonium moieties, by the nitrogen of the quaternary ammonium moiety comprising one of the atoms which forms a part of the cyclic structure itself. For example, a cyclic structure which is formed at least in part by a quaternary ammonium moiety may include, but is not limited to structure 101

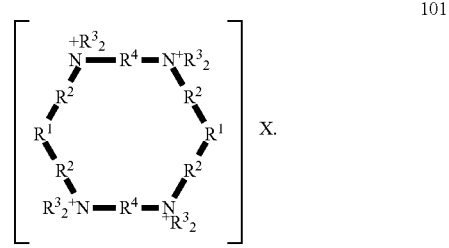

Structure 101 is an example of quaternary ammonium moieties defining at least in part a cyclic group, however, compound 101 is not an example of a polycyclic compound and compound 101 is not an example of a bridged polycyclic compound.

In some embodiments, a bridged polycyclic compound may include at least two quaternary ammonium moieties, at least three quaternary ammonium moieties, at least four quaternary ammonium moieties, at least five quaternary ammonium moieties, at least six quaternary ammonium moieties, at least seven quaternary ammonium moieties, or at least eight quaternary ammonium moieties.

In some embodiments, a compound 100 may have a general structure

Compound 100 may be formed by coupling a trifunctional corner unit A with a bifunctional linker unit L as depicted in Scheme 2.

Scheme 2. Schematic depiction of the formation of compound 100.

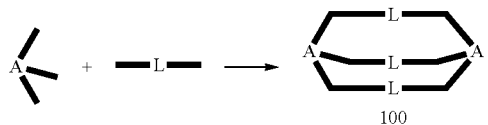

Scheme 2 should not be used to limit the disclosure set forth herein. Corner unit A may include multiple dentate linkers other than the one depicted in Scheme 2 (e.g., a trifunctional linker A is depicted in Scheme 2) including, but not limited to, tetrafunctional (e.g., compound 100a) etc. In some embodiments, a corner unit A may be coupled to a linker unit L in any multitude of ways known to one skilled in the art.

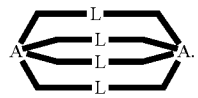

100a

In some embodiments, a compound 100c may have a general structure

100c

Compound 100c may be a bridged polycyclic compound. In some embodiments, Z may include at least one bridge. Bridge Z may couple 2 non adjacent atoms.

In some embodiments, at least one of the bridges is —$R^2$—$N^+R^3{}_2$—$R^4$—$N^+R^3$—$R^2$—, such that each bridge independently couples A to A. In some embodiments, at least one of the bridges may be —$R^2$—$NR^3$—$R^4$—$N^+R^3{}_2$—$R^2$—. Each bridge may independently couple A to A. In some embodiments, at least one of the bridges may be —$R^2$—$NR^3$—$R^4$—$NR^3$—$R^2$—. Each bridge may independently couple A to A. In some embodiments, at least one of the bridges may be —$R^2$—N=$R^4$=N—$R^2$—. Each bridge may independently couple A to A.

For example when Z is 1 compound 100c may be a compound 100 having a general structure

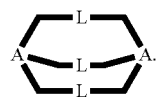

100

When, for example, Z is 2 a compound 100c may be a compound 100a having a general structure

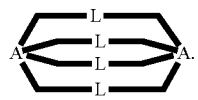

100a

When, for example, Z is 3 a compound 100c may be a compound 100d having a general structure

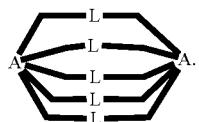

100d

In some embodiments, a compound may include a bridged polycyclic compound formed from two corner units (e.g., compound 100b). Compound 100b may be formed by coupling a multifunctional (e.g., trifunctional) corner unit A with a second multifunctional (e.g., trifunctional) corner unit A as depicted in Scheme 2a.

Scheme 2a. Schematic depiction of the formation of compound 100b.

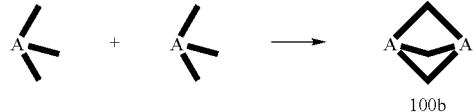

100b

In some embodiments, a compound 102 may have a general structure

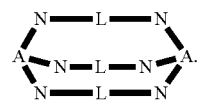

102

Compound 102 may include a moiety coupling corner unit A with linker unit L, the moiety including a nitrogen.

In some embodiments, a compound 103 may have a general structure

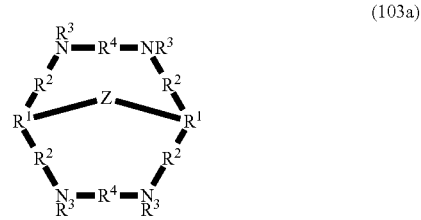

(103a)

In some embodiments, $R^1$ may be independently alkyl, substituted alkyl, aryl, substituted alkyl, N,$N^+R^3$, heterocycle, or substituted heterocycle. $R^2$ may be independently alkyl, substituted alkyl, aryl, substituted aryl, heterocycle, substituted heterocycle, covalent bond, or alkene. $R^3$ may be independently a pharmaceutically active agent, alkyl, substituted alkyl, aryl, substituted aryl, heterocycle, substituted heterocycle, alkene, ether, PEG, contains boron, or PEI. $R^4$ may be independently alkyl, substituted alkyl, aryl, substituted aryl, $N^+R^3$, heterocycle, substituted heterocycle, alkyl ether, PEG, PEI, ether, or alkene. $R^4$ may independently include amide, alcohol, ester, sulfonamide, or sulfanilamide. $R^4$ may be independently alkyl, substituted alkyl, aryl, substituted aryl, heterocycle, substituted heterocycle, ether, amide, alcohol, ester, sulfonamide, sulfanilamide, or alkene. Z may include at least one bridge.

For example when Z is 1 compound 103a may be a compound 104b having a general structure

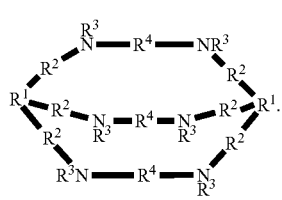

104b

When, for example, Z is 2 a compound 103a may be a compound 104c having a general structure

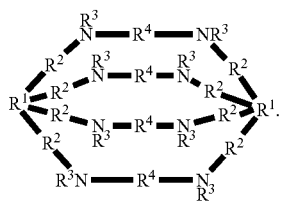

104c

In some embodiments, a pharmaceutically active agent may include any agent which inhibits or ameliorates a disease.

In some embodiments, a pharmaceutically active agent may include antiviral agents. Examples of antiviral agents may include alkyl sulfonic acid groups; supfoacetamide groups; sulfosuccinamic acid groups; N-sulfoalkyl succinamide groups, such as N-(2-sulfoethyl)succinamide groups; aryl or heteroaryl thioureas substituted with one or more sulfonic acid groups, such as 4-sulfophenylthiourea groups, 3,6-disulfonapthylthiourea groups, 4-sulfonapthylthiourea groups, 3,5-disulfophenyl thiourea groups and 3,6,8-trisulfonapthylthiourea groups; aryl or heteroaryl amides substituted with one or more sulfonic acid, sulfoalkyl, sulfoalkoxy, sulfoalkylamino or sulfoalkylthio groups, such as 4-(sulfomethyl)benzamide groups or 4-sulfobenzamide groups; aryl or heteroaryl alkanamides substituted with one or more sulfonic acid groups, such as N-(4-sulfophenyl) propanamide groups; aryl or heteroaryl ureas substituted with one or more sulfonic acid groups, such as 4-sulfophenyl urea groups; N,N,N-trimethyl derivatives of amino acids, such as N,N,N-trimethylglycinamine groups; aryl or heteroarylamides substituted with one or more trialkylamino, trialkylaminoalkyl, trialkylaminoalkyloxy, trialkylaminoalkylamino or trialkylaminoalkylthio groups, such as 4-trimethylammonium benzamide or 4-(trimethylammonium methyl)benzamide groups; N-(2-acetoxyethyl)-N,N-(dimethylammonium)methylcarboxamide groups; guanidino groups; 4-carboxy-3-hydroxybenzylamine groups; or macrocyclic polyamino groups containing one or more macrocyclic rings connected through an alkyl or aryl spacer moiety to the terminal group of the dendrimer, such as 4-([1,4,8,11-terayclotetradecane]methyl)benzamide groups. Antiviral agents may include sulfonate derivatives.

In some embodiments, antiviral agents may include acyclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, desciclovir, deoxyacyclovir, edoxuidine, enviroxime, fiacitabine, foscamet, fialuridine, fluorothymidine, floxuridine, ganciclovir, hypericin, interferon, interleukin, isethionate, idoxuridine, nevirapine, pentamidine, ribavirin, rimantadine, stavirdine, sargramostin, suramin, trichosanthin, trifluorothymidine, tribromothymidine, trichlorothymidine, trisodium phosphomonoformate, vidarabine, zidoviridine, zalcitabine and 3-azido-3-deoxythymidine, and pharmaceutically acceptable salts, analogs, prodrugs or codrugs thereof.

In some embodiments, a pharmaceutically active agent may include anticancer agents. Anticancer agents may include derivatives of the drug Methotrexate. Anticancer agents may include derivatives of the drug Doxorubicin. Anticancer agents may include guanidine derivatives.

In some embodiments, anticancer agents may include taxoids, taxines or taxanes like paclitaxel and docetaxel; phodophyllotoxins; camptothecins like camptothecin, 9-nitrocamptothecin, 9-aminocamptothecin, camptothecin-11, topodecane; anthracyclines like doxorubicin, epirubicin, aclarubicin, idarubicin, pyrarubicin; vinca alkaloids like vincristine, vinorelbine, vindesine, vintripole, vinsaltine; eposilones, platinum, etoposide, methotrexate, carmustine, 5-fluorouracil, retinoic acid, retinol, tamoxifen, mitomycin B, mitomycin C, amonafide, illudin S, etc.

In some embodiments, anticancer agents may include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83-HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride. flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

In some embodiments, a pharmaceutically active agent may include an ovarian cancer agent, a breast cancer agent, and/or a prostate cancer agent.

In some embodiments, a pharmaceutically active agent may include a cholesterol reduction agent.

In some embodiments, a pharmaceutically active agent may include a lipase inhibitor agent.

In some embodiments, a pharmaceutically active agent may include a bile acid sequestrant agent.

In some embodiments, a pharmaceutically active agent may include a cytomegalovirus agent.

In some embodiments, a pharmaceutically active agent may include a periodontal disease agent.

In some embodiments, a pharmaceutically active agent may include agents which effective in treating, inhibiting, and/or ameliorating HIV/AIDS, HIV1, HIV2, Hepatitis B virus, Hepatitis C virus, Bovine Viral Diarrhoea Virus, Influenza, Human Influenza Virus B, Rhinovirus, Human Parainfluenza Virus, Respiratory Syncytial Virus (RSV), Varicella Zoster Virus (VSV), HSV-2 (genital herpes), Herpes Labialis, Human Cytomegalovirus (CMV), Epstein Bar Virus (EBV), Human Papilloma Virus (HPV), Adenovirus, Herpes Simplex Virus type 1, Herpes Simplex Virus type 2, Measles Virus, Bacterial Vaginosis (BV), pneumonia, Dengue virus, and Vesicular Stomatitis Virus (VSV).

In some embodiments, a pharmaceutically active agent may include a topical agent, a dermatological agent, and/or an antifungal agent.

In some embodiments, a pharmaceutically active dermatological agent may be active for Methacillin-resistant *Staphylococcus aureus* (MRSA), oxacillin-resistant *Staphylococcus aureus* (ORSA), rosacea, acne, and/or onychomycosis.

In some embodiments, a pharmaceutically active agent may include anti-inflammatory agents. Anti-inflammatory agents may include Nonsteroidal anti-inflammatory drugs (NSAIDs). NSAIDS may include aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen (Tylenol®), and mixtures thereof. Anti-inflammatory agents may include COX-2 inhibitors. COX-2 inhibitors may include nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof. Anti-inflammatory agents may include glucocorticoids. Glucocorticoids may include hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof; and mixtures thereof.

In some embodiments, a pharmaceutically active agent may include antimicrobial agents and/or an anti-bacterial agent.

In some embodiments, a pharmaceutically active agent may include antiviral agents and/or a contraceptive agent. Surveys show that there is substantial demand in North America and Europe for such a product with an estimated billion dollar market for STI prevention products in the developed world.

In some embodiments, bridged polycyclic compounds and/or salts (e.g., cationic) thereof may absorb lipids and remove them from the body, for example, effectively lowering cholesterol or decreasing fat uptake by the body (e.g., a gluconate salt of a bridged polycyclic compound). In some embodiments, bridged polycyclic compounds may include compounds associated with the bridged polycyclic compound which also absorb lipids and remove them from the body (effectively lowering cholesterol or decreasing fat uptake by the body).

In some embodiments, bridged polycyclic compounds may be associated with Statin derivatives (e.g., Lipitor, Orlistat). Statins form a class of hypolipidemic drugs used to lower cholesterol levels in people with or at risk of cardiovascular disease. Statins are believed to lower cholesterol by inhibiting the enzyme HMG-CoA reductase (the rate-limiting enzyme of the mevalonate pathway of cholesterol synthesis). Inhibition of HMG-CoA reductase in the liver stimulates LDL receptors. Stimulation of LDL receptors may result in an increased clearance of low-density lipoprotein (LDL) from the bloodstream and a decrease in blood cholesterol levels. Statins may include Atoivastatin, Cerivastatin, Ezetimibe, Fluvastatin, Lovastatin, Mevastatin, Niacin, Pitavastatin, Pravastatin, Rosuvastatin, and Simvastatin. Statins may be coupled with bridged polycylic compounds described herein. In some embodiments, statins which exist as an acid (e.g., pravastatin, fluvastatin, atorvastatin) may be directly coupled to a bridged polycyclic compound (e.g., to an amine forming a salt). Some statins may be (e.g., lactone statins) converted to an acid form (as described in Deng-Jye Yang and Lucy Sun Hwang, Journal of Chromatography A Volume 1119, Issues 1-2, 2006, pg. 277-284, which is incorporated by reference as if fully set forth herein) and coupled to bridged polycyclic compounds.

In some embodiments, bridged polycyclic compounds may be associated with microsomal triglyceride transfer protein (MTP) inhibitors, Statin derivatives (e.g., Lipitor, Orlistat), or anti-hyperlipidemic medication (e.g., ezetimibe). In some embodiments, MTP inhibitors, Triacylglycerol Synthesis inhibitors (e.g., niacin), Statins, etc. may be incorporated as counterions forming salts of bridged polycyclic compounds. This may provide an additional benefit of a slow release mechanism for the MTP inhibitor or Statins (associated with the bridged polycyclic compounds as an anionic salt upon protonation (e.g., using the carboxylic acid moiety of the MTP inhibitor and/or statin on the amine of the bridged polycyclic compound); e.g., niacin, butyric acid and/or atorvastatin (Lipitor), etc.).

This may be advantageous as the immediate-release form of nicotinic acid (niacin) is safe for long-term use. However, for example, the triacylglycerol synthesis inhibitor nicotinic acid (niacin) has frequent side effects. Side effects of niacin may include: sudden blushing or redness of the face (flushing), which is more common with the immediate-release forms of nicotinic acid; itching; liver problems (hepatotoxicity), especially with the sustained-release form; high blood sugar (hyperglycemia); and too much uric acid in the blood (hyperglycemia), excess uric acid in the blood can lead to gout, gastrointestinal problems (e.g., upset stomach, gas, nausea, vomiting, and diarrhea), dizziness, lightheadedness, or a fast or slow heartbeat.

Further descriptions of MTP inhibitors for lowering cholesterol, which may be used in combination with bridged polycyclic compounds described herein, are included in U.S. Pat. No. 6,562,329 to Hadvary et al., which is incorporated by reference as if fully set forth herein. Descriptions of MTP and its mechanisms in lipoprotein assembly may be found in Marcil, V. et. al. J. Nutr. 2003, 133: 2180-2183, which is incorporated by reference as if fully set forth herein.

In some embodiments, bridged polycyclic compounds may remove toxic substances from the body (i.e. metals and other toxins) by virtue of the amine cage encapsulating the toxins. Amine functionalized cryptands are well know for binding and/or removal of metals from toxic waste as well as metal and/or atom binding for MRI imaging. For example, lead poisoning (and other toxic metals) is a common problem for children, adults, mammals and avian species.

In some embodiments, bridged polycyclic compounds may include butyrate as a counter ion to the bridged polycyclic compounds. Butyrate may function to inhibit MTP lipid aggregation mechanism and lower cholesterol. The bridged polycyclic compound may function to absorb and remove lipids (LDL) from the body. Descriptions of cholesterol reduction using, for example, butyrate may be found in Hussain, M. M. et. al. Journal of Lipid Research, 2003, vol 44, 22-32, which is incorporated by reference as if fully set forth herein.

In some embodiments, bridged polycyclic compounds may be combined with MTP inhibitors (e.g., butyric acid). MTP inhibitors may function to lower cholesterol as previously discussed. However, MTP inhibitors may be used in combination with bridged polycyclic compounds to regulate intestinal fat absorption. Gastrointestinal lipases are responsible for breaking down ingested fat (gastric lipase, carboxylester lipase, pancreatic lipase). As a consequence of this, unabsorbed fat may be excreted. Pancreatic lipase is one of the enzymes for the hydrolysis of dietary triglycerides. Triglycerides that have escaped hydrolysis may not be absorbed in the intestine. In vitro, MTP catalyzes the transport of lipid molecules between phospholipid membranes. It plays a similar role in vivo, and thus plays a role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. The ability of MTP to catalyze the transport of triglycerides (TG) between membranes is consistent with this hypothesis, and suggests that MTP may catalyze the transport of TG from its site of synthesis in the endoplasmic reticulum (ER) membrane to nascent lipoprotein particles within the lumen of the ER. Pharmacological studies with human patients have demonstrated potent inhibition of fat absorption. Reduction of body weight has been achieved using lipase inhibitors. However, in a subgroup of the patients, unpleasant gastrointestinal side effects such as oily spotting, fatty/oily stools, fecal urgency, increased defecation and fecal incontinence are observed. Accordingly, there is a need in the art for lipase inhibiting compositions that minimize or suppress the side effects caused by inhibitors of digestive lipases. Combining MTP inhibitors with bridged polycyclic compounds may slow the absorption (e.g., by slowing the release of MTP inhibitors in a body) of the inhibitors reducing some of these unpleasant side effects. MTP inhibitors and their side effects are more fully described in U.S. Pat. Nos. 6,756,364 to Barbier et al. and 5,990,110 to Firestone, which are incorporated by reference as if fully set forth herein.

In some embodiments, bridged polycyclic compounds may be employed as a phosphate binder to inhibit and/or ameliorate renal disease (e.g., kidney disease). Bridged polycyclic compounds (and specifically their salts) may be used as a phosphate binder. Bridged polycyclic compounds may be combined with polymeric acids to form salts. These resulting salts may function to absorb water and/or bind salts which kidney disease patients typically need dialysis for. Polymeric acids may include polyethyleneglycol acids (e.g., Methoxypolyethylene glycol 5,000 acetic acid, Methoxypolyethylene glycol 5,000 propionic acid) to absorb water as they pass through a body. Polymers capable of absorbing water may function to ameliorate Renal disease and related diseases described herein. Hydrophilic compounds known to one skilled in the art may be coupled to and/or associated with polymerized bridged polycyclic compounds. Further descriptions of Renal disease and related disease, as well as phosphate binding polymers which may be used in combination with bridged polycyclic compounds are included in U.S. Pat. Nos. 5,496,545; 5,667,775; and 6,858,203 to Holmes-Farley et al., which are incorporated by reference as if fully set forth herein. Further descriptions of Renal disease and related disease as well as in vivo water absorbent polymers for relief of over-hydrated renal disease patients are included in U.S. Pat. Nos. 6,908,609 to Simon et al., 6,908,609 to which is incorporated by reference as if fully set forth herein.

In some embodiments, an example of a compound 104b may include compound 10 having a general structure

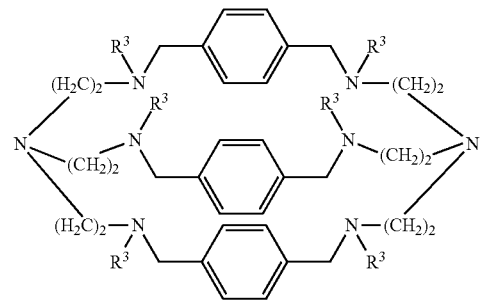

where

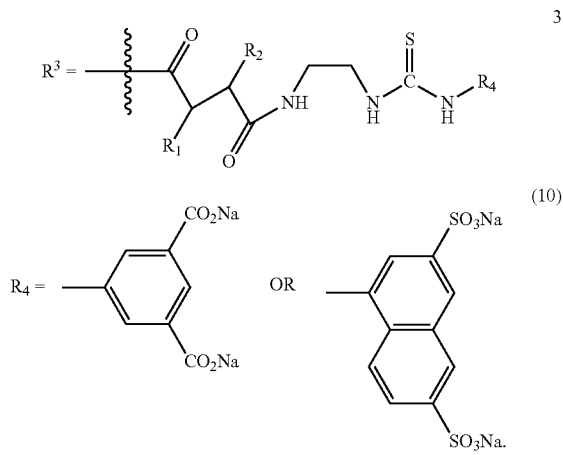

(10)

In some embodiments, an example of a compound 104b may include compound II having a general structure

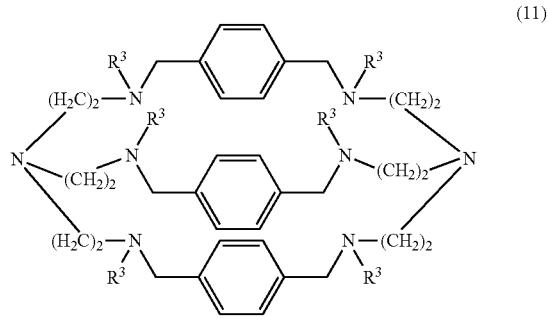

(11)

-continued

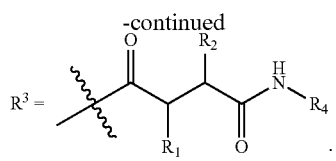

$R^4$ may be any number of pharmaceutically active agents, however, the agents depicted in compounds 10 and 11 are antiviral in nature.

In some embodiments, an example of a compound 104b may include compound 15 having a general structure (15)

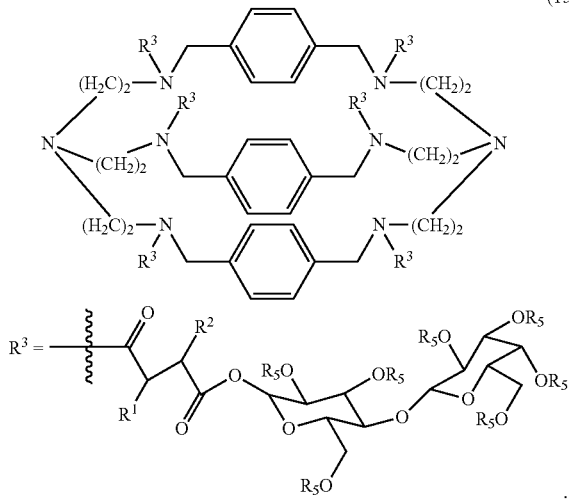

The agents (i.e., Acylated Lactose Imidate) depicted in compound 15 are anti-inflammatory in nature.

In some embodiments, an example of a compound 104b may include compound 16 having a general structure (16)

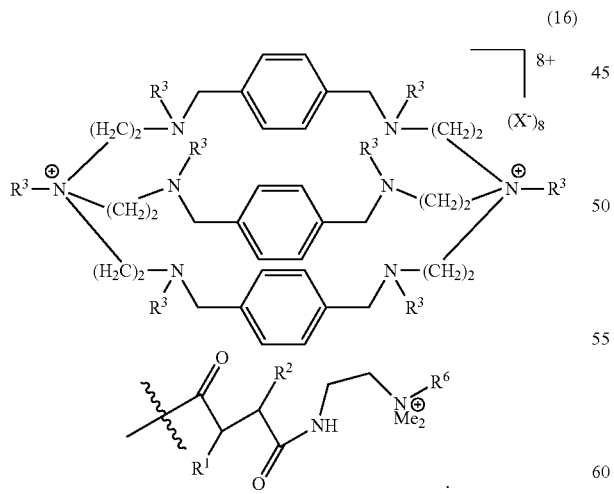

The agents (quaternary ammonium salts) depicted in compound 16 are antimicrobial in nature. In some embodiments, antimicrobials (e.g., compound 16) may be used in dental compositions and uses. Uses and various compositions for antimicrobials are more fully explained in U.S. patent application Ser. No. 11/638,327 filed Dec. 12, 2006, and entitled "METHODS AND SYSTEMS FOR PREPARING ANTIMICROBIAL FILMS AND COATINGS," which is incorporated by reference as if fully set forth herein.

In some embodiments, an example of a compound 104b may include compound 14 have a general structure

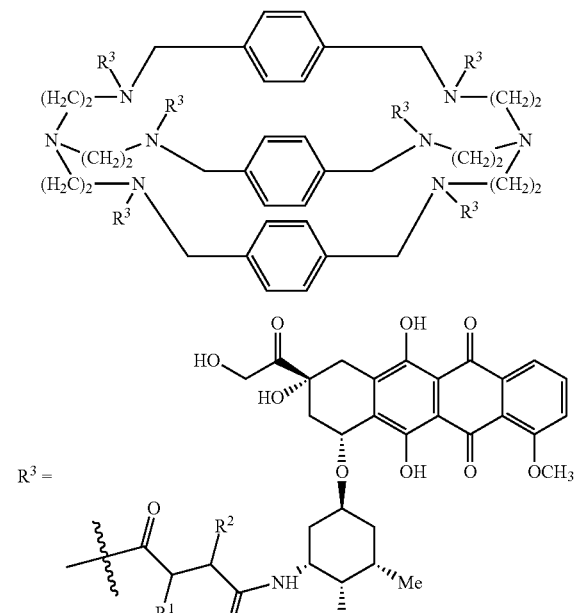

The agents (a Doxorubicin Hydrochloride Derivative) depicted in compound 14 are anticancer in nature.

In some embodiments, an example of a compound 104b may include compounds 12 and 13 having a structure (12 and 13)

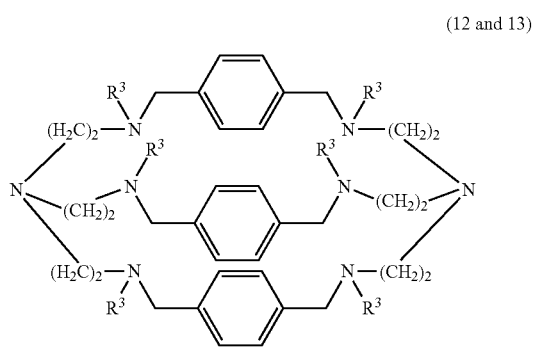

(12)

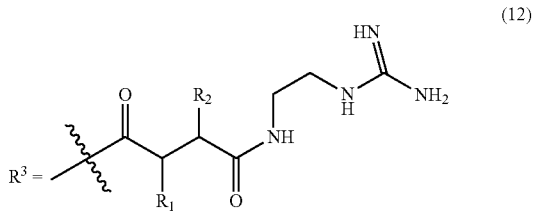

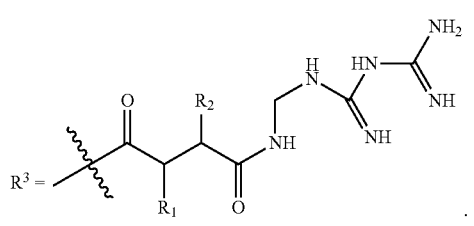
(13)
The agents depicted in compounds 12 and 13 are both anticancer and antiviral in nature.
In some embodiments, an example of a compound 104b may include compounds 17-24 having a structure
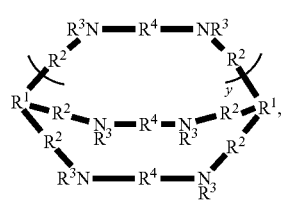
(17)
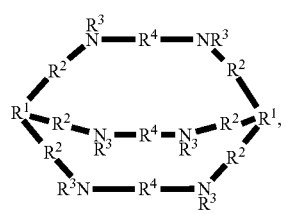
(18)
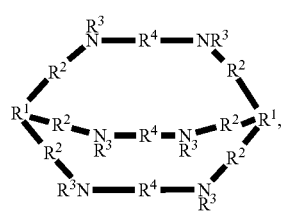
(19)
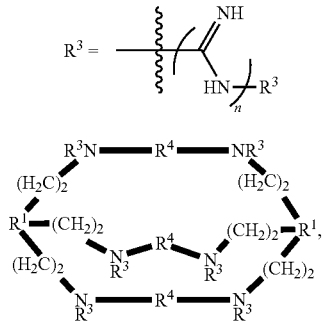
(20)
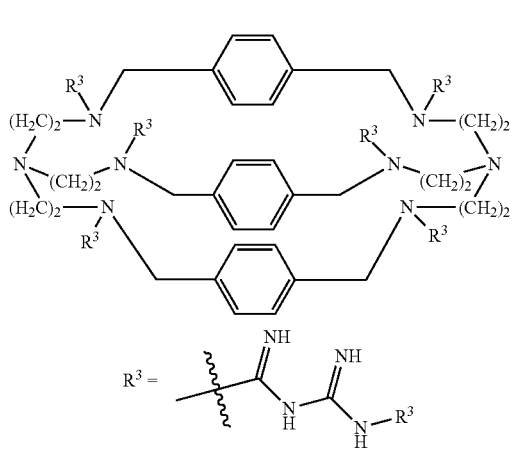
(21)
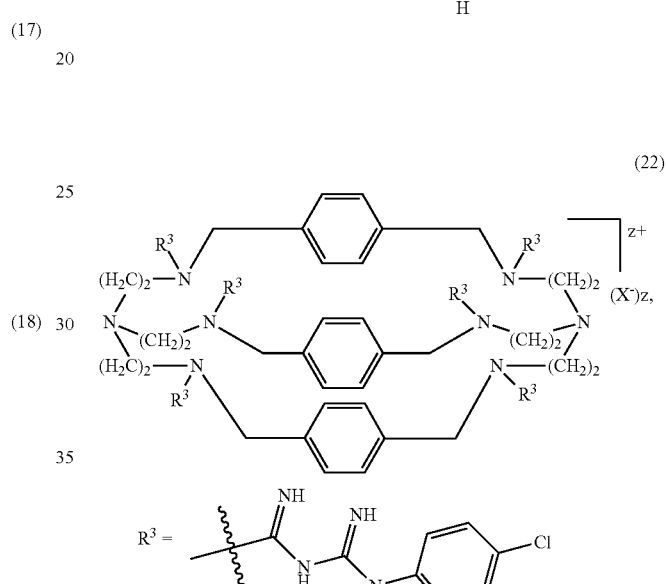
(22)
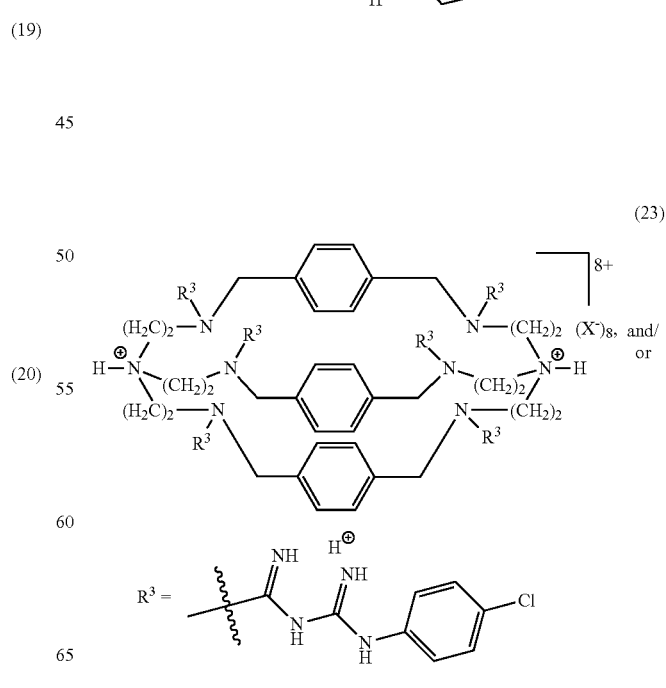
(23) and/or -continued

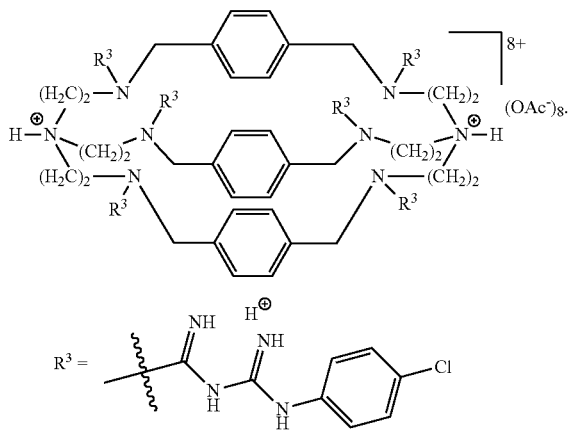
(24)

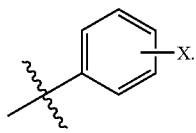

$R_3$ may include any substituent as described herein in relation to similar bridged polycyclic compounds. $R_3$ may include aryl, substituted aryl, alkyl, substituted alkyl, and/or hetero atom containing groups. In some embodiments, $R_3$ may include

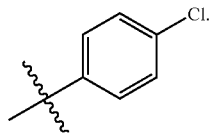

X may include, for example a halogen (e.g., Cl). X may include aryl, substituted aryl, alkyl, and/or substituted alkyl. In some embodiments, $R_3$ may include

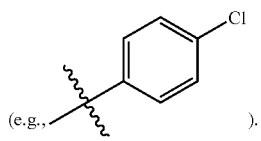

In some embodiments, $R_3$ may include a guanidine moiety and/or a substituted guanidine moiety. In some embodiments, $R_3$ may include a halogenated aryl group (e.g., 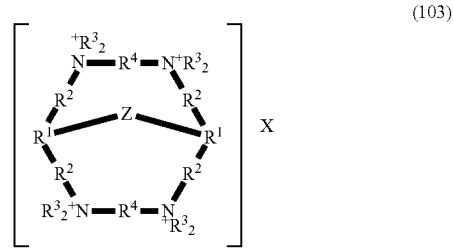 ).

n may range from 1-10, 2-8, 2-4, 3-6, 2-3, or 1-3. In some embodiment, n may be 2. In some embodiments, z may represent a charge on the chemical compound and an appropriate number of counterions. z may range from 1-16, 2-14, 6-14, or 8-14. In some embodiments, y may represent a number of bridges coupling the Nitrogens of the chemical compound. y may range from 3-8, 3-5, or 3-4.

In some embodiments, compounds such as 104b (e.g., 10-24) may include salts of the compounds. Salts may include organic and/or inorganic counterions. Counterions may include any of the examples described herein. In some embodiments, a salt of 104b (e.g., 10-24) may include an acetate counterion. A salt of 104b (e.g., 10-24) may include a charge from 1-20, 1-14, 4-14, 6-14, 4-10, or 4-8.

In some embodiments, a compound 103 may have a general structure

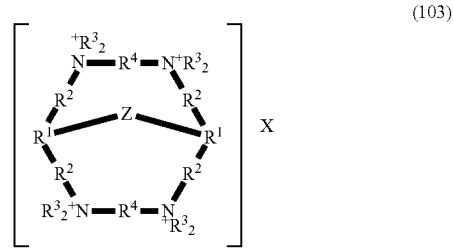
(103)

In some embodiments, $R^1$ may be independently alkyl, substituted alkyl, aryl, substituted aryl, N,N$^+$R$^3$, heterocycle, or substituted heterocycle. $R^2$ may be independently alkyl, substituted alkyl, aryl, substituted aryl, heterocycle, substituted heterocycle, covalent bond, or alkene. $R^3$ may be independently a pharmaceutically active agent, alkyl, substituted alkyl, aryl, substituted aryl, heterocycle, substituted heterocycle, alkene, ether, PEG, or PEI. $R^4$ may be independently alkyl, substituted alkyl, aryl, substituted aryl, N$^+$R$^3$, heterocycle, substituted heterocycle, alkyl ether, PEG, PEI, ether, contains boron, or alkene. $R^4$ may independently include amide, alcohol, ester, sulfonamide, or sulfanilamide. $R^4$ may be independently alkyl, substituted alkyl, aryl, substituted aryl, heterocycle, substituted heterocycle, ether, amide, alcohol, ester, sulfonamide, sulfanilamide, or alkene. X may be one or more counter ions. Z may include at least one bridge.

In some embodiments, at least one of the bridges may be —$R^2$—N$_+$R$^3{}_2$—$R^4$—N$^+$R$^3{}_2$—$R^2$—. Each bridge may independently couple $R^1$ to $R^1$. In some embodiments, at least one of the bridges may be —$R^2$—NR$^3$—$R^4$—N$^+$R$^3{}_2$—$R^2$—. Each bridge may independently couple $R^1$ to $R^1$. In some embodiments, at least one of the bridges may be —$R^2$—NR$^3$—$R^4$—NR$^3$—$R^2$—. Each bridge may independently couple $R^1$ to $R^1$. In some embodiments, at least one of the bridges may be —$R^2$—N=$R^4$=N—$R^2$—. Each bridge may independently couple $R^1$ to $R^1$.

For example when Z is 1 compound 103 may be a compound 104 having a general structure

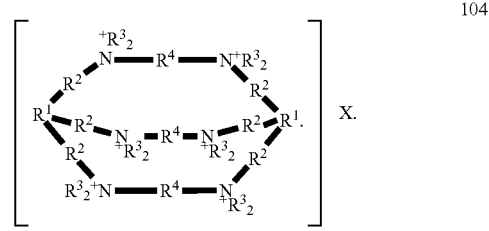
104

When, for example, Z is 2 a compound 103 may be a compound 104a having a general structure

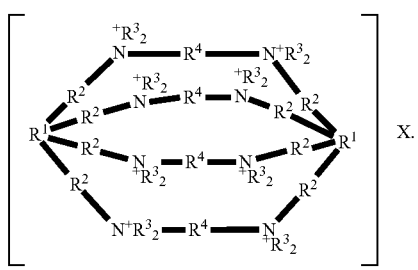

In some embodiments, a compound 104 may have a general structure

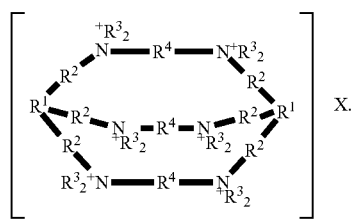

In some embodiments, $R^1$ may be alkyl, substituted alkyl, aryl, substituted aryl, $N^+R^3$, heterocycle, or substituted heterocycle. $R^2$ may be alkyl, substituted alkyl, aryl, substituted aryl, $N^+R^3$, heterocycle, substituted heterocycle, covalent bond, or alkene. $R^3$ may be alkyl, substituted alkyl, aryl, substituted aryl, heterocycle, substituted heterocycle, alkyl ether, PEG, PEI, or alkene. $R^4$ may be alkyl, substituted alkyl, alkyl, substituted aryl, $N^+R^3$, heterocycle, substituted heterocycle, alkyl ether, PEG, PEI, ether, or alkene. $R^4$ may include amide, alcohol, ester, sulfonamide, or sulfanilamide. X may be one or more counter ions.

In some embodiments, counterions may include one or more halogens (e.g., Br, Cl, I, etc.). A specific embodiment of a halogen counterion may include Iodine which has proven as a more effective counterion for antimicrobial compounds. As has been discussed herein, counterions may affect the properties of the chemical compound and subsequent composition. Boron based counterions may increase certain antimicrobial properties (e.g., $BF_4-$).

In some embodiments, salts of specific counterions may be added to a pharmaceutical composition to increase the effectiveness of the composition. For example, any of the counterions described herein for use in making the bridged polycyclic compound (e.g., counterions which increase a pharmaceutically active agent's effectiveness of the compound) may be added to the composition later (e.g., as a salt such as sodium or potassium tetrafluoroborate). In some embodiments, a combination of the two strategies may be used, additionally allowing for two or more different counterions or salts to be included in the final formulation of the composition. Each of the counterions and/or salts may increase the effectiveness of the composition in a different manner. Other examples of counterions (which may be added as an appropriate salt later in an ion exchange or a desired salt may be used during synthesis of the bridged polycyclic compound) may include an anion, a polymer, a monomer, a halogen, an iodine, a bromine, a chlorine, a triflate, a tosylate, a boron, a borate, tetrafluoroborate, a nitrogen containing group, a nitrate, a halogen, a hexafluorophosphate, an acetate, or an $NTf_2$ (wherein Tf is bis(trifluoromethanesulfonyl) imide).

In some embodiments, a compound may include one or more guest molecules coupled to the compound such as compound 106 having a general structure

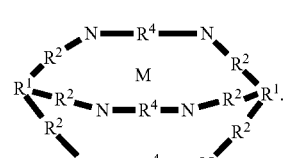

In some embodiments, $R^1$ may be alkyl, substituted alkyl, aryl, substituted aryl, $N,N^+R^3$, heterocycle, or substituted heterocycle. $R^2$ may be alkyl, substituted alkyl, aryl, substituted aryl, $N^+R^3$, heterocycle, substituted heterocycle, covalent bond, or alkene. $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. M may include one or more guest molecules associated with one or more portions of compound 106 (e.g., amines). M may include one or more metals. M may include silver, zinc, copper, gold, calcium, nickel, cobalt, barium, strontium, lead, lanthanum, iron, manganese, cadmium, magnesium, yttrium, lanthanum, cesium, praseodymium, neodymium, europium, gadolinium, terbium, dysprosium, holmium, erbium, thulium, ytterbium, or alkaline earth metals or cesium. In some embodiments, M may include organic cation salts as templates (e.g., trimethyl ammonium, etc.). M may include light activated elements such that an antiviral or anticancer property of M is increased when exposed to light. X may be one or more counter ions.

In some embodiments, M may be one or more guest molecules. X may be one or more counter ions. M (e.g., Ag+ counter ion) may bind with one or more portions of a bridged polycyclic compound, thereby keeping M in close proximity (e.g., F— ions have been reported and verified by x-ray single crystal structure to bind in ammonium salt cavitands). An anion may bind to an ammonium thus affording a close association of the cation counterion. In some embodiments, M may pi-bond coordinate to $R^4$ (e.g., aryl) or a heterocycle binding (e.g., pyridinyl $R^4$ nitrogen to a Ag+ or a phenol —OH or O— binding to the Ag+).

In some embodiments, M may be two silver metals associated with compound 106 forming a compound 106a having the general structure

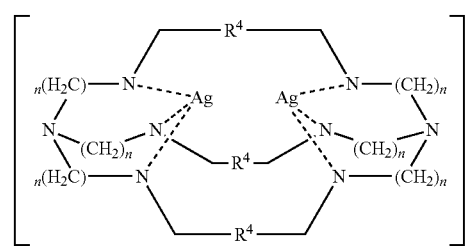

In some embodiments, a compound may include one or more guest molecules coupled to the compound such as compound 108 having a general structure

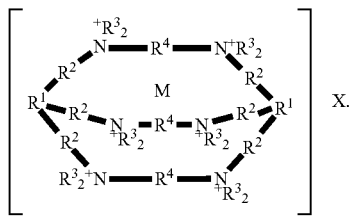

In some embodiments, $R^1$ may be alkyl, substituted alkyl, aryl, substituted aryl, $N^+R^3$, heterocycle, or substituted heterocycle. $R^2$ may be alkyl, substituted alkyl, aryl, substituted aryl, $N^+R^3$, heterocycle, substituted heterocycle, covalent bond, or alkene. $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^3$, heterocycle, substituted heterocycle, alkyl ether, PEG, PEI, ether, or alkene. M may be one or more metals. M may include silver, zinc, copper, gold, calcium, nickel, cobalt, barium, strontium, lead, lanthanum, iron, manganese, cadmium, magnesium, yttrium, lanthanum, cesium, praseodymium, neodymium, europium, gadolinium, terbium, dysprosium, holmium, erbium, thulium, ytterbium, or alkaline earth metals or cesium. In some embodiments, M may include organic cation salts as templates (e.g., trimethyl ammonium, etc.). M may include light activated elements such that an antiviral and/or anticancer property of M is increased. X may be one or more counter ions.

It should be understood that any of the compounds depicted herein may or may not have one or more metals coupled to the structure. For example, a structure depicted with a metal associated with the compound also includes a compound without a metal associated with the compound. A structure depicted without a metal associated with the compound also includes a compound with a metal associated with the compound. Although in many instances metals depicted herein are shown positioned within a space defined by compounds described herein, this should not be seen as limiting, metals may be coupled (e.g., complexed to) to a compound along an outer surface of the compound.

Metals may include any elements in the periodic chart designated as metals, known to one skilled in the art. In some embodiments, metals may include any cationic metal known to one skilled in the art (e.g., Zn, Cu, Au, Ag, Cs, Mn, Mg, Ca, Ni, Co, etc.). In some embodiments, metals may include metals which have antiviral and/or anticancer properties and/or anti-inflammatory properties (e.g., Ag, Zn, etc.). In some embodiments, metals may function to couple one or more atoms or molecules within a compound (e.g., compound 108) and/or to the surface of the compound. In some embodiments, one or more metals coupled to a compound may include one or more inorganic/organometallic compounds. A compound (e.g., a bridged polycyclic compound) may include two or more different metals coupled (e.g., associated in some way) to the compound. In some embodiments, a metal may be coupled to a bridged polycyclic molecule.

In some embodiments, $R^1$ may be $N^+$(1-22C alkyl), $N^+$(1-12C alkyl), $N^+$(1-6C alkyl), $N^+$(6C alkyl), $N^+R^3$,

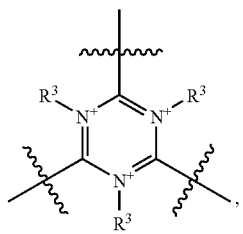

cyclam, aza crown ether, tris ethylamine N substituted cyclam, or

In some embodiments, $R^2$ may be 1-2C alkyl, 1-6C alkyl, 2-4C alkyl, $CH_2$, or a bond (e.g., covalent, ionic) between $R^1$ and an N of, for example, compound 108.

In some embodiments, $R^3$ may be hydrophobic or hydrophilic. $R^3$ may be 1-3C alkyl, 4-5C alkyl, 6-1° C. alkyl, 7-9C alkyl, 10-22C alkyl, 15-22C alkyl, 6-1° C. alkyl ether, 7-9C alkyl ether, methyl, PEI (polyethyleneimine), or PEG (polyethyleneglycol). $R^3$ may be 6C alkyl. $R^3$ may be a polymer. $R^3$ may be an oxazoline polymer.

In some embodiments, $R^4$ may include alkyl or substituted alkyl.

In some embodiments, $R^4$ may be an aryl, substituted aryl, heterocycle, or substituted heterocycle. $R^4$ may be

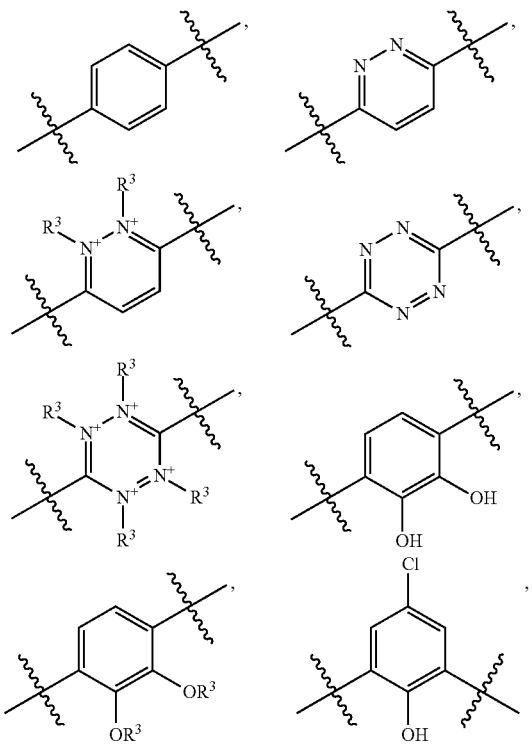

-continued

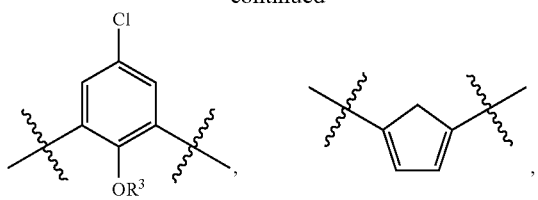

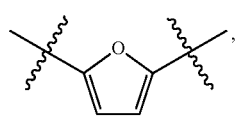

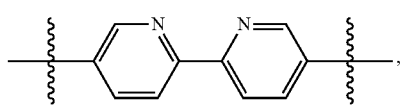

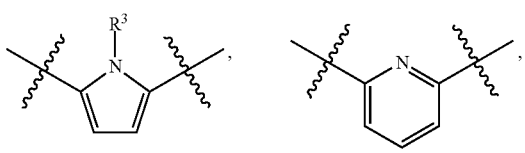

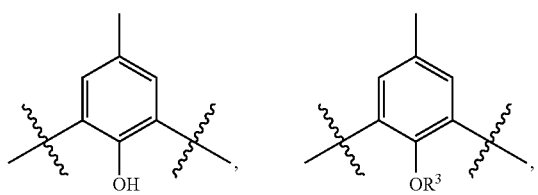

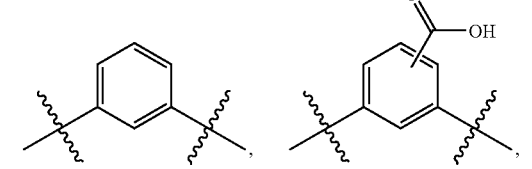

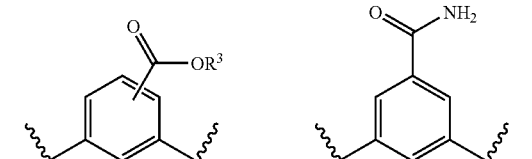

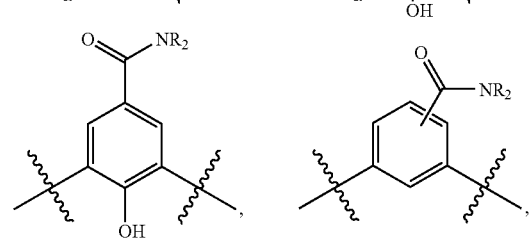

-continued

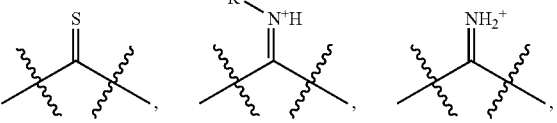

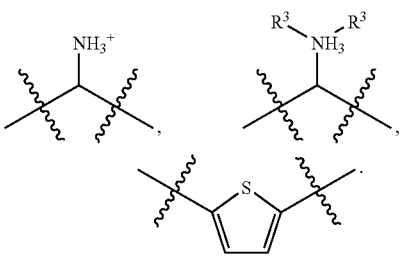

Forming one or more portions of a compound from one or more aromatic rings may provide advantages. Advantages may include providing rigidity to the compound enhancing the stability of the compound. Aromatic rings may facilitate the self-assembly of the constituent parts of the compound. Other advantages may include pie stacking of compounds relative to one another or of "guests" positioned within the compound. A substituted aryl or heterocycle may include moieties (e.g., N) which bind to other elements (e.g., metals such as silver) or molecules. $R^4$ may include substituents (e.g., $R^3$) which effect properties of a compound as a whole (e.g., hydrophobicity, hydrophilicity, self-cleaning, antimicrobial, cross-coupling properties).

In some embodiments, a compound 108 may include an embodiment such as compound 110 having a general structure

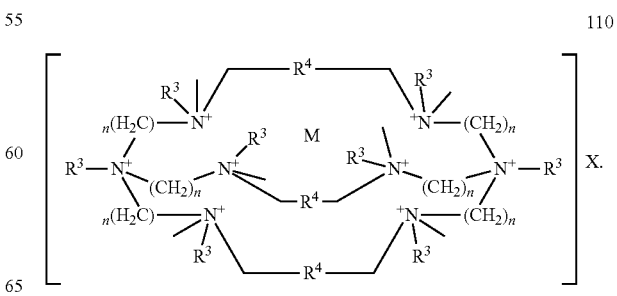

In some embodiments, $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^+R^3_2$, heterocycle, substituted heterocycle, alkyl ether, PEG, PEI, ether, or alkene. M may include one or more "guest" molecules (e.g., one or more metals). X may be one or more counter ions.

In some embodiments, M may be two silver metals associated with compound 110 forming a compound 112 having the general structure

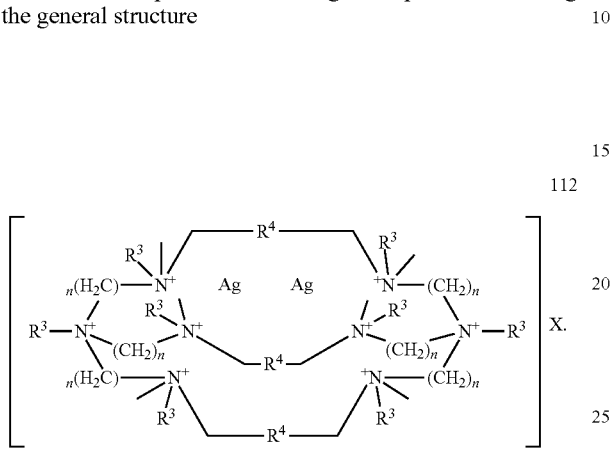

112

In some embodiments, $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^+R^3_2$, heterocycle, substituted heterocycle, alkyl ether, PEG, PEI, ether, or alkene. M may be one or more guest molecules. X may be one or more counter ions. M (e.g., Ag+ counter ion) may bind thereby keeping M in close proximity (e.g., F— ions have been reported and verified by x-ray single crystal structure to bind in ammonium salt bridged polycyclic molecules). An anion may bind to an ammonium thus affording a close association of the cation counterion. In some embodiments, M may pi-bond coordinate to $R^4$ (e.g., aryl) or a heterocycle binding (e.g., pyridinyl $R^4$ nitrogen to a Ag+ or a phenol —OH or O— binding to the Ag+).

In some embodiments, a compound 104 may include an embodiment such as compound III having a general structure In some embodiments, a compound 104 may include any number of combination of embodiments such as compound 113 having a general structure

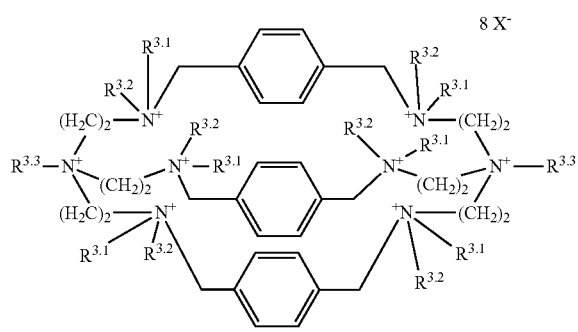

113

Where:

113a is $R^{3.1}=C_6H_{13}$, $R^{3.2}=CH_3$ and $R^{3.3}=R^{3.1}$ or $R^{3.2}$ 113b is $R^{3.1}=C_8H_{17}$, $R^{3.2}=CH_3$ and $R^{3.3}=R^{3.1}$ or $R^{3.2}$ 113c is $R^{3.1}=C_{10}H_{21}$, $R^{3.2}=CH_3$ and $R^{3.3}=R^{3.1}$ or $R^{3.2}$ 113d is $R^{3.1}=C_{12}H_{25}$, $R^{3.2}=CH_3$ and $R^{3.3}=R^{3.1}$ or $R^{3.2}$ 113e is $R^{3.1}=C_6H_{13}$, $R^{3.2}=CH_2Ph$ and $R^{3.3}=R^{3.1}$ or $R^{3.2}$ 113f is $R^{3.1}=C_{12}H_{25}$, $R^{3.2}=CH_2Ph$ and $R^{3.3}$ $R^{3.1}$ or $R^{3.2}$ 113h is $R^{3.1}=C_4H_9$, $R^{3.2}=CH_3$ and $R^{3.3}=R^{3.1}$ or $R^{3.2}$ In some embodiments, a compound 104 may include a an embodiment such as compound 114 having a general structure

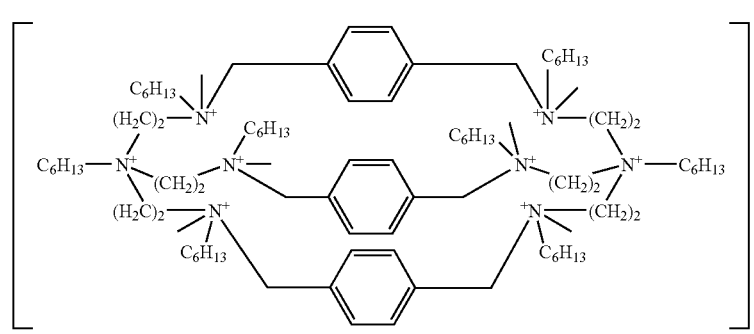

111

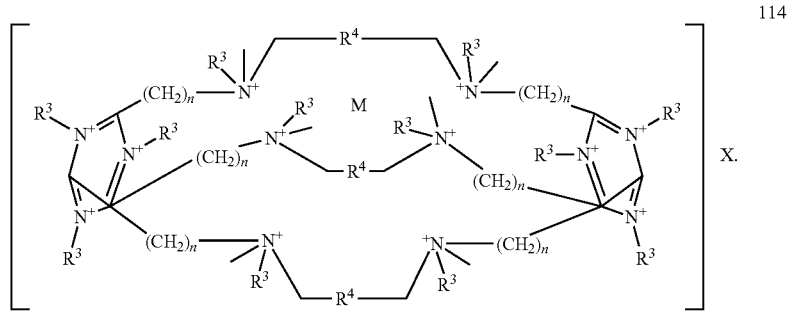

In some embodiments, $R^3$ may be alkyl, substituted alkyl, aryl, substituted aryl, heterocycle, substituted heterocycle, alkyl ether, PEG, PEI, or alkene. $R^4$ may be alkyl, substituted alkyl, alkyl, substituted aryl, $N^+R^3{}_2$, heterocycle, substituted heterocycle, alkyl ether, PEG, PEI, ether, or alkene. M may be one or more metals. X may be one or more counter ions.

Substituents (e.g., $R^3$) may be configured to perform a variety of functions. By using different substituents, properties of a compound such as the bridged polycyclic compounds described herein may be customized to meet a particular industrial and/or individual's need. For example, $R^3$ may be hydrophobic or hydrophilic depending upon the specific property needed.

In some embodiments, a substituent (e.g., $R^3$) may be multifunctional such that it imparts two or more properties to a formed compound. For example a substituent (e.g., $R^3$) may function to increase the hydrophilicity of a compound, as well as, function as a cross-coupling reagent to cross-link compounds to one another under appropriate conditions (e.g., a substituent may include one or more heteroatoms within its structure such as N, O, and S).

In some embodiments, substituents such as $R^3$ may function to enhance hydrophobicity and/or lipophilicity. Depending upon the needs of a customer the hydrophobicity/lipophilicity of a compound may be increased. Adjusting the hydrophobicity/lipophilicity of a compound may consequently adjust the solubility of the compound in a particular solvent and/or matrix. Increasing the lipophilicity of a substituent (e.g., $R^3$) coupled to an ammonium salt may increase the anti-microbial activity of a compound. In some embodiments, a compound may have a minimum inhibitory concentration (MIC) of less than 900 µM, of less than 600 µM, or of less than 300 µM. A discussion of relationship between substituent chain length and antimicrobial activity of quaternary ammonium salts may be found in Pernak, J. et al., "Synthesis and anti-microbial activities of some pyridinium salts with alkoxymethyl hydrophobic group" *Eur. J. Med. Chem. Vol.* 36, 2001, 899-907, which is incorporated by reference as if fully set forth herein.

The relationship between substituent chain length and antimicrobial activity is demonstrated in tests conducted on 113a, 113b, 113d, 113e, and 113h detailed herein in the Examples portion. A series of bridged polycyclic compounds were synthesized wherein different substituents were coupled to the quaternary ammonium moieties. Substituents included C1, C4, C6, C8, C12, and benzyl in combinations of C1 with C4, C6, C8, and C12, as well as, combinations of benzyl with C6 and C12. Time kill and residual surface tests of the antimicrobial strength of the compounds were tested against examples of gram+bacteria (e.g., *Staphylococcus aureus*, most common surgical wound infection), gram-bacteria (e.g., *Escherichia coli*, most commonly acquired hospital infection), and fungus (e.g., *Aspergillus niger*, a toxic black mold found in residences). Of the various alkyl chains combined with C1 tested, the C6,C1 compound tested as the strongest antimicrobial compound. When the test results of the C6,C1 were compared to the benzyl derivatives, once again, the C6,C1 derivative tested as the overall strongest antimicrobial.

The 113a C6C1 compound is unique in regards to the relatively short alkyl chain vs. known quaternary antimicrobials and high antimicrobial activity. Discrete quaternary ammonium or pyridinium antimicrobial molecules usually possess long alkyl chains. The most effective discrete (e.g., noncyclic) quaternary ammonium or pyridinium salt antimicrobials have an alkyl chain length between 12 and 18 carbon atoms as described by Thorsteinsson, T. Loftsson et al. "Soft Antimicrobial Agents: Synthesis and Activity of Labile Environmentally Friendly Long Chain Quaternary Ammonium Compounds" in J. Med. Chem. Vol. 46, 2003, 4173-4181, which is incorporated by reference as if fully set forth herein.

In general it is known in the art that quaternary ammonium compounds are effective biocidal agents when they possess an alkyl chain with at least eight carbon atoms (Chen, C.Z. et al. "Recent Advances in Antimicrobial Dendrimers", Adv. Mater., 2000, vol. 12, No. 11, 843-846, which is incorporated by reference as if fully set forth herein). In a study of dendrimer quaternary ammonium salts, dendrimer biocides carrying $C_{10}$ alkyl chains were the most potent (Chen, C. Z. et. al. "Quaternary Ammonium Functionalized Poly(proopylene imine) Dendrimers as Effective Antimicrobials: Structure-Activity Studies" Biomacromolecules, 2000, Vol. 1,No. (3), 473-480, 2000), which is incorporated by reference as if fully set forth herein).

Typically, non-discrete polymers are some of the only antimicrobials to show any appreciable antimicrobial activity with alkyl groups of <8 carbons. However, non-discrete polymers (e.g. polyethyleneimine quaternary ammonium containing polymers) demonstrated weaker overall antimicrobial activity in antimicrobial residual surface tests (Lin, J.A.M. Klibanov et. al. "Making thin polymeric materials, including fabrics, microbicidal and also water-repellent" Biotechnology Letters, 2003, Vol. 25, 2003, 1661-1665), which is incorporated by reference as if fully set forth herein).

Furthermore, the straightforward route and synthesis efficiency makes bridged polycyclic compounds (e.g., 113a) more attractive from a manufacturing standpoint over the more laborious methods required for typical dendrimer synthesis. Both bridged polycyclic compounds (e.g., 113a) and dendrimers have the advantage of being polyvalent (multiple positively charged sites on one molecule to attract microbes) affording increased activity vs. traditional discrete quaternary ammonium salts (U.S. Pat. No. 6,440,405 to Cooper et al.). However, the dendrimer synthesis requires large volumes of solvents/reagents relative to obtained product and long periods of time (days) to synthesize as described by in U.S. Pat. No. 6,440,405 to Cooper et al., which is incorporated by reference as if fully set forth herein.

In some embodiments, substituents such as $R^3$ may function to enhance hydrophilicity and/or lipophobicity. Depending upon the needs of a customer the hydrophilicity/lipophobicity of a bridged polycyclic compound may be increased. Adjusting the hydrophilicity/lipophobicity of a compound may consequently adjust the solubility of the compound in a particular solvent and/or matrix.

In some embodiments, substituents (e.g., $R^3$) may function to enhance the self-cleaning properties of which the compound may impart to a surface to which the compound is coupled. In some embodiments, substituents may enhance the antimicrobial properties of the compound. Self-cleaning and antimicrobial properties may function in combination with one another. The self-cleaning properties of compounds described herein are more fully described in U.S. Pat. No. 8,067,402 to Whiteford et al. which is incorporated by reference as if fully set forth herein.

In some embodiments, counter ions for a bridged polycyclic compound may be selected to adjust particular properties of a compound or to introduce new properties to the compound. Adjusting properties of a compound based on a selection of a particular counter ion allows further customization of a compound. In some embodiments, counter ions may include counter ions which have or enhance antimicrobial properties and/or anti-inflammatory properties (e.g., boron, zinc). In some embodiment, counter ions may adjust the hydrophilicity or hydrophobicity of the complex. Counter ions may include metals. Research has held that specific counter ions do affect the antimicrobial activity of quaternary ammonium compounds.

Counter ions may include, but are not limited to, organic, inorganic, or organometallic moieties. Examples of counter ions may include inorganic ions (e.g., halogen ions, such as fluorine, bromine, chlorine and iodine), organic ions (e.g., tosylate, prosylate sulfuric acid, nitric acid and phosphoric acid, and ions of organic acids such as succinic acid, fumaric acid, lactic acid, glycolic acid, citric acid, tartaric acid and benzoic acid), or coordinate type anions (e.g., fluoro sulfate and tetrafluoro borate).

In some embodiments, counter ions may include a hydrophobic organic group (e.g., lauryl sulfate, dodecylbenzene sulphonate, diethylhexyl sulphosuccinate, carboxylic acid derivatives with alkane, alkene or alkyne aliphatic tails such as myristic acid salts, octadecanate, dodecanoic acid salts, oleic acid salts, Palmitoleic acid salts, lauric acid salts, Stearic acid salts, phosphinic acid salts, phosphonic acid salts (i.e. tetradecylphosphonate, hexadecylphosphonate) and dodecylsulphonate, dodecylsulfate anions).

In some embodiments, bridged polycyclic compounds may be polymerized. Polymers incorporating bridged polycyclic compounds may have molecular weights high enough to inhibit systemic absorption when, for example, ingested. The minimum molecular weight, and hence the degree of polymerization of bridged polycyclic compounds, required to inhibit systemic absorption may be relatively low. Nonsystemic polymers may include a minimum degree of polymerization of 3 or greater, 6 or greater, 10 or greater, 20 or greater, or 50 or greater. In some embodiments, an enteric coating may be applied to a composition in order to inhibit absorption and/or premature absorption.

Synthesis of Bridged polycyclic Compounds

For commercialization purposes compounds such as bridged polycyclic compounds (and their metal and/or metal oxide coated counterparts) require an efficient and cost effective method of synthesis. In some embodiments, bridged polycyclic compounds may be formed through the self-assembly of two or more compounds to form much larger complex systems in fewer steps and more efficiently than traditional stepwise synthetic means.

Dynamic covalent chemistry relates to chemical reactions carried out reversibly under conditions of equilibrium control. The reversible nature of the reactions allows for the correction of errors in synthetic processes where dynamic covalent chemistry operates. Since the formation of products occurs under thermodynamic control, product distributions depend only on the relative stabilities of the final products. In kinetically controlled reactions, however, it is the free energy differences between the transition states leading to the products that determines their relative proportions. Supramolecular chemistry has had a huge impact on synthesis at two levels: one is noncovalent synthesis, or strict self-assembly, and the other is supramolecular assistance to molecular synthesis, also referred to as self-assembly followed by covalent modification. Noncovalent synthesis has given us access to finite supermolecules and infinite supramolecular arrays. Supramolecular assistance to covalent synthesis has been exploited in the construction of more-complex systems, such as interlocked molecular compounds (for example, catenanes and rotaxanes) as well as container molecules (molecular capsules). The appealing prospect of also synthesizing these types of compounds with complex molecular architectures using reversible covalent bond forming chemistry has led to the development of dynamic covalent chemistry.

In some embodiments, self-assembly techniques (e.g., dynamic covalent chemistry) may be employed to synthesize stable compounds, which are themselves large enough to be described as nanoparticles and/or which may be used to form nanoparticles.

Bridged polycyclic compounds represented by compounds 104 and 108 may be synthesized by any means known to one skilled in the art. As has been mentioned, self-assembly may be a useful technique for efficiently synthesizing nanoparticles described herein. In some embodiments, nanoparticles such as compounds 104 and 108 may be formed via self-assembly using Schiff base condensation reactions between amines and aldehydes to form an imine as depicted in Scheme 3. For example, a trifunctional amine (e.g., tris(2-aminoethyl) amine (TREN)) may be reacted with a bifunctional aldehyde (e.g., ethane-1,2-dione (glyoxal)).

Scheme 3. Schematic depiction of the formation of compound 102.

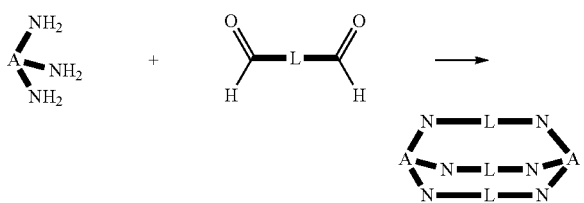

In Scheme 3, the amine depicted is trifunctional and the aldehyde is bifunctional. However, the example depicted in Scheme 3 should not be seen as a limiting embodiment. For example, a Schiff base condensation reaction is depicted in Scheme 4 in which the amine is bifunctional and the aldehyde is trifunctional.

Scheme 4. Schematic depiction of the formation of compound 102.

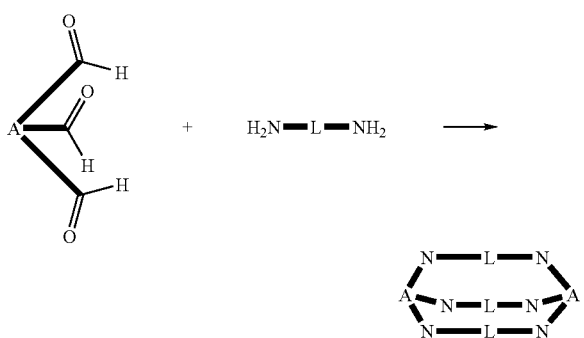

In some embodiments, two different trifunctional molecules may be reacted with one another in order to form an asymmetric adduct. Scheme 4a depicts an embodiment of the formation of an asymmetric adduct.

Scheme 4a. Schematic depiction of the formation of compound 100c.

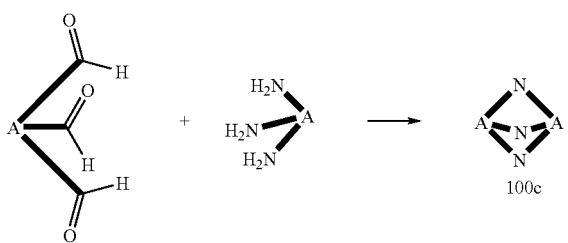

For example, a trifunctional amine (e.g., tris(2-aminoethyl) amine (TREN)) may be reacted with a trifunctional aldehyde (e.g., 1,3,5-aldehyde substituted phenyl). Triethanolamine may be functionalized at the OH with an aminoacid to give N—(CH$_2$CH$_2$OC(O)Phenyl(CHO). N—(CH$_2$CH$_2$OC(O) Phenyl(CHO) may be reacted with any triamine to give an asymmetric example of a bridged polycyclic compound. A discussion of synthesis techniques for different multifunctional ligands (e.g., trifunctional aldehydes) may be found in Chand, D. K. et al. "Synthesis of a Heteroditopic Cryptand Capable of Imposing a Distorted Coordination Geometry onto Cu(II): Crystal Structures of the Cryptand (L), [Cu(L) (CN)](picrate), and [Cu(L)(NCS)] {picrate} and Spectroscopic Studies of the Cu(II) Complexes" Inorg Chem 1996, Vol. 35, 3380-3387, which is incorporated by reference as if fully set forth herein. A Schiff base condensation may be carried out using an acid catalyst (e.g., acetic acid). A Schiff base condensation may be carried out using any means known to one skilled in the art. Techniques for amine aldehyde condensations may be found in U.S. Patent Application, Publication No. 2004/0267009 to Redko et al., which is incorporated by reference as if fully set forth herein. Further details concerning the synthesis of bridged polycyclic compounds described herein are more fully described in U.S. Pat. No. 8,067,402 to Whiteford et al.

In some embodiments, an amine may be functionalized (e.g., compound 122) by reacting with an epoxide. For example, reacting compound 122 with an epoxide may result in an epoxide ring opening and thus a free alcohol coupled to at least some of the amines in compound 122. The resulting free alcohol may be reacted with (OR)$_3$Si(CH$_2$)$_n$N$^+$R$_3$ resulting from the attack of the N on the epoxide containing carbon. This may result in an ammonium on the bridged polycyclic compound and an ammonium pendant arm. Free amines of the herein described bridged polycyclic compounds may be reacted with a di-epoxide crosslinker (e.g., 1,2,7,8-diepoxyoctane or epoxypropyl terminated polydimethylsiloxane), followed by (OR)$_3$Si(CH$_2$)$_n$N$^+$R$_3$ to functionalize the crosslinked mixture. Reaction with a vinyl epoxide may result in a light crosslink terminus and an alcohol (e.g., with which a silane may be reacted). A free amine of a bridged polycyclic compound described herein may be modified by an epoxy alkane (or glycidyl ether (e.g., hexyl, octyl or decyl glycidyl ether)), followed by further modification by a variety of alkoxysilanes with desired functional groups (e.g., an alkyl ammonium salt attached to the Si). One may modify a free amine with alkyl anhydrides (e.g., 2-octen-1-ylsuccinic anhydride).

In another example of functionalizing an amine at least in part defining a bridged polycyclic compound, a functionalized substituent may be coupled to the amine. A functionalized substituent may include an alkyl amine group. A non-limiting example of an alkyl amine may include —CH$_2$CH$_2$CH$_2$NH(CH$_2$)$_5$CH$_3$. The amine may be further functionalized. For example the amine of the alkyl amine may be alkylated such that another quaternary amine is available increasing the antimicrobial activity of the bridged polycyclic compound. The synthesis of such an embodiment is detailed in the Examples section.

In some embodiments, following a reduction to form a bridged polycyclic amine, such as compound 120 or a compound such as compound 301, a linking agent (e.g., to couple a pharmaceutically active agent to) or a pharmaceutically active agent may be coupled to a bridged polycyclic amine (e.g., compound (301)). Linking agents may be, for example, any of the compounds or reagents identified herein as R$^3$. Linking agents may include diacids, diamines, guanidines, etc. and combinations thereof. Representative example of linking agents and how to synthetically couple them to a bridged polycyclic amine are provided in detail in the Examples section herein, as well as some other examples of how to synthesize guanidines linking agents below.

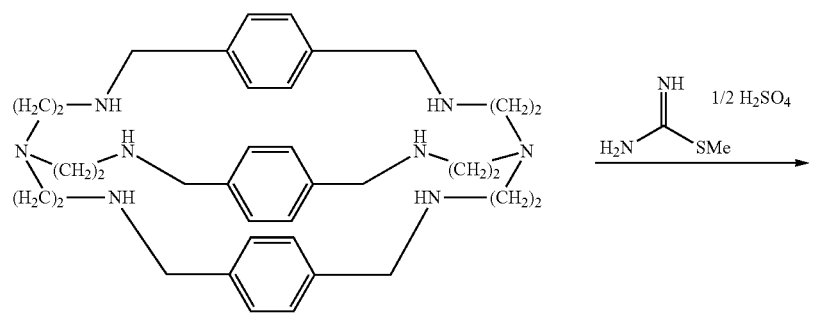
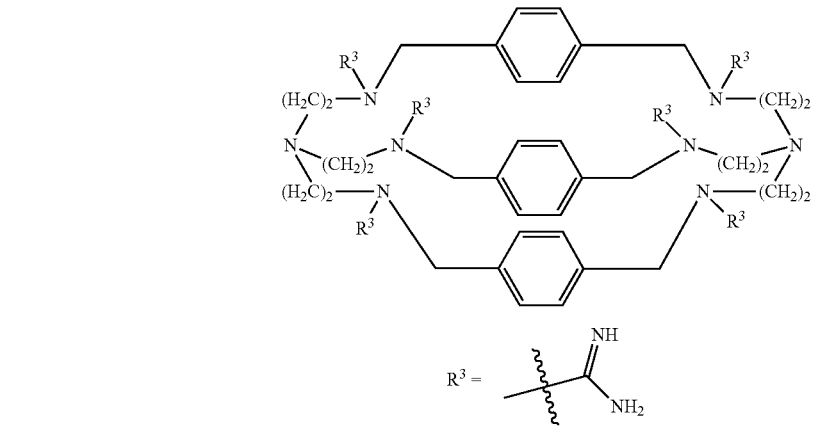
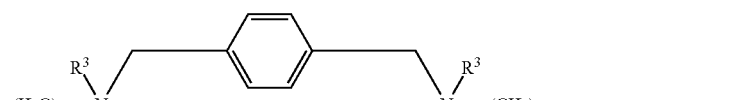
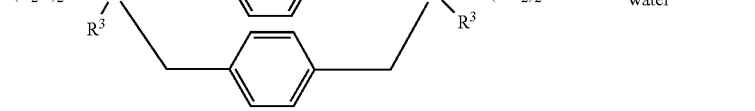
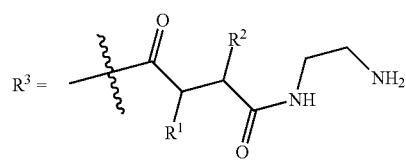
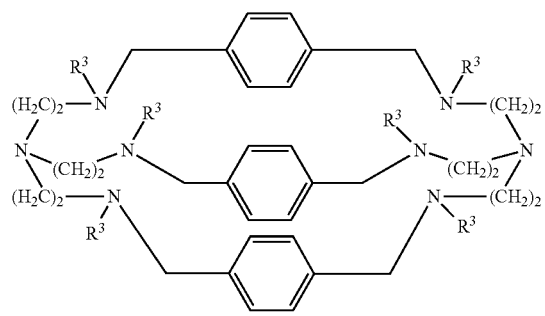
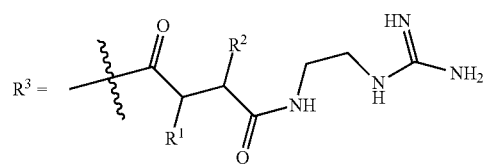

-continued
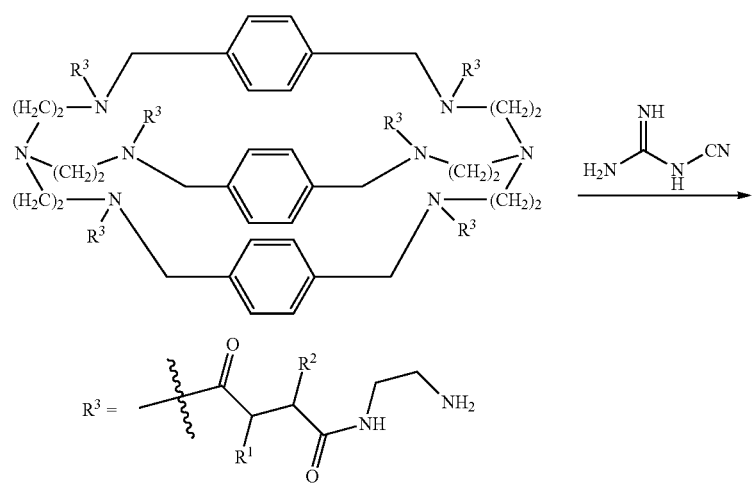
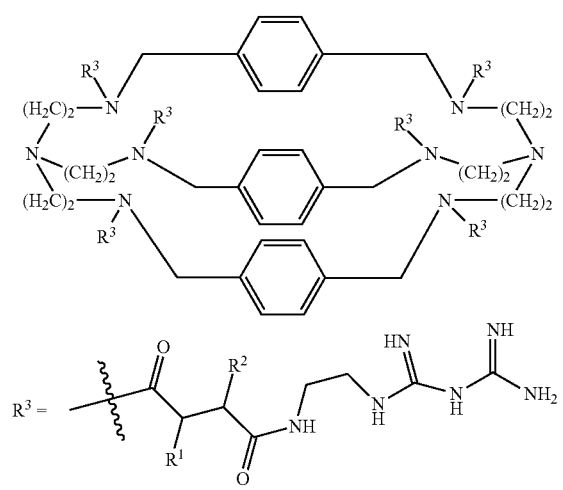

Representative example of activating agents and how to synthetically couple them to a bridged polycyclic amine are provided in detail in the Examples section herein.

In some embodiments, it may be advantageous to increase the number of active sites on to which to couple pharmaceutically active agents. One example of increasing the number of active sites on a bridged polycyclic compound may include using branched linking agents, effectively doubling or tripling the number agents which may be coupled to the bridged polycyclic compound. Representative example of branched activating agents and how to synthetically couple them to a bridged polycyclic amine are provided in detail in the Examples section herein.

Representative examples of pharmaceutically reactive agents and how to synthetically couple them to linking agents and/or bridged polycyclic compounds are provided in detail in the Examples section herein. By way of further example a synthesis of a Doxorubicin derivative and sugar derivatives of a bridged polycyclic amine displayed below.

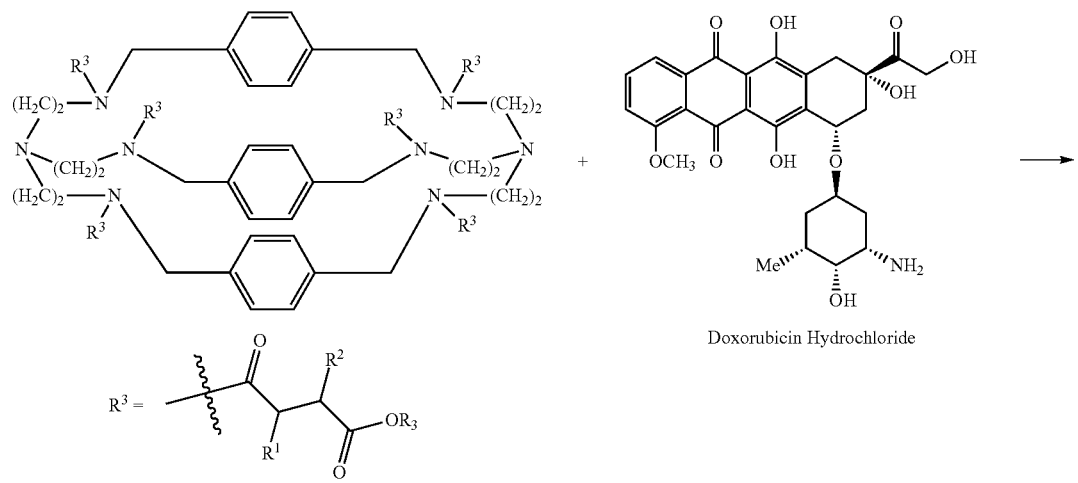

Where $R_1$, $R_2$ and H, aryl or alkyl
Where $R_3$ is Me, Et or i-Pr etc.

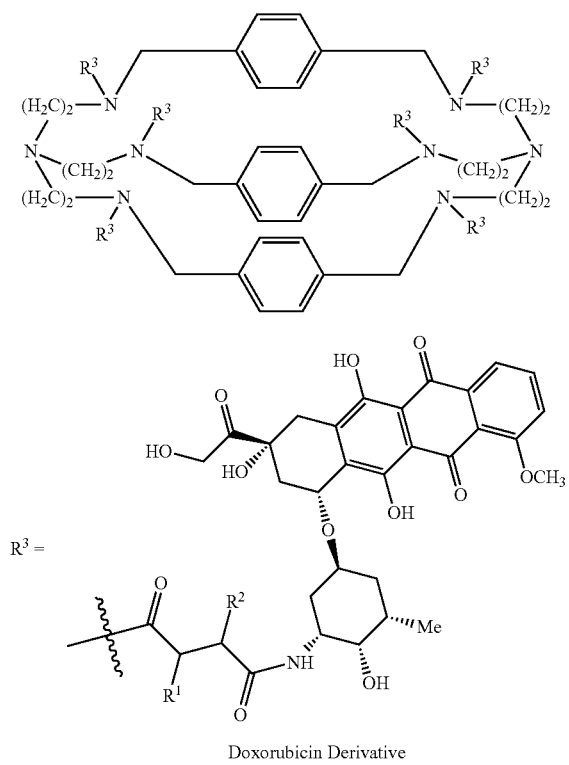

Doxorubicin Derivative

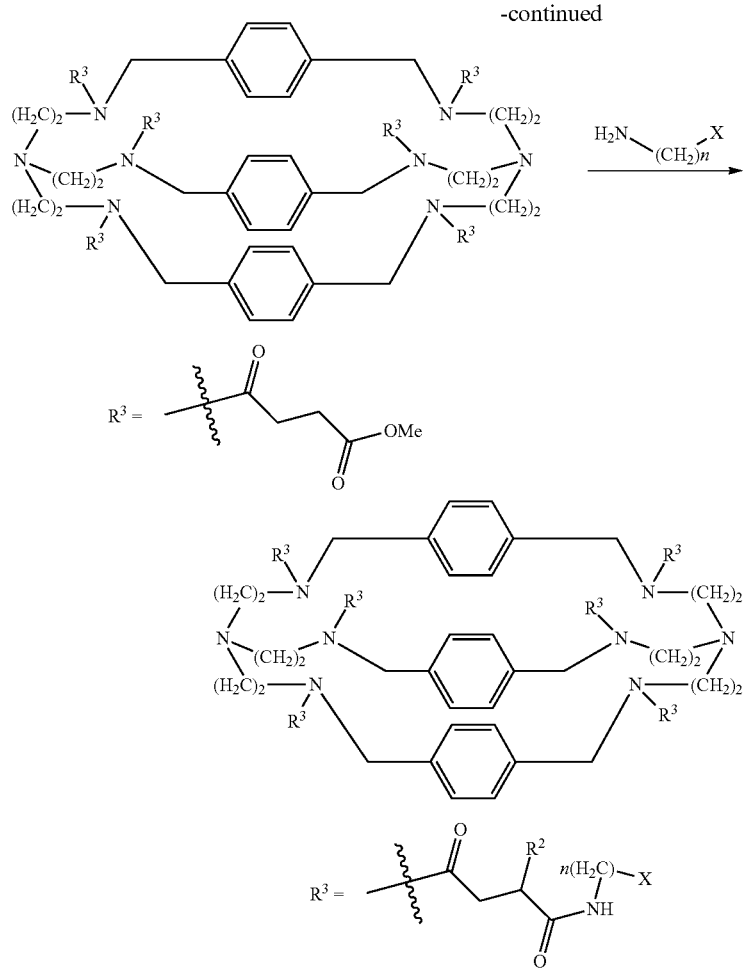

Where $n = 0$ to 12 and X is a sugar or carbohydrate

As mentioned previously, it is widely held that self-cleaning surfaces are a combination of low surface-energy species and a peculiar topographic feature based on dual-size roughness: the coarse-scale rough structure is about 10-20 μm, whereas the finer structure on top of the coarse structure is in the range of 100 nm to 1 μm. The dual-size structure has proven to be vital in generating the superhydrophobicity of the lotus leaves, especially for obtaining low water rolloff angles. Methods of synthesizing self-cleaning surfaces using bridged polycyclic amines described herein are more fully described in U.S. Pat. No. 8,067,402 to Whiteford et al.

In some embodiments, one or more amines of a bridged polycyclic compound may be functionalized in more than one step. For example, several secondary amines forming a bridged polycyclic compound may be transformed into tertiary amines, followed by subsequent transformation into a quaternary amine. Such synthetic flexibility allows customization of the amines such that different functional groups may be coupled to the same amine. Depending on the reactions conditions required to couple the different functional groups to the amine, the reactions may be run sequentially without any purification steps between coupling different functional groups to the amine.

Dosage and Administration

In some embodiments, bridged polycyclic compounds may be administered at a dosage level up to conventional dosage levels, but will typically be less than about 2 gm per day. Suitable dosage levels may depend upon the overall systemic effect of the chosen pharmaceutical agent coupled to the bridged polycyclic compound, but typically suitable levels will be about 0.001 to 50 mg/kg body weight of the patient per day, from about 0.005 to 30 mg/kg per day, or from about 0.05 to 10 mg/kg per day. The compound may be administered on a regimen of up to 6 times per day, between about 1 to 4 times per day, or once per day.

In the case where an oral composition is employed, a suitable dosage range is, e.g. from about 0.01 mg to about 100 mg per kg of body weight per day, preferably from about 0.1 mg to about 10 mg per kg and for cytoprotective use from 0.1 mg to about 100 mg per kg of body weight per day.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skills of a clinician.

While individual subject needs vary, determination of optimal ranges of effective amounts of each component is with the skill of the art. Typically, a bridged polycyclic compound may be administered to mammals, in particular humans, orally at a dose of 5 to 100 mg per day referenced to the body weight of the mammal or human being treated for a particular disease. Typically, a bridged polycyclic compound may be administered to mammals, in particular humans, parenterally at a dose of between 5 to 1000 mg per day referenced to the body weight of the mammal or human being treated for a particular disease. In other embodiments, about 100 mg of a bridged polycyclic compound is either orally or parenterally administered to treat or prevent disease.

The unit oral dose may comprise from about 0.25 mg to about 1.0 gram, or about 5 to 25 mg. The unit parenteral dose may include from about 25 mg to 1.0 gram, or between 25 mg and 500 mg. polymerized bridged polycyclic compounds may include larger dosages from 1000 to 5000 mg or more as seen with products such as colestipol for example. The unit intracoronary dose may include from about 25 mg to 1.0 gram, or between 25 mg and 100 mg. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a bridged polycyclic compound as a raw chemical, the compounds may be administered as part of a pharmaceutical preparation containing suitable pharmaceutically acceptable carriers, preservatives, excipients and auxiliaries which facilitate processing of the bridged polycyclic compound which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, 8$^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/McGraw-Hill, New York, 2001).

Pharmaceutical Compositions

Any suitable route of administration may be employed for providing a subject with an effective dosage of drugs of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the drugs used in the present invention are conveniently delivered in the form of an aerosol spray presentation from pressurized packs or nebulisers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, gels, and the like.

In practical use, drugs used can be combined as the active ingredient in intimate admixture with a pharmaceutical carrier according to conventional pharmaceutical compounding techniques. The carrier may tale a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable.

Pulmonary administration may include, for example, inhalation of aerosolized or nebulized liquid or solid particles of the pharmaceutically active component dispersed in and surrounded by a gas.

Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances that increase the viscosity of the suspension including, for example, sodium carboxymethyl cellulose, sorbitol, dextran, and/or cyclodextrins. Liposomal formulations, in which mixtures of the bridged polycyclic compound with, for example, egg yolk phosphotidylcholine (E-PC), may be made for injection. Optionally, the suspension may contain stabilizers, for example, antioxidants such as BHT, and/or preservatives, such as benzyl alcohol.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the subject, and the effect desired. A physician or veterinarian can determine and prescribe the effective amount of the drug required.

By way of general guidance, the daily oral dosage of each active ingredient, when used for the indicated effects, will range between about 0.001 to 1000 mg/kg of body weight, between about 0.01 to 100 mg/kg of body weight per day, or between about 1.0 to 20 mg/kg/day. Intravenously administered doses may range from about 1 to about 10 mg/kg/minute during a constant rate infusion. Compounds of this invention may be administered in a single daily dose, or the total daily dosage may be administered in divided doses of two, three, or four or more times daily.

The pharmaceutical compositions described herein may further be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

For instance, for oral administration in the form of a tablet or capsule, the pharmacologically active component may be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

In some embodiments, dosage forms (pharmaceutical compositions) suitable for administration may contain from about 1 milligram to about 100 milligrams or more of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase subject acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

In some embodiments, a pharmaceutically acceptable formulation may be administered to a subject topically. The formulation may be in the form of a gel or foam. In some embodiments, a formulation may include an antiviral and/or contraceptive agent. Such a formulation may be administered in the form of a vaginal gel or applied to the exterior of a condom. Such a formulation may be administered by a subject to themselves topically in the form of a gel using a one-dose disposable applicator. Such a formulation and means of administration would off a convenient and affordable way for women to protect themselves from infection with genital herpes and HIV during sex.

Surveys show that there is substantial demand in North America and Europe for such a product with an estimated billion dollar market for STI prevention products in the developed world. For example, in the US HIV and AIDS have "Direct medical costs of up to $15.5 billion per annum" (Source: *Mircobicide Development Act*). In the US, AIDS is now the number one cause of death among African-American women between the ages of 25 and 34. HIV infects more than 40 million people worldwide. About half of those infected are women and transmission by heterosexual intercourse is thought to cause 90% of cases. Seven thousand women are newly infected with HIV each day.

In the US, approximately 45 million Americans (26% of women and 18% of men) are infected with HSV-2, the causative agent of genital herpes. Genital herpes is the unrecognised pandemic of the industrialised world. Many patients are asymptomatic and pass on the virus unknowingly. In addition to the painful ulcers caused by HSV-2, patients often develop depression and anxiety. The presence of HSV-2 increases a person's risk of HIV infection by four to eight times. HSV-2 remains in affected nerve cells throughout life and can be activated to produce symptoms intermittently in some infected individuals. There is no cure for genital herpes. Ulcers typically last 3-4 weeks and may occur 4-5 times each year in affected patients. Ulcerative episodes can be suppressed by daily doses of anti-virals but these are expensive. Genital herpes is the most common cause of ulcerative genital disease in the US. The prevalence is estimated at between 15 and 25% across all countries with a 16% rate in women in Australia (12% overall). The incidence rate of genital herpes has risen rapidly and without intervention the prevalence in the US is expected to increase to 39% of men and 49% of women by 2025. The estimated cost of genital herpes in the US is over US$1.5 billion per year.

Formulation used for condom coatings may be of interest due to possible problems recently discovered with currently used products. The commonly used coating on premium condoms is Nonoxynol 9 (N-9), which has spermicidal properties. However, because of its detergent nature, N-9 has been shown to increase the risk of infection with HIV and other viruses such as HSV-2.

In some embodiments, bridged polycyclic compounds may be incorporated into a composition which is substantially nontoxic to an animal and/or human. A composition may include a solvent capable of dissolving a bridged polycyclic compound. In some embodiments, a composition may include an environmentally green solvent. A solvent may include water. In some embodiments, a composition may consist of water and a bridged polycyclic compound (e.g., 308, 309, 312, 312, 10-24, or a salt thereof). Such compositions may be administered using any method described herein including, but not limited to, orally, topically, intravenously, absorbed through the skin, injected, etc.

In some embodiments, an oral composition may include a flavoring. A flavoring may include something an animal may find palatable. For example a flavoring may include malt extract, xylitol, splenda, sucralose or any sweetener. A flavoring may range from 0.01% to 0.10%, 0.10% to 1.0%, or 1.0% to 10.0% of a composition.

In some embodiments, a composition may include a colorant. A colorant may include D&C Blue #1 or any FDA approved color. A colorant may range from 0.001% to 0.010%, 0.010% to 0.10%, or 0.10% to 1.0% of a composition.

In some embodiments, an oral composition may include a fragrance.

In some embodiments, a composition may include additional additives which may function in combination or separately from the bridged polycyclic compound in solution. Additives may function to improve a subject's health. Additives may include vitamins including, but not limited to, vitamins D and E.

All types of teeth and gum diseases can lead to serious health problems in animals. Dogs and cats make much fuller use of their teeth than humans do—using them in ways humans usually use their hands. For this reason, toothache, dental disease and loss of teeth can all have serious consequences for pets. Damage to the teeth and gums in pets is permanent and irreversible.

In some embodiments, different compositions may be formulated for different types of users. For professionals users (e.g., doctors, veterinarians), compositions may include a greater percentage of active bridged polycyclic compounds than compositions formulated for over the counter sale to nonprofessionals. Professional compositions may not include flavorings or colorants.

Additional oral compositions which may be used to deliver bridged polycyclic compounds, as well as additional uses, are described in U.S. Pat. Nos. 4,666,896 to Warner, Jr. et al., 5,393,516 to Rheinberger et al., and 5,948,390 to Nelson et al., as well as U.S. Patent Publication No. 2005/0158252 to Romanowski et al., which are incorporated by reference as if fully set forth herein.

While previous discussions herein have concentrated on the use of bridged polycyclic compounds for treating maladies associated with oral cavities of humans and animals. Bridged polycyclic compounds described herein may be used for the inhibition and/or amelioration of various maladies associated with humans and/or more particularly animals. Malidies inhibited and/or ameliorated may include diseases, parasites, viruses, infections wounds, etc.

In some embodiments, compositions including bridged polycylic compounds may be administered to treat otic maladies. Otic maladies may include, but are not limited to, ear mites and/or ear infections. Compositions including bridged polycylic compounds may be used to treat otic maladies in the form of an ear cleanser, ear wash, and/or ear drops. Additionally, otic infections may be combinations of gram negative and gram positive bacteria, fungus, yeast, and/or mold In some embodiments, bridged polycyclic compounds may be incorporated into a composition which is substantially nontoxic to an animal and/or human. A composition may include a solvent capable of dissolving a bridged polycyclic compound. In some embodiments, a composition may include an environmentally green solvent.

A solvent may include water. In some embodiments, a composition may consist of water and a bridged polycyclic compound (e.g., 308, 309, 312, 312, 10-24, or a salt thereof).

In some embodiments, an otic composition may include a colorant, although colorants may be optional for otic compositions. A colorant may include D&C Blue #1 or any FDA approved color. A colorant may range from 0.001% to 0.010%, 0.010% to 0.10%, or 0.10% to 1.0% of a composition.

In some embodiments, an oral composition may include a fragrance.

In some embodiments, a composition may include additional additives which may function in combination or separately from the bridged polycyclic compound in solution.

In some embodiments, different compositions may be formulated for different types of users. For professionals users (e.g., doctors, veterinarians, veterinarians), compositions may include a greater percentage of active bridged polycyclic compounds than compositions formulated for over the counter sale to nonprofessionals.

Professional compositions may not include colorants.

In some embodiments, a composition (e.g., otic composition) may include glycerin, propylene glycol, polyethylene, mineral oil, benzyl alcohol, and/or ethyl alcohol.

Additional otic compositions which may be used to deliver bridged polycyclic compounds (e.g., 308, 309, 312, 312, 10-24, or a salt thereof), as well as additional uses, are described in U.S. Pat. Nos. 5,753,268 to Stolle et al., 5,753, 269 to Groh et al., and 5,597,560 to Bergamini et al., which are incorporated by reference as if fully set forth herein. In some embodiments, quinolones may be coupled to and/or combined to form a salt with bridged polycyclic compound and used to treat otic maladies. In some embodiments, enrofloxicin may be combined with bridged polycyclic compounds to form a composition effective in inhibiting and/or ameliorating otic maladies. The acid functionality of enrofloxicin may be used to couple enrofloxicin directly to an amine of the bridged polycyclic compound using methods known to one skilled in the art and outlined in similar examples herein. In some embodiments, multiple equivalents (e.g., eight) of commercially available acid enrofloxicin (CAS Number 93106-60-6) from Aldrich may be reacted with the freebase of 5 providing a combination salt antimicrobial that is effective for gram negative, gram positive bacteria, yeasts and molds for ear infections of dogs, felines, animals and people. In some embodiments, the resulting salt may be used as a topical that may be used for any skin or wound infection.

In some embodiments, compositions including bridged polycylic compounds may be administered to treat ophthalmic maladies.

In some embodiments, compositions including bridged polycylic compounds may be administered topically. For example, compositions may be administered topically to treat bacterial infection, fungal infection, viral infection, and for general wound healing. Compositions may be administered topically in the form of, for example, a topical spray, body wash (e.g., for treating animals to control fungal, bacterial, and other microbial infections, including itching, flaking, hot spots, rashes, dryness, etc.), and/or a shampoo (e.g., for treating scalp related problems). Compositions may be administered topically as a disinfectant and healing agent for burns, small cuts, abrasions, and/or bites. Compositions may be administered topically to inhibit and/or ameliorate a variety of skin conditions including, but not limited to, bed sores, eczema, bacterial infections, rashes, insect bites (including but not limited to the inflammation and pain associated with insect bites), poison ivy, minor scrapes, boils, and/or sores. Compositions may be applied topically as lotions (e.g., to control germs, skin moisture, condition and promote healing). Topical applications may be used to treat parasites. Parasites may include, for example, fleas, ticks, and/or lice. Parasites may include, for example, heart worms and/or ring worms. Compositions may be administered topically to inhibit and/or ameliorate acute-chronic fungal infections such as ringworm, athlete's foot, jock itch, etc., as well as, other fungal infections (e.g., Fingernail and toenail fungus). Compositions may be administered topically to inhibit and/or ameliorate Idiopathic dermatology problems—Generalized pruritus (itching). Compositions may be administered topically to inhibit and/or ameliorate Atopic and contact dermatitis (assists in soothing, reducing inflammation, and stimulates healing). Common examples: itchy skin following contact with lawn grass, or other irritant, which can provoke the need to scratch the points of contact.

In some embodiments, compositions including bridged polycylic compounds may be administered topically for uses commonly associated with the medical field (animal and human). For example topical application of the compositions described herein may be used to inhibit and/or ameliorate topical *staph* infection. Compositions may be applied topically as a hand soap (e.g., for controlling germs beyond currently available antibacterial soaps). Compositions may be used as a medical laboratory personnel antimicrobial hand wash for cross infection and contamination inhibitor (e.g., as an instant hand sanitizer).

While previous discussions herein have concentrated on the use of bridged polycyclic compounds for treating maladies animals such as common household pets including canines and felines, theses examples should not be seen as limiting. Compositions described herein may be used to treat other animals (e.g., mammals) including, but not limited to, avian (birds), reptiles, horses, swine, sheep, goats, deer, tigers, protein producing animals (e.g., cattle), and/or lions.

In addition to felines and canines, avians may be assisted by compositions comprising bridged polycyclic compounds. Avians are susceptible to a variety of maladies, including viral infections, diseases and fungal infections. Viral infections include, but are not limited to, Psittacine Beak and Feather Disease (PBFD), Pacheco's Disease, Polyoma Virus, Psittacine Wasting Disease (Macaw wasting disease, proventricular dilation syndrome), and Pox Virus. Bacterial infections include, but are not limited to, *E. Coli*, Bacterial infections can affect any of the organ systems, yet the most common infections affect the Upper Respiratory Tract or Sinuses, the Intestinal Tract and Liver, the Urinary Tract, the Reproductive Tract, and the Skin and Feather Follicles, Psittacosis, Chlamydiosis, Ornithosis, and Parrot Fever. Fungal infections include, but are not limited to, Aspergillosis, *Candida* is a yeast that can cause infections in the mouth, crop and occasionally the rest of the intestinal tract, Cutaneous yeast infections are more difficult to treat.

Parrot fever has many names, including Chlamydiosis, Psittacosis and Ornithosis. Parrot fever is referred to as Psittacosis when it occurs in people and psittacine (parrot types) birds, and Ornithosis when it occurs in passerine (pigeons, doves, etc.) birds. Antibacterial compositions (e.g., quinolonecarboxylic acids or derivatives thereof) which may be used in combination with bridged polycyclic compounds, as well as additional uses (e.g., treatment of parrot fever), are described in U.S. Pat. No. 5,145,853 to Metzger et al., which is incorporated by reference as if fully set forth herein. In some embodiments, quinolones may be coupled to and/or combined to form a salt with bridged polycyclic compound and used to treat avian maladies.

In some embodiments, nalidixic acid (CAS Number 389-08-2) may be combined with bridged polycyclic compounds to form a composition effective in inhibiting and/or ameliorating avian maladies. The acid functionality of nalidixic acid may be used to couple nalidixic acid directly to an amine of the bridged polycyclic compound using methods known to one skilled in the art and outlined in similar examples herein. In some embodiments, multiple equivalents (e.g., eight) of commercially available nalidixic acid from Aldrich may be reacted with the freebase of 5 providing a combination antimicrobial. The combination antimicrobial may function such that the cationic cage disinfects the GI tract and the nalidixic acid is released as a systemic antimicrobial. This combination may be put, for example, into parrot food or drinking water since a lot of birds carry this disease and require quarantine+ cure before they are allowed to be sold.

There are numerous infectious diseases seen in birds. In most cases, prevention is far preferable over treatment of the disease after it occurs. Good nutrition and husbandry are the most important factors in prevention of disease. Keeping the cage clean and free of excessive fecal material and food is important in controlling bacterial infections; decaying food and feces are an ideal growth medium for bacteria which can then overwhelm the normal protective mechanisms that birds have. In some embodiments, compositions described herein may be used as a disinfectant wash and/or coating for at least portions of a bird cage to assist in inhibiting the growth of microbes.

It should be pointed out that at least some veterinarians believe that various over-the-counter antibiotics sold by pet stores are have little affect since most bacteria are resistant to them. Since these are most commonly mixed in the drinking water, accurate dosing of the birds is very difficult. In many cases the medication has a flavor which the bird dislikes, so they drink less water than they should, adding another stress factor to the already sick bird. Many veterinarians believe medicaments should be directly administered to the bird either as a oral medication directly into the mouth or crop, or as injections. For most owners it is not that difficult to learn how to give injections, and many times this is the simplest and least stressful way to medicate a bird.

Some bacterial infections that birds get are thought to be transmissible to humans. The most important bacterial agent that is a human risk is mycobacteria or tuberculosis. Birds can carry *M. tuberculosis*, the human form of tuberculosis, and *M. avium*, the avian form of tuberculosis which is transmissible to man. While these infections are not common in most species of birds, it must still be kept in mind, since these diseases are very difficult to treat and potentially devastating for both man and bird. Humans with immunosuppression due to conditions such as AIDS or cancer, should be particularly careful about exposure to birds that may be carriers of zoonotic diseases, (diseases transmissible to man). Birds with the human form of tuberculosis most likely get it directly from an infected human with which the bird had close contact. The avian form of tuberculosis can be spread from bird to bird, and it can be contagious to humans. The treatment of tuberculosis in birds is highly controversial due to the human health risk. Diagnosis of tuberculosis is difficult and frequently requires a biopsy, either from a live patient or at necropsy. Tests available for screening birds are limited to microscopic examination of the feces for the presence of the tuberculosis bacteria, and this is not very good at picking up infections.

Compositions Comprising Bridged Polycyclic Compounds for Treating Oral Diseases

All types of teeth and gum diseases can lead to serious health problems in animals and humans. Dogs and cats make much fuller use of their teeth than humans do—using them in ways humans usually use their hands. For this reason, toothache, dental disease and loss of teeth can all have serious consequences for pets. Damage to the teeth and gums in pets is permanent and irreversible.

In some embodiments, this antimicrobial may be incorporated into pet dental systems for plaque prevention (e.g. OraVet™ a clinically provided plaque prevention system (Merial, Duluth, Ga.). A system featuring a dental barrier sealant and a plaque prevention gel that can significantly reduces the formation of plaque and calculus, two factors in the onset of periodontal disease. Compositions described herein may be used, for example, for general dental oral health and preventative maintenance, dental surgery oral rinse, and/or oral infection, stomatitis.

Demanding requirements such as those for dental materials also exist in numerous other products such as coatings. Recent developments in nanotechnology are increasingly being considered to address these requirements.

A key challenge to widespread adoption of nanotechnology to such applications is the ability to manufacture non-agglomerated discrete nanoparticles that can be homogeneously distributed in resins or coatings to produce nanocomposites.

In some embodiments, a dental composition may include bridged polycyclic compounds. At least one of the bridged polycyclic compounds may include at least two cyclic groups. At least two of the cyclic groups may include quaternary ammonium or amine moieties. In some embodiments, at least two of the cyclic groups may be defined at least in part by quaternary ammonium moieties. Bridged polycyclic compounds may include any of the compounds described herein.

In some embodiments, a composition may be applied to an oral surface or at least to a portion of an oral surface. An oral surface may include at least a portion of a dental fixture.

A method may include applying a dental composition to dental fixture such as bridges, caps, retainers, dentures and any temporary or permanent dental fixture in the oral cavity. In some embodiments, a dental composition may include core-shell nanoparticles as described herein.

In some embodiments, a dental composition may include nanoparticles as described herein.

A dental composition and method of use of the same may be used in restoring the function and anatomy of a tooth. Dental compositions as described herein may be used in bonding agents, resin cements, sealants, vanishes, gels and resins. Dental compositions may include polymerizable unsaturated monomers, oligomers, prepolymers, or combinations thereof. Dental compositions may inhibit tooth decay and/or microbial growth in and around an oral cavity. Dental compositions may inhibit secondary decay.

Some commonly found bacteria leading to tooth decay and/or other oral maladies have been known for some time (e.g. *Actinomyces israelii, A viscosus, A naeslundii, Arachnia propionica, Rothia dentocariosa, Bacterionema matruchotii,* and *Corynebacterium acnes*) as described by Slack, J.M. et. al. "Identification of Actinomyces and Related Bacteria in Dental Calculus by the Fluorescent Antibody Technique" in J. Dent. Res., 1971, Vol. 50, No. (1,):78-82, 1971, incorporated by reference as if set forth fully herein. Other bacteria which lead to oral maladies may include *Streptococcus mutans, Porphymonas Gingivalis,* and *Haemophilus actinomycetemcomitans.*

In particular, stomatitis is a very common problem in felines that results in inflammation of the oral cavity and tooth loss. FORLS 'Feline Odontoclastic Resorptive Lesions' is a very common oral disease in cats and is believed to be a combination of different maladies. Bridged polycyclic compounds used in combination with or without pharmaceutically active agents may prove effective in inhibiting and/or ameliorating stomatitis and/or FORLS.

Figure 5:
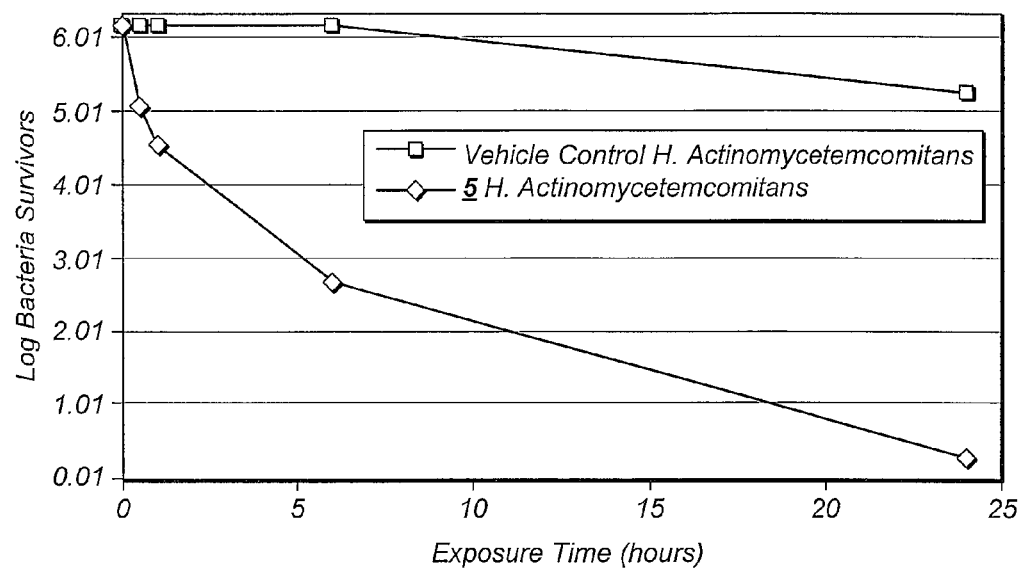
FIG. 5 depicts a graphical representation of time kill assay tests for a bridged polycyclic compound tested against *Haemophilus* Actinomycetemcomitans.
Figure 6:
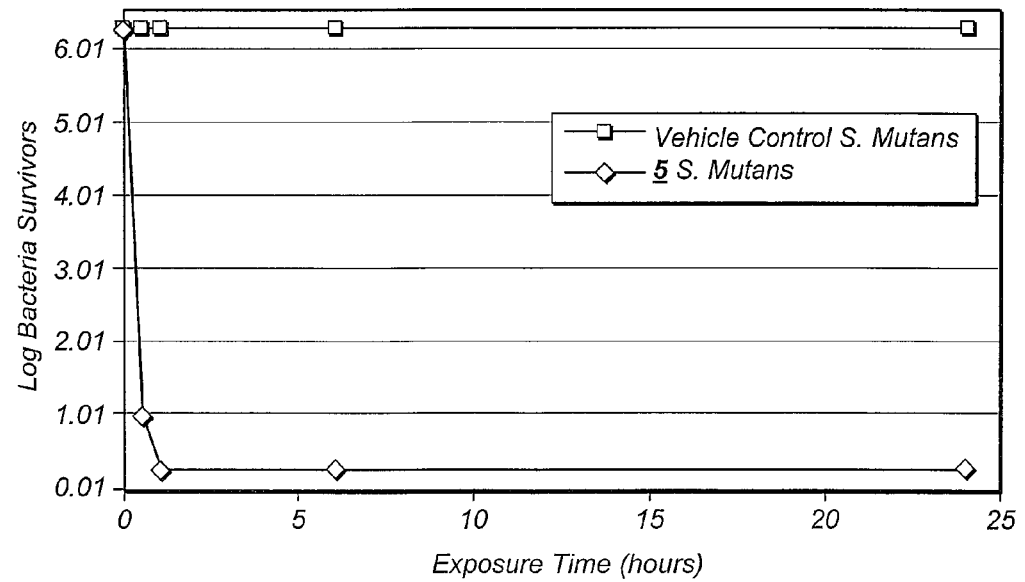
FIG. 6 depicts a graphical representation of time kill assay tests for a bridged polycyclic compound tested against *Streptococcus mutans*.
Figure 7:
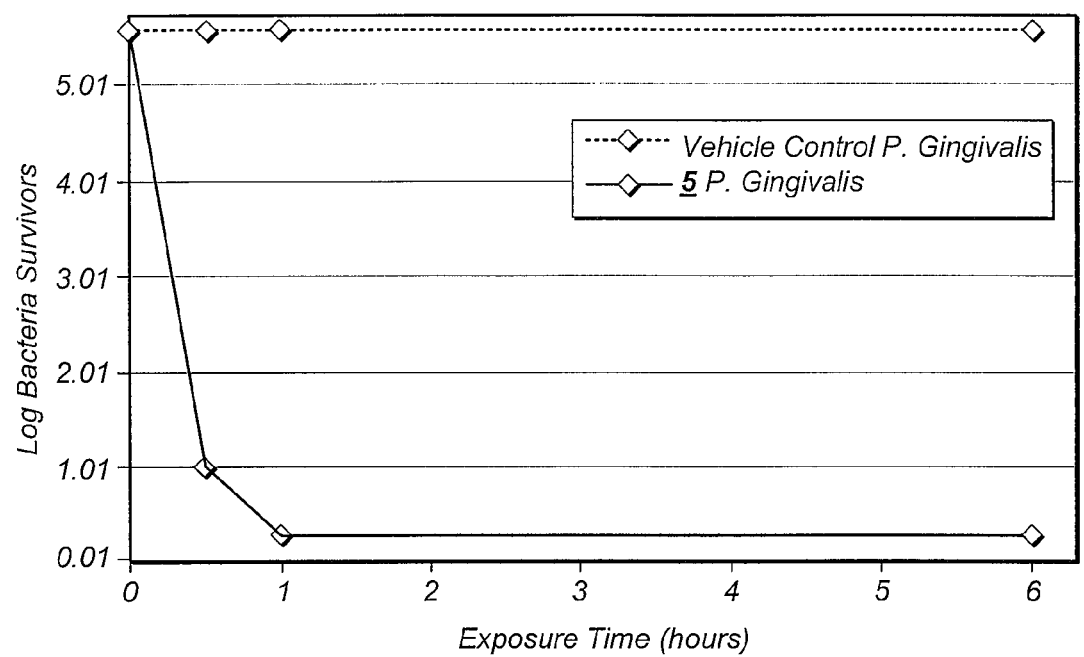
FIG. 7 depicts a graphical representation of time kill assay tests for a bridged polycyclic compound tested against Porphymonas Gingivalis.

FIGS. 1-4 depict a graphical representation of time kill assay tests for bridged polycyclic compounds (308, 309, and/or 113a) tested against *Streptococcus Mutans* and *Aspergillus niger*. FIGS. 5-7 depict a graphical representation of time kill assay tests for bridged polycyclic compound 5 tested against *Haemophilus* Actinomycetemcomitans, *Streptococcus mutans*, and Porphymonas Gingivalis respectively. The test results demonstrate how effective bridged polycyclic compounds are against known destructive microbes.

In some embodiments, dental compositions may enhance sustained antimicrobial activity with minimum harm to the living structure and surrounding tissues and without affecting the composition's restorative properties.

In some embodiments, dental compositions described herein may be used for oral trauma treatment. Dental composition may be used for oral trauma treatment field kits used for the temporary or permanent treatment of oral trauma out in the field when specialized help is not readily available.

Dental compositions may be used in combination with gelators, absorbents, and/or coagulating agents to prepare oral antimicrobial wound dressings.

Nanoparticles have been shown to enable nearly 50% reduction in filling shrinkage. These nanocomposites are suggested to be particularly useful for fabricating load bearing and cosmetic restorations. Examples of nanoparticles and general properties which they impart to dental compositions may be found in U.S. Pat. No. 6,593,395 to Angeletakis et al., which is incorporated by reference as if fully set forth herein.

A dental composite may have a high strength required for load-bearing restorations, yet maintains a glossy appearance, even after substantial wear. Through the use of particles having a mean particle size between about 0.05 micromolar and about 0.50 micromolar, the composite is useful in stress bearing restorations and in cosmetic restorations. The structural filler used is typically ground to a mean particle size of less than 0.5 micromolar and also includes a nanofiller having discrete particles of a mean particle size less than 100 nm to improve handling and mechanical characteristics. The preferred dental composites maintain their surface finish even after substantial use and also have the strength properties of hybrid composite resins.

In some embodiments, a dental composite, comprising: a polymerizable resin base; and about 10% by volume to about 80% by volume filler consisting essentially of a ground structural filler and a non-ground nanofiller, wherein the ground structural filler comprises between about 10% by volume and about 70% by volume of the composite and consists of ground particles of mean particle size between about 0.05 µm and about 0.50 µm, and wherein the ground structural filler contains less than 50% by volume of particles above 0.5 µm in diameter, and wherein the non-ground nanofiller comprises between about 1.0% by volume and about 15% by volume of the composite and consists essentially of discrete, non-aggregated gamma alumina particles having a mean particle size of about 40 nm or less.

The resin composite, in the cured form, may have a flexural strength of at least 100 MPa.

The resin composite, in the cured form, may have a flexural strength of at least 120 Mpa.

The resin base may comprise a polymerizable vinyl compound.

The ground structural filler may contain less than 10% by volume of particles above 0.8 micromolar in diameter.

The non-ground nanofiller comprises between about 5 and about 12% by volume of the composite.

The non-ground nanofiller may have a refractive index in the range of about 1.48 to about 1.6.

A dental composite comprising: a polymerizable resin base; and about 11% by volume to about 80% by volume filler in the resin base, the filler consisting essentially of a ground structural filler and a non-ground nanofiller, wherein the ground structural filler comprises between about 10% by volume and about 70% by volume of the composite and consists of ground particles having a mean particle size of between about 0.05 micromolar and about 0.50 micromolar, and wherein the non-ground nanofiller comprises between about 1.0% by volume and about 15% by volume of the composite and consists essentially of discrete, non-aggregated aluminosilicate particles having a mean particle size of less than about 100 nm, and a 1:4 molar ratio of alumina to silica.

The resin composite, in the cured form, has a flexural strength of about 120 MPa or greater.

The resin base includes a polymerizable vinyl compound.

The non-ground nanofiller comprises between about 5% by volume to about 12% by volume of the composite.

The aluminosilicate particles have a mean particle size of about 80 nm.

The resin composite, in the cured form, has a flexural strength of at least 100 MPa.

The ground structural filler contains less than 10% by volume of particles above 0.8 micromolar in diameter.

The non-ground nanofiller has a refractive index in the range of about 1.48 to about 1.6.

A dental composition may include a polymerizable compound, a polymerization initiator system, bridged polycyclic compounds, or combinations thereof. These compositions may be suitable for restoring the functionality and anatomy of a damaged tooth. Uses may include, but are not limited to, use as dental primers, adhesives, surface sealants, liners, luting cements, varnishes, impression materials, equipment and impression systems, and composite restoratives. Uses may include, but are not limited to, impression materials, coatings for impression trays, and impression systems. In some embodiments, dental compositions may impart antimicrobial activity to a contacted tooth structure and/or surrounding tissue.

The present dental compositions may include a polymerizable compound (e.g., at least one polymerizable monomer or prepolymer selected from those known in the art of dental materials) including, but not limited to, polymerizable amides, esters, alkenes, imides, acrylates, methacrylates, urethanes, vinyl esters or epoxy-based materials. Other polymerizable compounds may include those based on styrene, styrene acrylonitrile, sulfones, acetals, carbonates, phenylene ethers, phenylene sulfides, or other polymerizable units listed herein. Examples of dental compositions and additives typically used may be found in U.S. Pat. No. 6,326,417 to Jia, which is incorporated by reference as if fully set forth herein. Examples of dental compositions and additives typically used may be found in U.S. Pat. Nos. 6,500,004 to Jensen et al.; 6,326,417 to Jia; 20010009931 to Pflug et al.; 20050252413 to Kangas et al.; and 20030134933 to Jin et al. (acidic based sealants), which are incorporated by reference as if fully set forth herein.

Polymerizable compounds may include ethylenically unsaturated monomers and prepolymers and include those based on acrylic and methacylic monomers, for example those disclosed in U.S. Pat. Nos. 3,066,112 to Bowen; U.S. Pat. No. 3,179,623 to Bowen,; and U.S. Pat. No. 3,194,784 to Bowen; U.S. Pat. No. 3,751,399 to Lee et al.; and U.S. Pat. No. 3,926,906 to Lee et al.; and commonly assigned U.S. Pat. No. 5,276,068 to Wakline, which are incorporated by reference as if fully set forth herein. Methacrylate-based monomers may be used (e.g., condensation product of bisphenol A and glycidyl methacrylate, 2,2'-bis[4-(3-methacryloxy-2-hydroxy propoxy)-phenyl]-propane (BIS-GMA), dipentaerythritol pentaacrylate (DPEPA), pentaerythritol dimethacrylate (PEDM), the condensation product of ethoxylated bisphenol A and glycidyl methacrylate (EBPA-DMA), and the condensation product of 2 parts hydroxymethylmethacrylate and 1 part triethylene glycol bis(chloroformate) (PCDMA)). Polymerizable compounds may include polyurethane-based dimethacrylates (PUDMA).

Polymerizable compounds may include polymerizable diluent monomers. Such monomers are generally used to adjust the viscosity of a polymerizable composition. Suitable methacrylate-based diluent monomers may include, but are not limited to, hydroxyalkyl methacrylates (e.g., 2-hydroxyethyl methacrylate, 1,6-hexanediol dimethacrylate, and 2-hydroxypropyl methacrylate); glyceryl dimethacrylate; and ethyleneglycol methacrylates (e.g., ethyleneglycol methacrylate, diethyleneglycol methacrylate, triethyleneglycol methacrylate, Triethyleneglycol dimethacrylate, and tetraethyleneglycol methacrylate).

When used as primers, adhesives, or primer/adhesive, dental compositions may include a polymerizable compound including hydrophilic polymerizable monomers to enhance the bonding characteristics of the dental composition. Suitable polymerizable hydrophilic monomers may have carboxyl, phosphoryl, sulfonyl, and/or hydroxyl functional groups. Examples of polymerizable hydrophilic monomers having at least one carboxyl group may include, but are not limited to, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid (4-MET) and an anhydride thereof (4-META), 4-(2-hydroxy-3-methacryloyloxy) butyltrimellitic acid and an anhydride thereof, 2,3-bis (3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, an adduct of 2-hydroxyethyl methacrylate with pyromellitic dianhydride (PMDM), and an adduct of 2-hydroxyethyl methacrylate with 3,3',4,4'-benzophenonetetracarboxylic dianhydride (BTDA) or 3,3',4,4'-biphenyltetracarboxylic dianhydride. Hydrophilic monomers may include BPDM, the reaction product of an aromatic dianhydride with an excess of 2-HEMA (2-hydroxyethyl methacrylate), as disclosed in U.S. Pat. No. 5,348,988 to Suh et al., which is incorporated by reference as if fully set forth herein. Other hydrophilic monomers may include EDMT, the reaction product of 2-hydroxyethyl methacrylate (2-HEMA) with ethylene glycol bistrimellitate dianhydride; DSDM, the reaction product of 3,3',4,4'-diphenylsulfone tetracarboxylic dianhydride and 2-HEMA; PMDM, and PMGDM, the adduct of pyromellitic dianhydride with glycerol dimethacrylate.

Examples of polymerizable compounds having at least one phosphoric acid group may include, but are not limited to 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, and 2 methacryloyloxyethylphenyl acidophosphate. The phosphoric acid group in these compounds may be replaced with a thiophosphoric acid group. Examples of polymerizable compounds may include 2-methacryloyloxyethylphenyl acidophosphate and 10-methacryloyloxydecyl acidophosphate. Examples of polymerizable monomers having at least one sulfonic acid group include 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

All the above polymerizable monomers may be used alone or in combination. All of the above polymerizable compounds may be first polymerized and then added to a composition as a polymer. Polymers may be purchased. In some embodiments, a polymer may be combined with a bridged polycyclic compound to form a composition. Polymers may further polymerize during a curing process after a composition has been applied to an oral surface. In some embodiments, a polymer, added to a composition, may include poly (vinyl acetate-co-crotonic acid). A composition may include one or more solvents. Solvents may include environmentally green solvents (e.g., water, alcohol (e.g., ethanol). Solvents may be applied to an oral surface as part of a composition. At least some of the solvents may evaporate as the composition forms a film over the oral surface to which the composition was applied.

A dental composition may include a polymerization initiator system, including light curing, self-curing, dual curing, and vacuum, heat, and pressure curing systems as well as any combination thereof. Visible light curing systems employ light-sensitive compounds (e.g., benzil diketones and DL-camphorquinone) in amounts ranging from about 0.05 to 0.5 weight percent. Visible light curing systems may include polymerization accelerators (e.g., various organic tertiary amines well known in the art). In visible light curable compositions, the tertiary amines are generally acrylate derivatives such as dimethylaminoethyl methacrylate and, particularly, diethylaminoethyl methacrylate (DEAME) in amounts in the range from about 0.05 to 0.5 weight percent.

Self-curing compositions may contain free radical polymerization initiators such as, for example, peroxides in amounts ranging from about 2 to 6 weight percent. Suitable free radical initiators may include lauryl peroxide, tributyl hydroperoxide, cumene hydi-operoxide, and benzoyl peroxide. The heat and pressure curable systems also include heat cure initiators such as aromatic sulfinic acids and salts thereof, benzoyl peroxide, 1,1'-azobis (cyclohexanecarbonitrile), or other free radical initiators. Polymerization accelerators commonly used with these include tertiary amines, generally aromatic tertiary amines such as ethyl 4-(N,N-dimethyl)aminobenzoate (EDAB), dimethyl-p-toluidine, dihydroxyethyl-p-toluidine and the like, in amounts ranging from about 0.05 to about 4.0 weight percent.

The dental restorative compositions may also comprise other additives and solvents known in the art, for example, ultraviolet light absorbers, anti-oxidants such as BHT, stabilizers, fillers, pigments, opacifiers, handling agents, and others. An ultraviolet absorber may be employed in amounts ranging from about 0.05 to about 5.0 weight percent. Such ultraviolet absorbers may be desirable in the visible light curable compositions in order to avoid discoloration of the resin from any incident ultraviolet light. Suitable ultraviolet absorbers may include gelators, various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Fillers, such as colloidal silica, barium glasses, fibrous fillers, quartz, ceramic fillers and the like may also be incorporated into dental compositions, particularly when they are to be used as bonding agents, luting cements or filling composites. Suitable fillers may include fillers conventionally used in the dental industry capable of being covalently bonded to the resin matrix itself or to a coupling agent which is covalently bonded to both. Silane coupling agents are known, for example methacryloxypropyl trimethoxy silane. Such fillers are described in U.S. Pat. Nos. 4,544,359 and 4,547,531 to Waknine, which are incorporated by reference as if fully set forth herein. Examples of suitable filling materials may include, but are not limited to, amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof. Particularly suitable fillers for dental filling-type materials prepared are those having a particle size in the range from about 0.1 to about 5.0 microns, together with a silicate colloid having particle sizes in the range from about 0.001 to about 0.07 microns.

Antimicrobials may be generally effective against organisms which cause secondary decay, and must not adversely affect the required physical properties of the cured compositions, in particular water sorption, diametral tensile strength, and hardness. In particular, the ADA specification No. 27 requires dental resin composites to have water sorption values below 50 $\mu g/mm^3$/week. Commercial dental restorative materials used as, filling materials preferably have water sorption values of less than about 30, less than about 20, or less than about 15 $\mu g/mm^3$/week. The ADA specification No. 27 specifies that the diametrical tensile strength for filled dental composite (type II) should be a minimum of 34 MPa. Commercial dental restorative materials used as filling materials may have DTS values of greater than about 38, greater than about 40, or greater than about 45 MPa. Dentine bonding strength must be at least about 10 MPa, at least about 15 MPa, at least about 18 MPA, or at least about 20 MPa.

Dental compositions may be used as bonding primers or adhesives. When dental compositions are to be used as bonding primers, adhesives, or primer/adhesives, volatile solvents such as water, alcohol, acetone, and the like are used to dilute the polymerizable compound(s). The particular amounts of polymerizable compound(s) and solvent may be adjusted so as to provide sufficient viscosity such that they can be applied in one or a relatively few number of coats and achieve a uniform thin coating, of the dental substrate, while providing high bonding strengths between the dental substrate and the restorative material or dental component. Optionally, additional polymerizable compounds, optional self-life stabilizers, or other modifying ingredients known in the art may be incorporated.

Dental compositions may be used as a bonding agent and/or base liner under restorative materials such as resin composites, silver amalgam alloys, and the like.

The most common ailments seen by vets in dogs and cats are dental problems. More than half of all pets suffer from gum disease, dental calculus or similar dental problems.

Calculus is the brown build-up of plaque found extending downwards on the tooth from the gum line. Calculus is a haven for bacteria which can have serious consequences for your pet's general health. These bacteria can not only cause abscesses and tooth loss but can have effects further afield—even resulting in organ damage as the bacteria are carried from the mouth, through the bloodstream.

Dental compositions may be used as dental luting cements and/or cavity filling materials.

In some embodiments, elements used within an antimicrobial coatings as described herein is association with other applications or elsewhere herein (e.g., under the "Matrices" heading) may also be incorporated into a composition for dental purposes.

EXAMPLES

Having now described the invention, the same will be more readily understood through reference to the following example(s), which are provided by way of illustration, and are not intended to be limiting of the present invention.

General Experimental: All manipulations were carried out with strict exclusion of air and water using Schlenk technique. Dimethylformamide (DMF), 99.8%, anhydrous, was purchased from Acros Organics. Ethanol, denatured, was purchased from EMD. Methanol, low water, was purchased from J. T. Baker. Dichloromethane, anhydrous, and ethyl acetate, anhydrous, were purchased from Aldrich. They were used without further purification. Octa-amine 1 was synthesized as described in AllAccem, Inc. patents. Ethylenediamine, 3-(dimethylamino)-1-propylamine and benzyl bromide were purchased from Aldrich. Ethylenediamine, triethylamine and methylacrylate were purchased from Aldrich and distilled before use. Methyl iodide and 1-bromohexane were purchased from Acros Organics. They were distilled before use. Succinic anhydride was purchased from Fluka Organics and 1,6-hexanediamine was purchased from Aldrich. They were sublimed before use. Sodium bicarbonate was purchased from J. T. Baker. Sulfuric acid was purchased from EMD. They were used without further purification. Also purchased from Aldrich were phosphorous pentoxide, powder, sodium dicyanamide and 4-sulfophenyl isothiocyanate sodium salt monohydrate. They were used without further purification. Nonenylsuccinic anhydride was purchased from Aldrich and dried under vacuum in a desiccator over P2O5 for more than 3 days. Also purchased from Aldrich were 5-aminoisophthalic acid and 4-amino-2,7-napthadisulfonic acid and used without purification. NMR analysis was performed on a JEOL Eclipse+400 instrument at Acorn NMR, Inc. in Livermore, Calif. MS analysis was performed at Scripps Center for Mass Spectrometry in La Jolla, Calif.

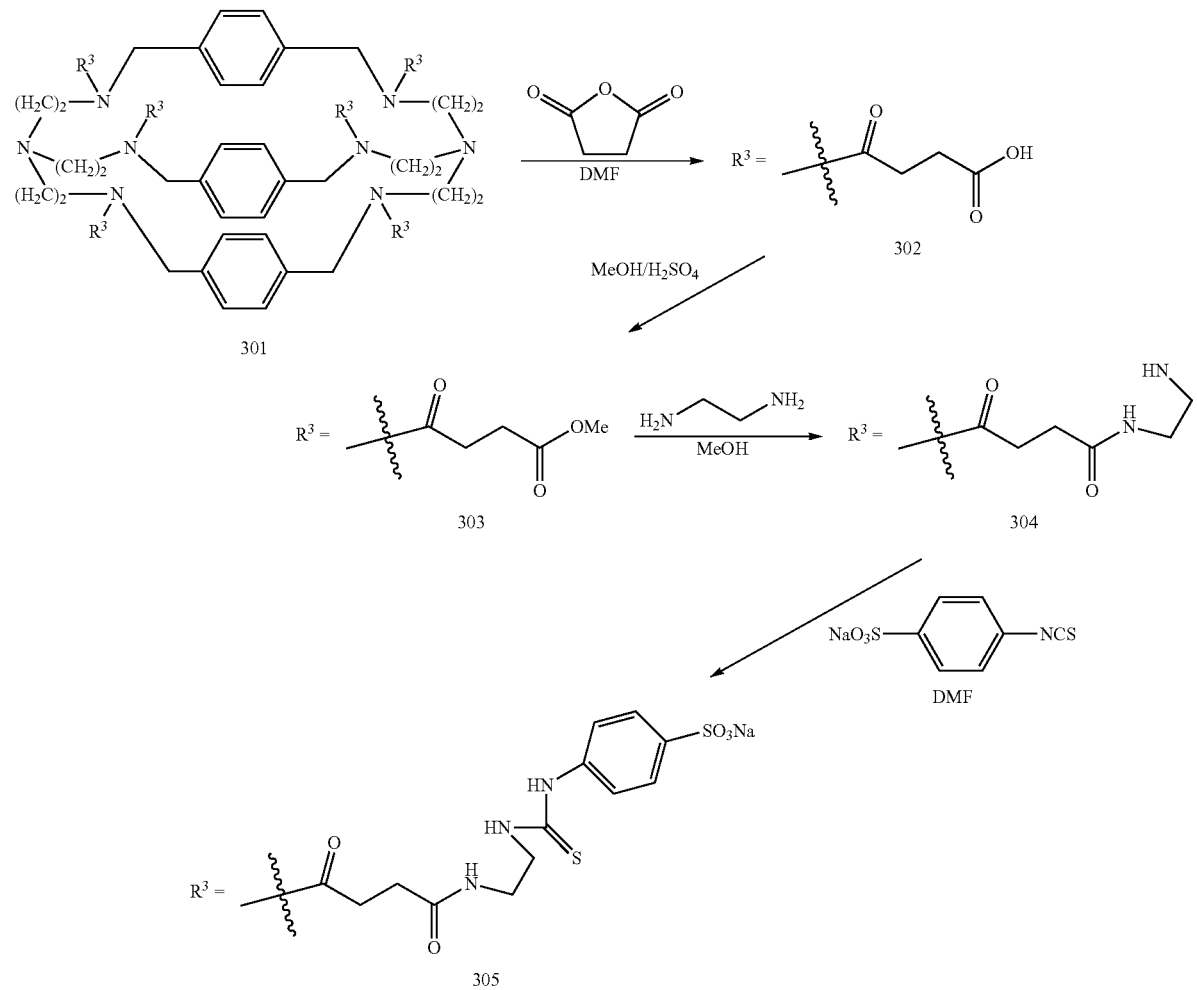

Synthesis of 302 and 303: To a 100 mL flask was added 301 (1.06 g, 1.75 mmoles) and succinic anhydride (1.05 g, 10.5 mmoles) followed by DMF (8.75 mL). The system was closed and the reaction solution was heated in an oil bath at 80° C. for 14 h. Then the volatiles were removed by vacuum transfer leaving a colorless foam that was crushed to a powder. That powder was combined with methanol (42.5 mL, 33.6 g, 1.05 mole) and concentrated sulfuric acid (0.292 mL, 5.25 mmoles) added. The reaction flask was fitted with a reflux condenser and the reaction solution was heated with a 95° C. oil bath for 14 h. Then the reaction solution was cooled to room temperature and sodium bicarbonate (0.588 g, 7.00 mmoles) was added. The reaction solution was stirred at room temperature for 3 h. Then the volatiles were removed by vacuum transfer to leave a white paste. The paste was extracted with dichloromethane (1×10 mL and 3×4 mL) and filtered. The volatiles were removed from the filtrate to leave the product 303 as a colorless powder (1.85 g, 1.44 mmoles, 82.5% yield). Analysis of 302: $^1$H NMR (400 MHz, DMSO-$d_6$, δ): 2.05-2.25, 2.45-2.65, 2.95-3.15 (m, 48H, N[$H_2CH_2N$(COCH$_2$CH$_2$CO$_2$H)CH$_2$C$_6$H$_4$CH$_2$N(COCH$_2$CH$_2$CO$_2$H)

CH$_2$CH$_2$]$_3$N), 4.30-4.65 (m, 12H, N[CH$_2$CH$_2$N (COCH$_2$CH$_2$CO$_2$H)CH$_2$C$_6$H$_4$CH$_2$N(COCH$_2$CH$_2$CO$_2$H) CH$_2$CH$_2$]$_3$N), 7.05-7.25 (m, 12H, N[CH$_2$CH$_2$N (COCH$_2$CH$_2$CO$_2$H)CH$_2$C$_6$H$_4$CH$_2$N(COCH$_2$CH$_2$CO$_2$H) CH$_2$CH$_2$]$_3$N), 12.06 (s, 6H, N[CH$_2$CH$_2$N (COCH$_2$CH$_2$CO$_2$H)CH$_2$C$_6$H$_4$CH$_2$N(COCH$_2$CH$_2$CO$_2$H) CH$_2$CH$_2$]$_3$N). ESI-MS (m/z): [M]$^+$ 1200, [M]2+ 600. (MS data from 005-077) Analysis of 303: $^1$H NMR (400 MHz, Methanol-d$_4$, δ): 1.8-2.35, 2.50-2.93 (m, 36H, N[CH$_2$CH$_2$N (COCH$_2$CH$_2$CO$_2$Me)CH$_2$C$_6$H$_4$CH$_2$N(COCH$_2$CH$_2$CO$_2$Me) CH$_2$CH$_2$]$_3$N), 3.05-3.30 (m, 12H, N[CH$_2$CH$_2$N (COCH$_2$CH$_2$CO$_2$Me)CH$_2$C$_6$H$_4$CH$_2$N(COCH$_2$CH$_2$CO$_2$Me) CH$_2$CH$_2$]$_3$N), 3.65-3.71 (m, 18H, N[CH$_2$CH$_2$N (COCH$_2$CH$_2$CO$_2$Me)CH$_2$C$_6$H$_4$CH$_2$N(COCH$_2$CH$_2$CO$_2$Me) CH$_2$CH$_2$]$_3$N), 4.35-4.80 (m, 12H, N[CH$_2$CH$_2$N (COCH$_2$CH$_2$CO$_2$Me)CH$_2$C$_6$H$_4$CH$_2$N(COCH$_2$CH$_2$CO$_2$Me) CH$_2$CH$_2$]$_3$N), 7.13-7.43 (m, 12H, N[CH$_2$CH$_2$N (COCH$_2$CH$_2$CO$_2$Me)CH$_2$C$_6$H$_4$CH$_2$N(COCH$_2$CH$_2$CO$_2$Me) CH$_2$CH$_2$]$_3$N). ESI-MS (m/z): [M+Na]$^+$ 1306, [M]$^+$1284, [M]$^{2+}$ 642.

Synthesis of 304: To a 100 ml flask was added 303 (4.12 g, 3.21 mmoles) followed by methanol (10.7 mL). Then to a separate flask ethylenediamine (38.7 mL, 34.7 g, 578 mmoles) was added followed by methanol (19.3 mL). Both solutions were cooled in brine baths at −3 to −5° C. and the solution of 303 was added to the solution of ethylenediamine drop-wise over 5 minutes. The flask that had contained the solution of 303 was rinsed with methanol (3×2 mL) and the reaction solution allowed to warm to room temperature slowly as the ice melted. It was stirred for 14 h. Then the reaction flask was heated with a 50° C. oil bath for 1 day. The reaction solution was cooled to room temperature and the volatiles removed by vacuum transfer leaving a colorless foam that was crushed to a powder. The powder was subjected to vacuum of <20 mtorr while the flask was heated in a 50° C. oil bath for 1 day. Then the flask was placed in a desiccator with phosphorous pentoxide under static vacuum for 3 days. The product is a colorless powder (4.06 g, 2.80 mmoles, 87.0% yield). Analysis of 304: $^1$H NMR (400 MHz, D$_2$O, δ): 2.15-2.85 (m, 48H, N[CH$_2$CH$_2$N (COCH$_2$CH$_2$CONHCH$_2$CH$_2$NH$_2$)CH$_2$C$_6$H$_4$CH$_2$N (COCH$_2$CH$_2$CONHCH$_2$CH$_2$NH$_2$) CH$_2$CH$_2$]$_3$N), 3.07-3.45 (m, 30H, N[CH$_2$CH$_2$N(COCH$_2$CH$_2$CONHCH$_2$CH$_2$NH$_2$) CH$_2$C$_6$H$_4$CH$_2$N(COCH$_2$CH$_2$CONHCH$_2$CH$_2$NH$_2$) CH$_2$CH$_2$]$_3$N), 4.30-4.70 (m, 12H, N[CH$_2$CH$_2$N (COCH$_2$CH$_2$CONHCH$_2$CH$_2$NH$_2$)CH$_2$C$_6$H$_4$CH$_2$N (COCH$_2$CH$_2$CONHCH$_2$CH$_2$NH$_2$)CH$_2$CH$_2$]$_3$N), 7.05-7.38 (m, 12H, N[CH$_2$CH$_2$N(COCH$_2$CH$_2$CONHCH$_2$CH$_2$NH$_2$) CH$_2$C$_6$H$_4$CH$_2$N(COCH$_2$CH$_2$CONHCH$_2$CH$_2$NH$_2$) CH$_2$CH$_2$]$_3$N). ESI-MS (m/z): [M]$^+$ 1452, [M]$^{2+}$ 726 and [M]$^{3+}$ 485.

Synthesis of 305: To a 50 mL flask was added 304 (1.20 g, 0.826 mmoles) and DMF (3.4 mL). Then one third of the total amount of 4-sulfophenyl isothiocyanate sodium salt mono- hydrate (1.39 g, 5.45 mmoles) was added and the reaction solution stirred for 15 minutes. The second third of 4-sul- fophenyl isothiocyanate sodium salt monohydrate was added followed by DMF (1.0 mL) and the reaction solution stirred for another 15 minutes. Then the last third of 4-sulfophenyl isothiocyanate sodium salt monohydrate was added followed by DMF (1.0 μL) and the reaction solution stirred for 2 h while on a 25° C. water bath. The volatiles were removed from the reaction solution by vacuum transfer leaving an off-white paste. The paste was dissolved in water (5 mL) and the product precipitated with ethanol (30 mL). The solution was filtered leaving the precipitate. It was dissolved in water (4 mL), precipitated with ethanol (30 mL) and the solution filtered leaving the precipitate. It was dissolved in water (3 mL), precipitated with ethanol (30 mL) and filtered leaving the precipitate. This step, dissolution in with water (3.0 mL), precipitation with ethanol (30 mL) and filtration, was pre- formed again. Then the product was placed under vacuum for 14 h while on a 25° C. water bath. Finally, the product was dissolved in water (5 mL), filtered and the volatiles removed from the filtrate. The resulting paste was placed under vacuum for 14 h while on a 25° C. bath and the product isolated as a white powder (0.691 g, 0.240 mmoles, 29.1% yield un-optimized). Analysis of 305: $^1$H NMR (400 MHz, D$_2$O, δ): 1.89-2.94 (m, 48H, N[CH$_2$CH$_2$N (COCH$_2$CH$_2$CONHCH$_2$CH$_2$NHCSNHC$_6$H$_4$SO$_3$Na) CH$_2$C$_6$H$_4$CH$_2$N (COCH$_2$CH$_2$CONHCH$_2$CH$_2$NHCSNHC$_6$H$_4$SO$_3$Na) CH$_2$CH$_2$]$_3$N), 2.95-3.90 (m, 42H, N[CH$_2$CH$_2$N (COCH$_2$CH$_2$CONHCH$_2$CH$_2$NHCSNHC$_6$H$_4$SO$_3$Na) CH$_2$C$_6$H$_4$CH$_2$N (COCH$_2$CH$_2$CONHCH$_2$CH$_2$NHCSNHC$_6$H$_4$SO$_3$Na) CH$_2$CH$_2$]$_3$N), 4.15-4.68 (m, 12H, N[CH$_2$CH$_2$N (COCH$_2$CH$_2$CONHCH$_2$CH$_2$NHCSNHC$_6$H$_4$SO$_3$Na) CH$_2$C$_6$H$_4$CH$_2$N (COCH$_2$CH$_2$CONHCH$_2$CH$_2$NHCSNHC$_6$H$_4$SO$_3$Na) CH$_2$CH$_2$]$_3$N), 6.93-7.25 (m, 12H, N[CH$_2$CH$_2$N (COCH$_2$CH$_2$CONHCH$_2$CH$_2$NHCSNHC$_6$H$_4$SO$_3$Na) CH$_2$C$_6$H$_4$CH$_2$N (COCH$_2$CH$_2$CONHCH$_2$CH$_2$NHCSNHC$_6$H$_4$SO$_3$Na) CH$_2$CH$_2$]$_3$N), 7.25-7.43, 7.68-7.84 (m, 24H, NHC$_6$H$_4$SO$_3$Na).

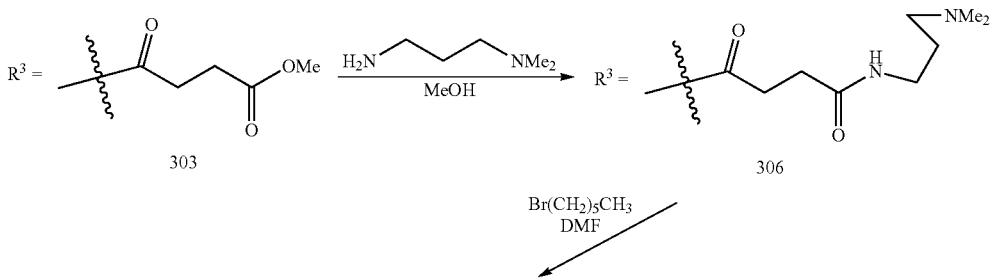

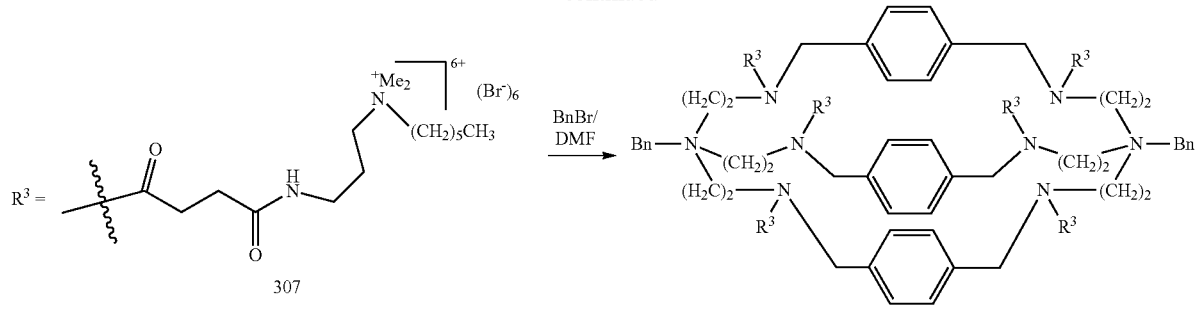

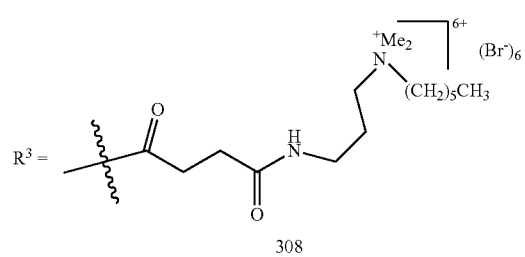

Synthesis of 306: To a 5 mL flask was added 3 (0.503 g, 0.392 mmoles) followed by methanol (0.89 mL) and 3-(dimethylamino)-1-propylamine (1.77 mL, 1.44 g, 14.1 mmoles). The reaction flask was fitted with a reflux condenser and an 80° C. oil bath was used to heat the reaction solution for 2 days. Then after cooling to room temperature the volatiles were removed by vacuum transfer and the resulting colorless foam crushed to a powder. The product was put under vacuum for 14 h while the flask was heated in a 50° C. bath. Finally, the product was placed into a vacuum desiccator with phosphorous pentoxide under static vacuum for 3 days. The product is a colorless powder (0.536 g, 0.315 mmoles, 80.2% yield) Analysis of 306: $^1$H NMR (400 MHz, Methanol-$d_4$, δ): 1.64-1.75 (m, 12H, N[CH$_2$CH$_2$N(COCH$_2$CH$_2$CONHCH$_2$CH$_2$CH$_2$NMe$_2$)CH$_2$C$_6$H$_4$CH$_2$N(COCH$_2$CH$_2$CONHCH$_2$CH$_2$CH$_2$NMe$_2$)CH$_2$CH$_2$]$_3$N), 1.96-2.86 (m, 96H, N[CH$_2$CH$_2$N(COCH$_2$CH$_2$CONHCH$_2$CH$_2$CH$_2$NMe$_2$)CH$_2$C$_6$H$_4$CH$_2$N(COCH$_2$CH$_2$CONHCH$_2$CH$_2$CH$_2$NMe$_2$)CH$_2$CH$_2$]$_3$N), 3.05-3.28 (m, 18H, N[CH$_2$CH$_2$N(COCH$_2$CH$_2$CONHCH$_2$CH$_2$CH$_2$NMe$_2$)CH$_2$C$_6$H$_4$CH$_2$N(COCH$_2$CH$_2$CONHCH$_2$CH$_2$CH$_2$NMe$_2$)CH$_2$CH$_2$]$_3$N), 4.35-4.82 (m, 12H, N[CH$_2$CH$_2$N(COCH$_2$CH$_2$CONHCH$_2$CH$_2$CH$_2$NMe$_2$)CH$_2$C$_6$H$_4$CH$_2$N(COCH$_2$CH$_2$CONHCH$_2$CH$_2$CH$_2$NMe$_2$)CH$_2$CH$_2$]$_3$N), 7.05-7.45 (m, 12H, N[CH$_2$CH$_2$N(COCH$_2$CH$_2$CONHCH$_2$CH$_2$CH$_2$NMe$_2$)CH$_2$CH$_4$CH$_2$N(COCH$_2$CH$_2$CONHCH$_2$CH$_2$CH$_2$NMe$_2$)CH$_2$CH$_2$]$_3$N). ESI-MS (m/z): [M]$^+$ 1705, [M]$^{2+}$ 853, [M]$^{3+}$ 569, [M]$^{4+}$ 427. (MS data from 006-153)

Synthesis of 308: To a 15 μL round bottom flask was added 6 (0.491 g, 0.288 mmoles), DMF (0.24 mL) and 1-bromohexane (0.643 mL, 0.756 g, 4.61 mmoles). The reaction flask was heated in a 95° C. oil bath for about 20 h. Then the reaction solution was cooled to room temperature and DMF (0.05 mL) and benzyl bromide (0.206 mL, 0.296 g, 1.73 mmoles) were added. The reaction flask was heated with an 80° C. oil bath for about 14 h. Then the reaction solution was cooled to room temperature, DMF (8 mL) was added. The product was precipitated by addition of ethyl acetate (24 mL) and the solution filtered. The precipitate was washed with ethyl acetate (2×24 mL) and the volatiles removed by vacuum transfer to leave a white powder (0.862 g, 0.285 mmoles, 98.8% yield). In this example 7 was not isolated. Analysis of 7 was obtained from a reaction stopped before synthesis of 8. Analysis of 307: ESI-MS (m/z): [M-2Br]$^{2+}$ 1267, [M-3Br]$^{3+}$ 818, [M-4Br]$^{4+}$ 594, [M-5Br]$^5$+459. Analysis of 308: ESI-MS (m/z): [M-3Br+Na]$^{3+}$ 940, [M-4Br+Na]$^{4+}$ 685.

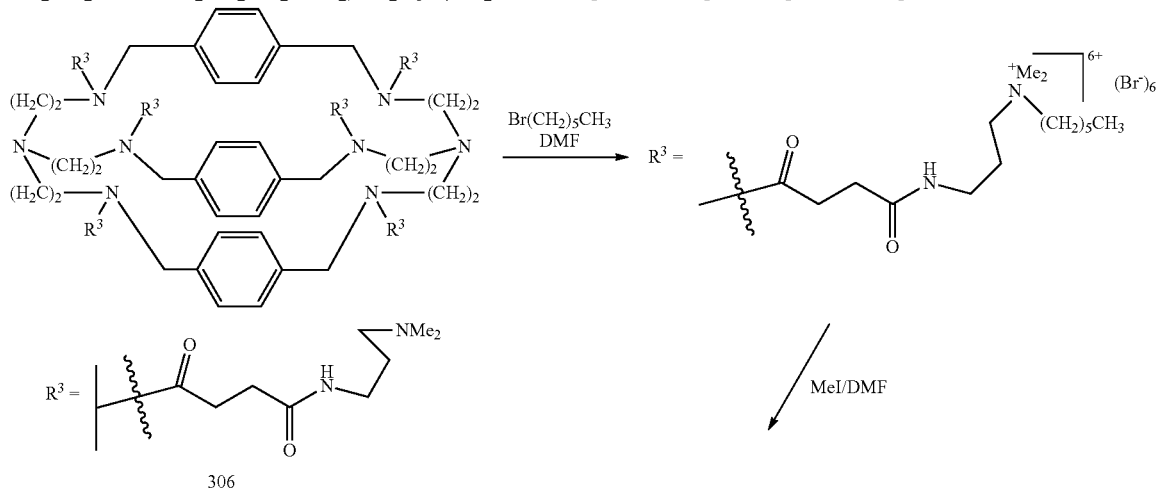

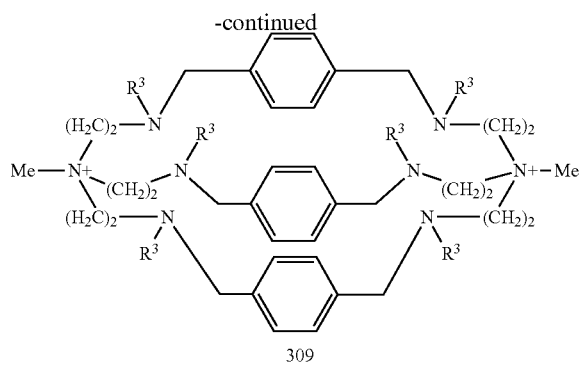

309

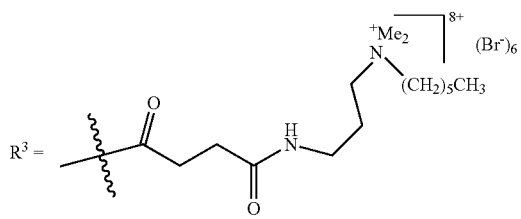

Synthesis of 309: To a 25 mL round bottom flask was added 306 (0.550 g, 0.323 mmoles) followed by DMF (0.27 mL) and 1-bromohexane (0.725 mL, 0.854 g, 5.17 mmoles). The flask was heated with a 95° C. oil bath for about 16 h and then cooled to room temperature. Then DMF (3.0 mL) was added followed by methyl iodide (0.121 mL, 0.275 g, 1.94 mmoles) and the reaction flask heated with an 80° C. oil bath for about 14 h. Then the reaction solution was cooled to room temperature and the product precipitated by addition of ethyl acetate (15 mL). After filtration the precipitate was washed with ethyl acetate (2×15 mL). After removal of the volatiles by vacuum transfer the product was isolated as a slightly off white powder (0.853 g, 0.286 mmoles, 88.5% yield). In this experiment 307 was not isolated. Analysis of 307 was obtained from a reaction stopped before synthesis of 309. Analysis of 307: ESI-MS (m/z): [M-2Br]$^{2+}$ 1267, [M-3Br]$^{3+}$ 818, [M-4Br]$^{4+}$ 594, [M-5Br]$^{5+}$+459. Analysis of 309: ESI-MS (m/z): [M-2I—Br]$^{3+}$ 882, [M-2I—Br+Na]$^{3+}$ 890, [M-I-2Br]$^{3+}$ 897, [M-2I—Br+2Na]$^{3+}$ 897.

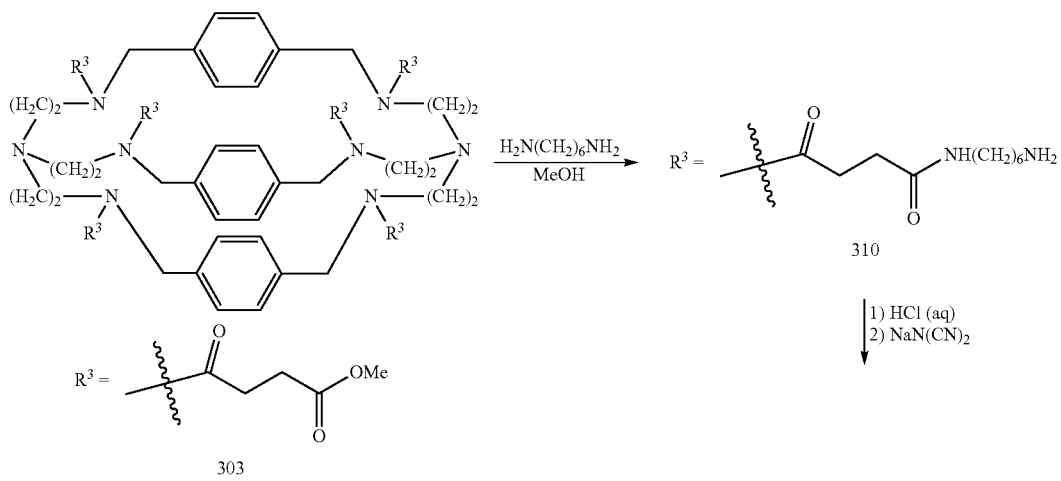

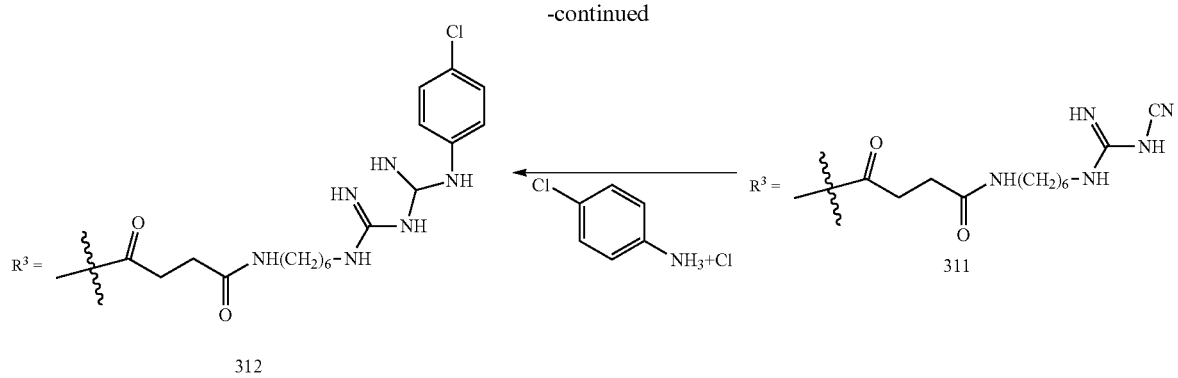

312

Synthesis of 310: To a 50 mL flask was added 1,6-hexanediamine (3.12 g, 26.9 mmoles) and methanol (1.60 mL). The reaction flask was cooled in a brine/ice bath and 303 (0.575 g, 0.448 mmoles) was added. The reaction solution was allowed to warm to room temperature slowly as the ice melted. It was stirred for 14 h. Then the water bath was replaced by a 50° C. oil bath and the reaction flask heated for 4 h. Following that, the oil bath temperature was increased to 70° C. and the reaction solution heated for 1 day. Then the reaction solution was cooled to room temperature and transferred to a sublimation apparatus. After the volatiles were removed by vacuum transfer, excess 1,6-hexanediamine was removed by sublimation using an oil bath temperature of 70° C. with pressure of <20 mtorr. The sublimation was performed for 2 days and the cold finger was cleaned between days of sublimation. The product was a colorless foam that was crushed to a powder (0.492 g, 0.275 mmoles, 61.4% yield un-optimized). Analysis of 310: $^1$H NMR (400 MHz, Methanol-$d_4$, δ): 1.28-1.42, 1.43-1.58 (m, 48H, N[CH$_2$CH$_2$N (COCH$_2$CH$_2$CONHCH$_2$(CH$_2$)$_4$CH$_2$NH$_2$)CH$_2$C$_6$H$_4$CH$_2$N (COCH$_2$CH$_2$CONHCH$_2$(CH$_2$)$_4$CH$_2$NH$_2$)CH$_2$CH$_2$]$_3$N), 1.96-2.35, 2.42-2.80 (m, 60H, N[CH$_2$CH$_2$N (COCH$_2$CH$_2$CONHCH$_2$(CH$_2$)$_4$CH$_2$NH$_2$)CH$_2$C$_6$H$_4$CH$_2$N (COCH$_2$CH$_2$CONHCH$_2$(CH$_2$)$_4$CH$_2$NH$_2$)CH$_2$CH$_2$]$_3$N), 3.37-3.36 (m, 18H, N[CH$_2$CH$_2$N(COCH$_2$CH$_2$CONHCH$_2$ (CH$_2$)$_4$CH$_2$NH$_2$)CH$_2$C$_6$H$_4$CH$_2$N(COCH$_2$CH$_2$CONHCH$_2$ (CH$_2$)$_4$CH$_2$NH)CH$_2$CH$_2$]$_3$N), 4.34-5.67 (m, 12H, N[CH$_2$CH$_2$N(COCH$_2$CH$_2$CONHCH$_2$(CH$_2$)$_4$CH$_2$NH$_2$) CH$_2$C$_6$H$_4$CH$_2$N(COCH$_2$CH$_2$CONHCH$_2$(CH$_2$)$_4$CH$_2$NH$_2$) CH$_2$CH$_2$]$_3$N), 7.08-7.42 (m, 12H, N[CH$_2$CH$_2$N (COCH$_2$CH$_2$CONHCH$_2$(CH$_2$)$_4$CH$_2$NH$_2$)CH$_2$C$_6$H$_4$CH$_2$N (COCH$_2$CH$_2$CONHCH$_2$(CH$_2$)$_4$CH$_2$NH$_2$)CH$_2$CH$_2$]$_3$N). ESI-MS (m/z): [M]$^+$ 1789, [M+Na]$^+$ 1811, [M]$^{2+}$ 895, [M]$^{3+}$ 597, [M]$^{4+}$ 448

Synthesis of 311: To a 5 mL flask was added 310 (0.0673 g, 0.0376 mmoles), dilute hydrochloric acid (0.075 mL, 0.53 mmoles, 7.0 M) and sodium dicyanamide, 96%, (0.021 g, 0.226 mmoles). The solution was stirred on a 90° C. oil bath for 20 minutes before water (0.075 mL) was added. Then the reaction was stirred a 90° C. oil bath for 14 h. The solution was cooled to RT and the volatiles removed by vacuum transfer to leave a white solid. Analysis of 311: ESI-MS (m/z): [M+Na+3NaCl]$^{3+}$ 796, [M+Na+3 NaCl]$^{4+}$ 597.

Synthesis of a Bridged Polycyclic Compound Including Pharmaceutically Active Agents and Intermediates Directed Towards Such Compounds:

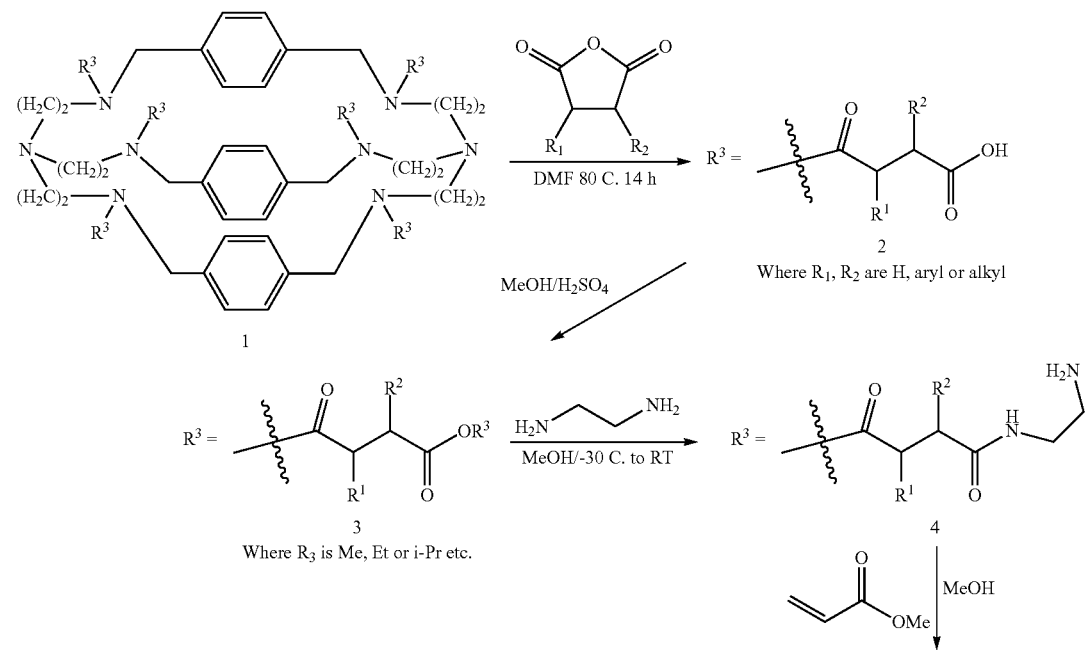

Where $R_1$, $R_2$ are H, aryl or alkyl

Where $R_3$ is Me, Et or i-Pr etc.

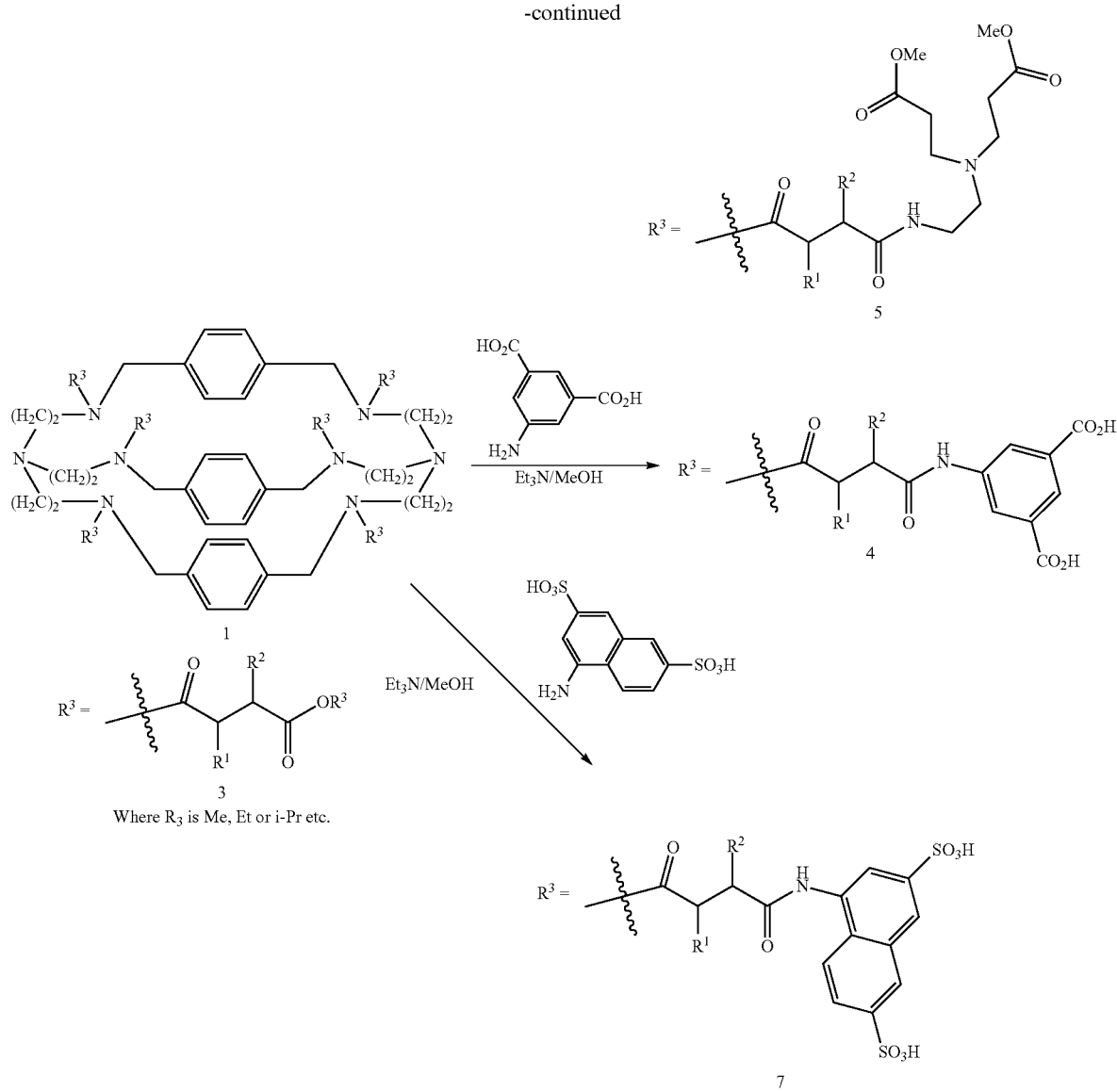

Synthesis of 2 and 3: (where $R_1$ and $R_2$=H and $R_3$=Me): To a 50 mL RBF was added 1 (1.39 g, 2.32 mmoles) and succinic anhydride (1.39 g, 13.9 mmoles) followed by DMF (2.9 mL) and the solution heated on an oil bath at 80° C. for 14 h. Then the reaction solution was cooled to RT and volatiles were removed by vacuum transfer to a pressure of less than 20 mtorr. The product was then taken to the next reaction. Analysis of 2 was obtained from a sample removed at this point. Product 2 was dissolved in methanol (56.4 mL, 44.6 g, 1.39 moles) which formed a semi-waxy, semi-solid solution. Then concentrated sulfuric acid was added (0.387 mL, 6.96 mmoles) and the reaction flask fitted with a reflux condenser. The flask was heated on an oil bath set to 70° C. for 14 h and cooled to RT. Then $NaHCO_3$ was added (0.800 g, 9.28 nmoles) and the reaction solution stirred at room temperature for 3 h. The solution was filtered and the volatiles removed from the filtrate to produce the product as a white slightly waxy solid. Analysis of 2: $^1H$ NMR (400 MHz, DMSO-$d_6$, δ): 2.05-2.30, 2.45-2.60, 3.0-3.15 (m, 48H, N[$CH_2CH_2N$ ($COCH_2CH_2CO_2H$)$CH_2C_6H_4CH_2N(COCH_2CH_2CO_2H)$ $CH_2CH_2]_3N$), 4.30-4.65 (m, 12H, N[$CH_2CH_2N$ ($COCH_2CH_2CO_2H$)$CH_2C_6H_4CH_2N(COCH_2CH_2CO_2H)$ $CH_2CH_2]_3N$), 7.05-7.25 (m, 12H, N[$CH_2CH_2N$ ($COCH_2CH_2CO_2H$)$CH_2C_6H_4CH_2N(COCH_2CH_2CO_2H)$ $CH_2CH_2]_3N$), 12.06 (s, 6H, N[$CH_2CH_2N$ ($COCH_2CH_2CO_2H$)$CH_2C_6H_4CH_2N(COCH_2CH_2CO_2H)$ $CH_2CH_2]_3N$).

ESI-MS (m/z): $[M+H]^+$ 1200, $[M+2H]^{2+}$ 600. Analysis of 3: $^1H$ NMR (400 MHz, Methanol-$d_4$, δ): 1.8-2.35, 2.50-2.93 (m, 36H, N[$CH_2CH_2N(COCH_2CH_2CO_2Me)$ $CH_2C_6H_4CH_2N(COCH_2CH_2CO_2Me)CH_2CH_2]_3N$), 3.05-3.30 (m, 12H, N[$CH_2CH_2N(COCH_2CH_2CO_2Me)$ $CH_2C_6H_4CH_2N(COCH_2CH_2CO_2Me)CH_2CH_2]_3N$), 3.66-3.71 (m, 18H, N[$CH_2CH_2N(COCH_2CH_2CO_2Me)$ $CH_2C_6H_4CH_2N(COCH_2CH_2CO_2Me)CH_2CH_2]_3N$), 4.35-4.70 (m, 12H, N[$CH_2CH_2N(COCH_2CH_2CO_2Me)$ $CH_2C_6H_4CH_2N(COCH_2CH_2CO_2Me)CH_2CH_2]_3N$), 7.15-7.45 (m, 12H, N[$CH_2CH_2N(COCH_2CH_2CO_2Me)$ $CH_2C_6H_4CH_2N(COCH_2CH_2CO_2Me)CH_2CH_2]_3N$).

ESI-MS (m/z): $[M+Na]^+$ 1306, $[M+H]^+$ 1284, $[M+2H]^{2+}$ 642.

Synthesis of 4: (where $R_1$ and $R_2$=H): Hexa-ester 3 (0.241 g, 0.188 mmoles, where R=Me) was added to a 50 mL flask and dissolved in methanol (0.19 mL). Then the reaction flask was cooled in an ice/brine bath that had reached −5 to −8° C. before addition of diaminoethylene (2.26 mL, 2.03 g, 33.8 mmoles) in methanol (1.13 mL) already chilled to about −5° C. The addition occurred over about 2 minutes and the resulting reaction solution was allowed to warm to RT overnight with stirring. After 3 days at RT the volatiles were removed by vacuum transfer to a pressure of less than 20 mtorr leaving a clear colorless oil. To that oil methanol (20 mL) and 1-butanol (10 mL) were added and after mixing thoroughly the volatiles removed by vacuum transfer to a pressure of less than 20 mtorr. The methanol/1-butanol azeotrope/vacuum transfer cycle was performed an additional two times and the product isolated as a clear colorless brittle glass. Analysis of 4: ESI-MS (m/z): $[M+H]^+$ 1452, $[M+2H]^{2+}$ 726 and $[M+H]^{3+}$ 485.

Synthesis of 5: (where $R_1$ and $R_2$=H) Hexa-amine 4 (0.273 g, 0.188 mmoles) was dissolved in methanol (2.2 mL) and the reaction flask was cooled in an ice water bath. Then freshly distilled methyl acrylate (0.224 mL, 0.214 g, 2.48 mmoles) was added and after stirring for 30 minutes the bath was removed and the reaction stirred for 14 h at RT. The volatiles were removed by vacuum transfer isolating the product as a slightly turbid slightly amber oil. Analysis of 5: ESI-MS (m/z): $[M+2H]^{2+}$ 1243, $[M+3H]^{3+}$ 829, $[M+4H]^{4+}$ 622.

Synthesis of 6: (where $R_1$ and $R_2$=H) To a 50 mL flask was added 5-aminoisophthalic acid (42.4 mg, 0.234 mmoles) followed by methanol (0.58 mL) and triethylamine (0.0718 mL, 52.1 mg, 0.515 mmoles) and the solution stirred for 5 minutes. Then the reaction flask was cooled in an ice bath and hexa-amine 4 (28.8 mg, 0.0224 moles) was added. After stirring for 15 minutes the reaction flask was heated in an oil bath at 40° C. for 4 h. A sample was removed for analysis.

Synthesis of 7: (where $R_1$ and $R_2$=H) To a 50 mL flask was added 4-amino-2,7-napthalenedisulfonic acid (78.7 mg, 0.259 mmoles) followed by methanol (1.40 mL) and triethylamine (0.0795 mL, 57.8 mg, 0.571 mmoles) and the solution stirred for 5 minutes. Then the reaction flask was cooled in an ice bath and hexa-amine 4 (34.2 mg, 0.0266 mmoles) was added. After stirring for 15 minutes the reaction flask was heated in an oil bath at 40° C. for 4 h. A sample was removed for analysis.

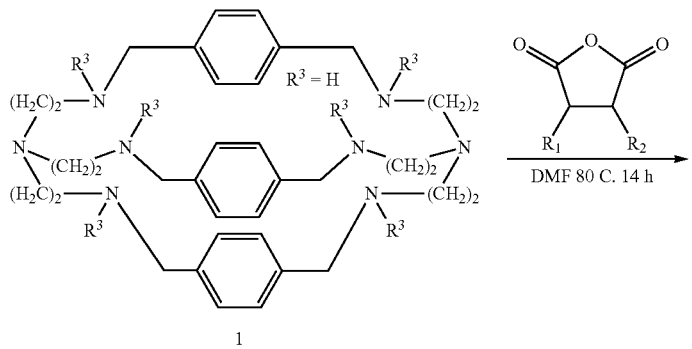

1

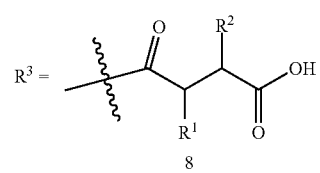

8

Where $R_1$ or $R_2$ are H or $CH_2CH\!=\!CH(CH_2)_5CH_3$

Synthesis of 8: (where $R_1$ or $R_2$=H or $CH_2CH$=$CH(CH_2)_5CH_3$ and $R_3$=Me) To a 50 mL RBF was added 1 (1.41 g, 2.35 mmoles) and nonenylsuccinic anhydride (3.07 mL, 3.16 g, 14.1 mmoles) followed by DMF (2.9 mL) and the solution heated on an oil bath at 80° C. for 14 h. Then the reaction solution was cooled to RT and volatiles were removed by vacuum transfer to a pressure of less than 20 mtorr.

General Experimental: All manipulations were carried out using Schlenk technique. Concentrated hydrochloric acid and acetic acid were purchased from J. T. Baker and used as received. Sodium hydroxide was purchased from Mallinckrodt and used as received. Sodium dicyanamide and sodium bicarbonate were purchased from Aldrich and used as received. Tris(2-aminoethyl)amine was purchased from Acros Organics and distilled before use. Terephthaldicarboxaldehyde and p-chloroaniline were purchased from Aldrich and sublimed before use. Sodium sulfate was purchased from EMD and used as received. Water was sparged for >10 minutes before use. Dichloromethane, ethyl acetate and hexanes were purchased from EMD and used as received. Ethyl alcohol, anhydrous 200 proof, was purchased from Aldrich and used as received. Silica gel 60 (230-400 mesh) was purchased from EMD and used as received. MS analysis was performed on an Applied Biosystems Voyager DE instrument at HT Laboratories in San Diego, Calif. NMR analysis was performed on a JEOL Eclipse+400 instrument at Acorn NMR, Inc. in Livermore, Calif.

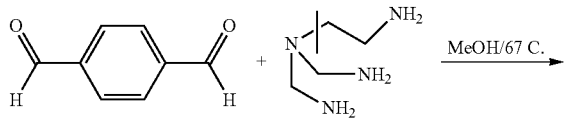

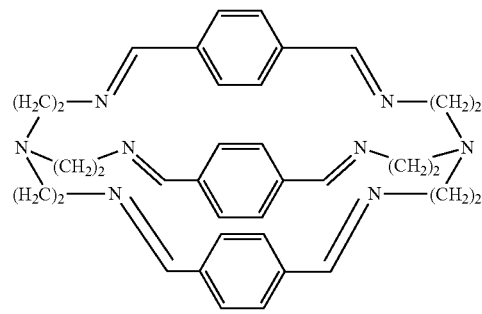

1

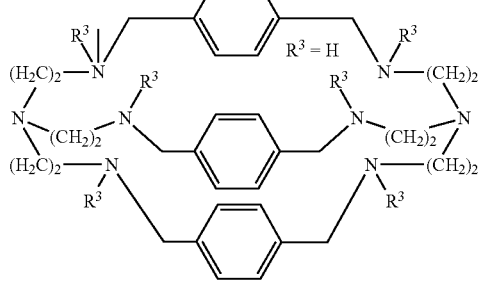

2

Synthesis of 2: To a 12 L round bottom flask equipped with a reflux condenser and addition funnel was added methanol (8 L) followed by terephthaldicarboxaldehyde (64.4 g, 0.480 moles). The solution was heated to 65° C. and tris(2-aminoethyl)amine (46.8 g, 47.9 mL, 0.320 moles) was added. Then the solution was refluxed for about 16 h and cooled to room temperature. The solution was filtered to another 12 L round bottom flask equipped with a reflux condenser and sodium borohydride (60.5 g, 1.60 moles) was added. The solution was refluxed for about 16 h and cooled to room temperature. The volatiles were removed by rotational evaporator and the residue dissolved in dichloromethane (720 mL) and hydrochloric acid, 1.0 M (3.2 L). It was stirred for 5 minutes. Then to the solution was added sodium hydroxide, 3.0 M (1.6 L), the solution stirred for 5 minutes and the phases separated. The aqueous was extracted with dichloromethane (2×400 mL, 2×200 mL), the organic phase combined, washed with water (2×600 mL) and dried over sodium sulfate. Then the volatiles were removed by vacuum transfer to leave a slightly off white powder (89.6 g, 150 mmoles, 93.5% yield). Analysis of 2: $^1$H NMR (400 MHz, $CD_2Cl_2$, δ): 2.61, 2.76 (m, 24H, $NCH_2CH_2NHCH_2C_6H_4$), 3.62 (s, 12H, $NCH_2CH_2NHCH_2C_6H_4$), 6.84 (s, 12H, $NCH_2CH_2NHCH_2C_6H_4$). ESI-MS (m/z): $[M+H]^+$ 599, $[M+H]^{2+}$ 300.

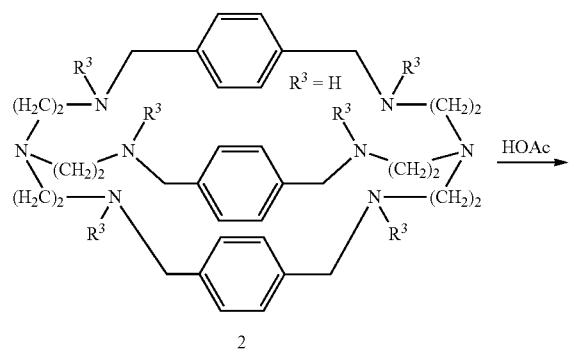

2

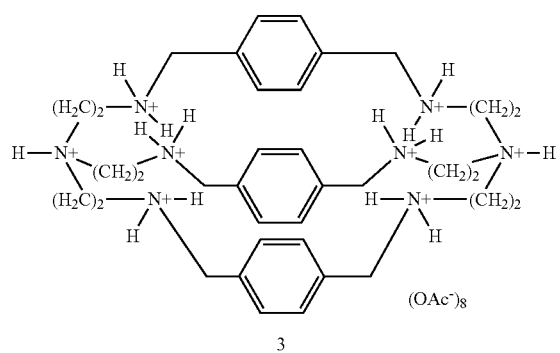

3

Synthesis of 3: Octa-amine 2 (19.9 g, 33.3 mmoles) was added to a 2 L flask and combined with ethyl acetate (924 mL) and acetic acid (38.1 mL, 40.0 g, 666 mmoles). The solution was filtered and hexanes (629 mL) was added which caused the product to crystallize. The solution was filtered and the precipitate washed with 80% hexanes, 20% ethyl acetate (1500 mL). The product was transferred to a flask and the volatiles removed by vacuum transfer. The supernatant was combined with hexanes (300 mL), filtered and washed with of 80% hexanes, 20% ethyl acetate (1500 mL). The precipitate was transferred to a flask and the volatiles removed by vacuum transfer. To the supernatant was added the wash solution from the second crop which precipitated the third crop of product. The solution was filtered and washed with 80% hexanes, 20% ethyl acetate (1500 mL). The precipitate was transferred to a flask and the volatiles removed by vacuum transfer. The product is a slightly off white powder (33.7 g, 31.3 mmoles, 93.9% yield). Analysis of 3: $^1$H NMR (400 MHz, Methanol-$d_4$, δ): 1.88 (s, 24H, $CH_3CO_2$), 2.78, 3.24 (m, 24H, $CH_2CH_2$), 4.14 (s, 12H, $NCH_2Ph$), 7.47 (s, 12H, Ph). MALDI-MS (m/z): $[M]^+$ 600, $[M+Na]^+$ 622.

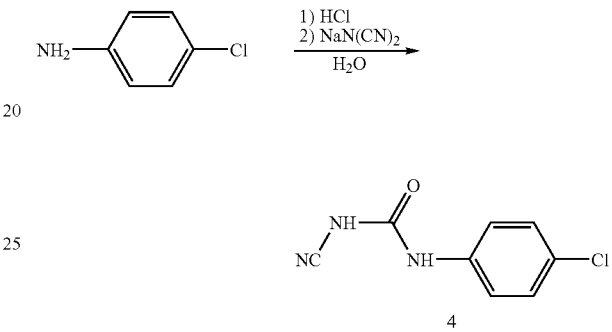

4

Synthesis of 4: The compound p-chloroaniline (170 g, 1.33 moles) was added to a 1 L flask and dissolved in water (625 mL) and concentrated HCl (111 mL, 1.33 moles). Then in a separate 5 L flask sodium dicyanamide (237 g, 2.66 moles) was dissolved in water (2035 mL) and heated to 50° C. The solution of p-chloroaniline was added to the solution of sodium dicyanamide over 120 minutes, the flask was fitted with a reflux condenser and then the reaction solution was heated for about 16 h at 90° C. Then the reaction solution was allowed to cool and saturated sodium bicarbonate (1500 mL) was added and the solution stirred for 15 minutes. Ethyl acetate (1000 mL) was added and the solution stirred for 10 minutes before the phases were separated. The aqueous phase was extracted with ethyl acetate (10×1000 mL, 500 mL), the organic extractions were combined and washed with saturated brine (3×1200 mL), dried over sodium sulfate (anhydrous) and filtered. A 10 cm deep silica plug was packed with silica/ethyl acetate slurry and then washed with ethyl acetate (2000 mL). The product was sent through the silica plug and the plug washed with ethyl acetate (6000 mL). The volatiles were removed from the filtrate by vacuum transfer until about 10% of the solution remained and the solution was filtered. The product was dried under vacuum to p<20 mtorr to leave a white powder. Then the product was placed under vacuum again at p<20 mtorr while on a 70° C. oil bath for 18 h (203 g, 1.04 moles, 78.3% yield). Analysis of 4: $^1$H NMR (400 MHz, DMSO-$d_6$, δ): 7.08 (s, 2H, PhNHC(NH)NHCN), 7.36 (m, 4H, Ph), 9.15 (s, 1H, PhNHC(Nh)NHCN). MALDI-MS (m/z): $[M]^+$ 195, $[M+Na]^+$ 218.

Synthesis of compound 4 has been described in patent GB599722 and J. Chem. Soc. 1946, p 729-737 and 1948, p 1630-1636, which are incorporated by reference as if fully set forth herein. Synthesis of compounds similar to compound 4 are described in U.S. Pat. Nos. 2,455,807 and 5,534,565, which are incorporated by reference as if fully set forth herein.

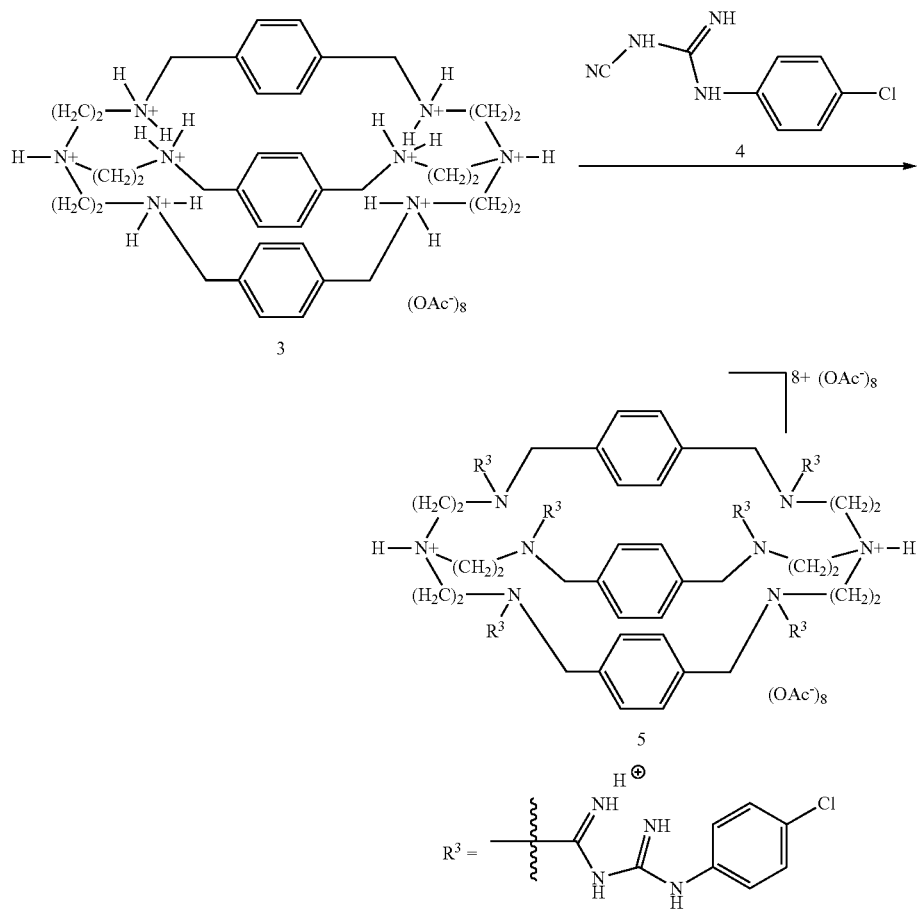

Synthesis of 5: Intermediate 3 (32.9 g, 30.5 mmoles) was added to a 500 mL flask followed by 1-butanol (30.3 mL) which formed a slurry. Then 4 (39.1 g, 201 mmoles) was added. The flask was fitted with a reflux condenser and placed into an oil bath set to reach 90° C. It was heated for 3 days and allowed to cool to room temperature. The volatiles were removed by vacuum transfer and the resulting foam was crushed to a powder. The crude product was dissolved in ethyl alcohol (31.9 mL) and ethyl acetate (65.4 mL). The product was precipitated with ethyl acetate (915 mL) and the solution filtered. Then the product was washed with ethyl acetate (980 mL) and the volatiles removed by vacuum transfer to produce a white powder (57.9 g, 25.8 mmoles, 84.5% yield). Analysis of 5: MALDI-MS (m/z): 1269 [M+5 DHB]$^{2+}$, 1423 [M+7 DHB]$^{2+}$ (DHB is MALDI matrix dihydroxybenzoic acid).

The product 5 can be converted to the freebase and then protonated with mineral, organic or other acids to afford the desired counter ion (anion) (for example 5 can be treated with base, isolated as the freebase and treated with acetic acid to regenerate 5, i.e. replace acetic acid with a different acid such as D-Gluconic Acid, Butyric Acid, Nalidixic Acid, Statin Acids (e.g., pravastatin, fluvastatin, atorvastatin, etc.), Nicotinic Acid (i.e. Niacin), Enrofloxacin (or combination of acids) to generate the salt containing the desired anion counter-ion and/or mixture). Analysis of Freebase of 5: MALDI-MS (m/z): 883 [M]$^{2+}$ Combining of the Freebase of 5 and Nicotinic Acid To a vial and stirbar, (0.038 mg, 0.0215=mol) of the freebase of 5 was added followed by 0.76 mL of deionized water, 0.620 of ethyl alcohol and 8 equiv. (0.017 g, 0.14 mmol) of Nicotinic acid (also known as Niacin or vitamin B$_3$). The mixture was stirred for about 1 h resulting in a clear homogeneous solution. MALDI-MS (m/z): 1379 [M]$^{2+}$ [M]$^{2+}$ −1 Nicotinic Acid 1314; [M]$^{2+}$ −2 Nicotinic Acid 1253

Combining of the Freebase of 5 and Nalidixic Acid

To a vial and stirbar, (0.026 mg, 0.015 mmol) of the freebase of 5 was added followed by 2.0 mL of acetone, 1.0 mL of deionized water and 8 equiv. (0.028 g, 0.12 mmol) of Nalidixic acid. The mixture was stirred for about 1 h to form a clear homogeneous solution. MALDI-MS (m/z): 1210 [M]$^{3+}$ [M]$^{2+}$ −1 Nalidixic Acid 1697; [M]$^{2+}$ −2 Nalidixic Acid 1580.

Combining of the Freebase of 5 and Butyric Acid

To a vial and stirbar, (0.027 mg, 0.015 mmol) of the freebase of 5 was added followed by 2.0 mL of acetone, 1.0 mL of deionized water and 8 equiv. (0.011 mL, 0.12 mmol) of Butyric acid. The mixture was stirred for about 1 h to form a clear homogeneous solution.

Combining of the Freebase of 5 and Enrofloxacin

To a vial and stirbar, (0.027 mg, 0.015 mmol) of the freebase of 5 was added followed by 2.0 mL of acetone and 1.0 mL of deionized water and 8 equiv. (0.027 mg, 0.015 mmol) of Enrofloxacin. The mixture was stirred for about 1 h to form a clear homogeneous solution.

Example of an Otic Composition Formulation with Glycerol

To a vial and stirbar, (0.050 g, 0.022 mmol) 5 was added followed by 0.95 g of glycerol. The mixture was stirred and heated to 40° C. for 5 min. resulting in a clear homogeneous solution.

Example of an Otic Composition Formulation with Water

To a vial and stirbar, (0.050 g, 0.022 mmol) 5 was added followed by 0.95 g of deionized water. The mixture was stirred at room temperature and/or optionally heated to 40° C. for 5 min. resulting in a clear homogeneous solution.

Formulation of Dental Sealant Varnish

General: Poly(vinyl acetate-co-crotonic acid) beads and ethyl alcohol (anhydrous 200 proof) were purchased from Aldrich and used without further purification.

Example: Poly(vinyl acetate-co-crotonic acid) (0.80 g) was dissolved in water (1.74 mL) and ethyl alcohol (7.81 mL). The active ingredient 5 (0.50 g) was dissolved in ethyl alcohol (1.00 mL). The two solutions were combined and mixed for 2 hours.

Other common dental formulation or coating formulation components known by those skilled in the art may be used in conjunction with or in place of the above example In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A chemical compound, wherein the chemical compound comprises a structure (Ia):

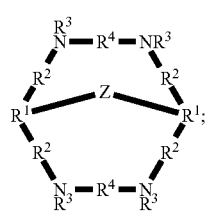

(Ia)

wherein each $R^1$ is independently N, $N^+H$, or $N^+R^3$;

wherein each $R^2$ is independently an alkyl group, or a substituted alkyl group;

wherein each $R^3$ is independently a hydrogen, a pharmaceutically active agent, an alkyl-aryl group, a substituted alkyl-aryl group, an alkyl group, a substituted alkyl group, an aryl group, a substituted aryl group, a heterocycle group, a substituted heterocycle group, an alkene, an ether, a hydrophilic group, a polyethyleneglycol, a polyethyleneimine, or any combination of these;

wherein each $R^4$ is independently an aryl group or a substituted aryl group, wherein when $R^4$ is an aryl group the aryl group is a phenyl, a naphthyl, a biphenyl, a diphenylmethyl, or a benzophenone, and wherein when $R^4$ is a substituted aryl group the substituted aryl group is a phenyl having at least one substituent, a naphthyl having at least one substituent, a biphenyl having at least one substituent, a diphenylmethyl having at least one substituent, or a benzophenone having at least one substituent;

wherein Z comprises at least one bridge, wherein at least one of the bridges comprises —$R^2$—$NR^3$—$R^4$—$NR^3$—$R^2$—, and wherein each bridge independently couples $R^1$ to $R^1$;

wherein each of the heterocycle groups independently comprises a 5-7-membered monocyclic ring or a 7-10-membered bicyclic heterocyclic ring, and wherein the heterocycle group comprises carbon atoms and 1-4 heteroatoms;

wherein each of the substituted alkyl groups independently comprises at least one substituent and wherein each substituent is independently an aryl, an acyl, an alkyl, a halogen, an alkylhalo, a hydroxy, an amino, an alkoxy, an alkylamino, an acylamino, an acyloxy, an aryloxy, an aryloxyalkyl, a mercapto, a saturated cyclic hydrocarbon, an unsaturated cyclic hydrocarbon, and/or a heterocycle;

wherein each of the substituted heterocycle groups independently comprises at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;

wherein each of the hydrophilic groups independently comprises a hydroxyl, a methoxy, a carboxylic acid, an ester of a carboxylic acid, an amide, an amino, a cyano, an isocyano, an ammonium salt, a sulfonium salts, a phosphonium salt, a mono-alkyl substituted amino groups, a di-alkyl substituted amino group, a polypropyleneglycol, a polyethylene glycol, an epoxy group, an acrylate, a sulfonamide, a nitro, a —OP(O)(OCH$_2$CH$_2$N$^+$R$^3$R$^3$R$^3$)O$^-$, a guanidinium, an aminate, an acrylamide, a pyridinium, a piperidine, a polymethylene chains substituted with an alcohol, a carboxylate, an acrylate, or a methacrylate, an alkyl chain having internal amino or substituted amino groups comprising internal —NH—, —NC(O)R$^3$—, or —NC(O)CH=CH$_2$— groups, a polycaprolactone, a polycaprolactone diol, a poly(acetic acid), a poly(vinyl acetate), a poly(2-vinyl pyridine), a cellulose ester, a cellulose hydroxylether, a poly(L-lysine hydrobromide), a poly(itaconic acid), a poly(maleic acid), a poly(styrenesulfonic acid), a poly(aniline), or a poly(vinyl phosphonic acid); and at least two pharmaceutically active agents per chemical compound, wherein at least one of the pharmaceutically active agents is configured to inhibit and/or ameliorate at least one malady, wherein at least one of the pharmaceutically active agents is covalently bound to the chemical compound or is a counter ion to a salt of the chemical compound, and wherein at least one of the pharmaceutically active agents comprises a statin, a quinolone, a doxorubicin hydrochloride, a guanidine moiety, a butyrate, a butyric acid, a polymeric acid, a quaternary ammonium moiety, an alkyl sulfonic acid, an aryl sulfonic acid, a nicotinic acid,

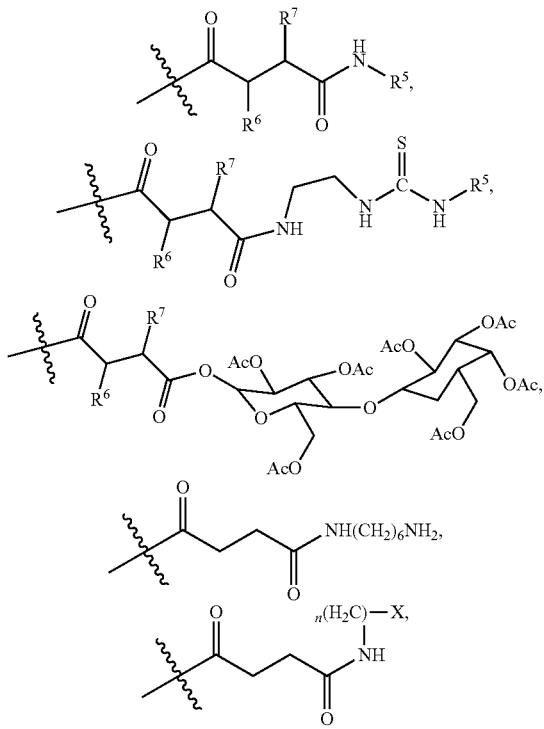

or derivatives thereof, wherein at least one of the —$R^5{}_S$ comprises

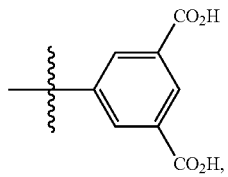

or a salt thereof, wherein each $R^6$ is independently a hydrogen, an alkyl group, or an aryl group, wherein each $R^7$ is independently a hydrogen, an alkyl group, or an aryl group, wherein n is 0 to 12, and wherein X comprises a sugar, a carbohydrate, or a salt thereof.

2. The chemical compound of claim 1, wherein the chemical compound is part of a chemical composition, wherein the chemical composition further comprises one or more polymerizable compounds, and wherein the chemical composition is configured such that, when the chemical composition is applied to a surface and cured, then at least a portion of the chemical composition forms an antimicrobial coating over at least a portion of the surface.

3. The chemical compound of claim 1, wherein the chemical compound is a salt of the chemical compound.

4. The chemical compound of claim 1, wherein the chemical compound is part of a chemical composition, and wherein the chemical composition further comprises a polymer or a prepolymer.

5. The chemical compound of claim 1, wherein the chemical compound is part of a chemical composition, wherein the chemical composition further comprises a polymer or a prepolymer, and wherein at least one polymer is a poly(vinyl acetate-co-crotonic acid).

6. The chemical compound of claim 1, wherein the chemical compound comprises a structure:

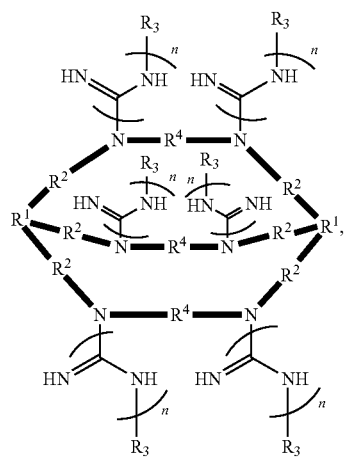

wherein n ranges from 1 to 2.

7. The chemical compound of claim 1, wherein the chemical compound comprises a structure:

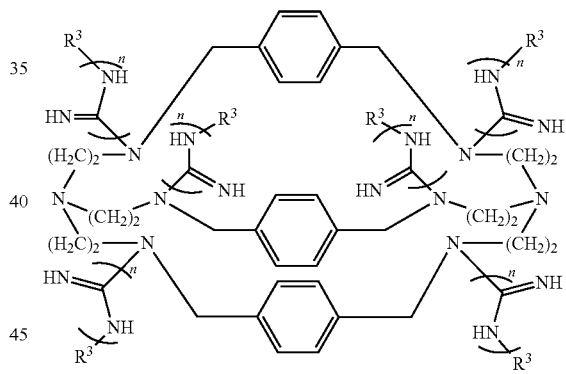

wherein n ranges from 1 to 2.

8. The chemical compound of claim 1, wherein the chemical compound comprises a structure:

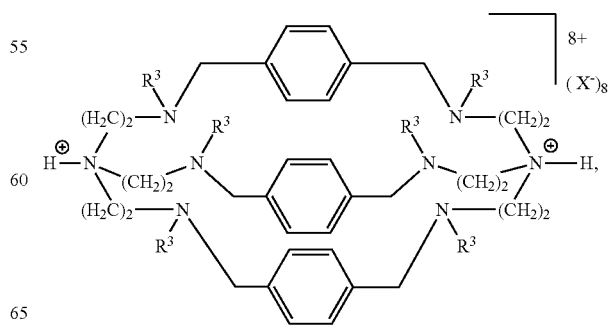

wherein X is a counter ion, and wherein R³ is

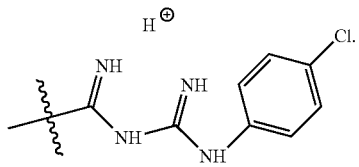

9. The chemical compound of claim 1, wherein at least one R³ comprises a guanidine moiety and a halogenated aryl moiety.

10. The chemical compound of claim 1, wherein at least one R³ comprises at least one phenol moiety.

11. The chemical compound of claim 1, wherein at least one of the pharmaceutically active agents is an antiviral agent.

12. The chemical compound of claim 1, wherein at least one of the pharmaceutically active agents is an anticancer agent.

13. The chemical compound of claim 1, wherein at least one of the pharmaceutically active agents is an anti-inflammatory agent.

14. The chemical compound of claim 1, wherein at least one of the pharmaceutically active agents is an antimicrobial agent.

15. The chemical compound of claim 1, wherein at least one of the pharmaceutically active agents is a lipase inhibitor.

16. The chemical compound of claim 1, wherein at least one of the pharmaceutically active agents is a bile acid sequestrant.

17. The chemical compound of claim 1, wherein at least one of the pharmaceutically active agents is a cholesterol reduction agent.

18. The chemical compound of claim 1, wherein at least one of the pharmaceutically active agents comprises a statin.

19. The chemical compound of claim 1, wherein at least one of the pharmaceutically active agents is configured to inhibit and/or ameliorate otic maladies.

20. The chemical compound of claim 1, wherein at least one of the pharmaceutically active agents is configured to inhibit and/or ameliorate renal maladies.

21. The chemical compound of claim 1, wherein at least one of the pharmaceutically active agents is configured to inhibit and/or ameliorate renal maladies by binding phosphates.

22. The chemical compound of claim 1, wherein at least one of the pharmaceutically active agents is configured to bind salts.

23. The chemical compound of claim 1, wherein at least one of the pharmaceutically active agents is configured to bind metals and/or metal ions.

24. The chemical compound of claim 1, wherein at least one of the pharmaceutically active agents is configured to bind water.

25. The chemical compound of claim 1, further comprising a polymeric acid.

26. The chemical compound of claim 1, wherein at least one of the pharmaceutically active agents is configured to regulate fat absorption.

27. The chemical compound of claim 1, wherein at least one of the pharmaceutically active agents is a periodontal disease agent.

28. The chemical compound of claim 1, wherein at least one of the pharmaceutically active agents is a periodontal stomatitis inhibitor.

29. The chemical compound of claim 1, wherein at least one of the pharmaceutically active agents is an oral cavity disease Feline Odontoclastic Resorptive Lesions inhibitor.

30. A method of inhibiting or ameliorating a malady comprising:
administering to a subject an effective amount of
a chemical compound, wherein the chemical compound comprises a structure (Ia):

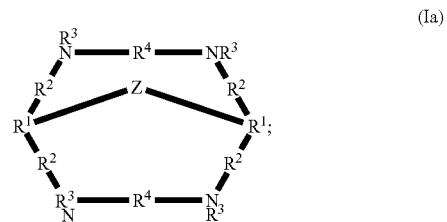

wherein each $R^1$ is independently N, $N^+H$, or $N^+R^3$;

wherein each $R^2$ is independently an alkyl group, or a substituted alkyl group;

wherein each $R^3$ is independently a hydrogen, a pharmaceutically active agent, an alkyl-aryl group, a substituted alkyl-aryl group, an alkyl group, a substituted alkyl group, an aryl group, a substituted aryl group, a heterocycle group, a substituted heterocycle group, an alkene, 1 an ether, a hydrophilic group, a polyethyleneglycol, a polyethyleneimine, or any combination of these;

wherein each $R^4$ is independently an aryl group or a substituted aryl group, wherein when $R^4$ is an aryl group the aryl group is a phenyl, a naphthyl, a biphenyl, a diphenylmethyl, or a benzophenone, and wherein when $R^4$ is a substituted aryl group the substituted aryl group is a phenyl having at least one substituent, a naphthyl having at least one substituent, a biphenyl having at least one substituent, a diphenylmethyl having at least one substituent, or a benzophenone having at least one substituent;

wherein Z comprises at least one bridge, wherein at least one of the bridges comprises —$R^2$—$NR^3$—$R^4$—$NR^3$—$R^2$—, and wherein each bridge independently couples $R^1$ to $R^1$;

wherein each of the heterocycle groups independently comprises a 5-7-membered monocyclic ring or a 7-10-membered bicyclic heterocyclic ring, and wherein the heterocycle group comprises carbon atoms and 1-4 heteroatoms;

wherein each of the substituted alkyl groups independently comprises at least one substituent and wherein each substituent is independently an aryl, an acyl, an alkyl, a halogen, an alkylhalo, a hydroxy, an amino, an alkoxy, an alkylamino, an acylamino, an acyloxy, an aryloxy, an aryloxyalkyl, a mercapto, a saturated cyclic hydrocarbon, an unsaturated cyclic hydrocarbon, and/or a heterocycle;

wherein each of the substituted heterocycle groups independently comprises at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;

wherein each of the hydrophilic groups independently comprises a hydroxyl, a methoxy, a carboxylic acid, an ester of a carboxylic acid, an amide, an amino, a cyano, an isocyano, an ammonium salt, a sulfonium salts, a phosphonium salt, a mono-alkyl substituted amino groups, a di-alkyl substituted amino group, a polypropyleneglycol, a polyethylene glycol, an epoxy group, an acrylate, a sulfonamide, a nitro, a $OP(O)(OCH_2CH_2N^+R^3R^3R^3)O^-$, a guanidinium, an aminate, an acrylamide, a pyridinium, a piperidine, a polymethylene chains substituted with an alcohol, a carboxylate, an acrylate, or a methacrylate, an alkyl chain having internal amino or substituted amino groups comprising internal —NH—, —NC(O)$R^3$—, or —NC(O)CH=CH$_2$— groups, a polycaprolactone, a polycaprolactone diol, a poly(acetic acid), a poly(vinyl acetate), a poly(2-vinyl pyridine), a cellulose ester, a cellulose hydroxylether, a poly(L-lysine hydrobromide), a poly(itaconic acid), a poly(maleic acid), a poly(styrenesulfonic acid), a poly(aniline), or a poly(vinyl phosphonic acid); and;

at least two pharmaceutically active agents per chemical compound, wherein at least two of the pharmaceutically active agents are covalently bound to chemical compound or are a counter ion to a salt of the chemical compound, and wherein at least one of the pharmaceutically active agents comprises a statin, a quinolone, a doxorubicin hydrochloride, a guanidine moiety, a butyrate, a butyric acid, a polymeric acid, a quaternary ammonium moiety, an alkyl sulfonic acid, an aryl sulfonic acid, a nicotinic acid,

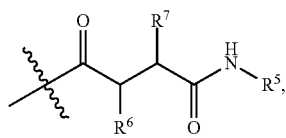

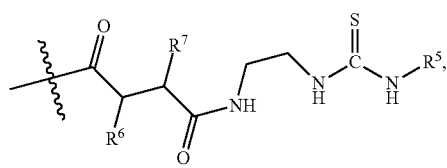

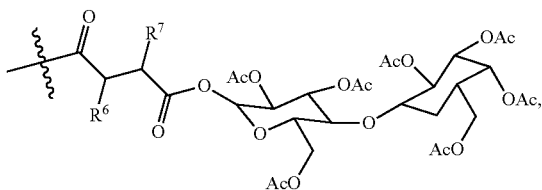

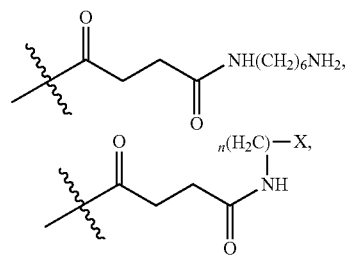

or derivatives thereof, wherein at least one of the —$R^5$s comprises

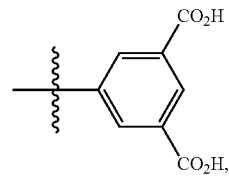

or a salt thereof, wherein each $R^6$ is independently a hydrogen, an alkyl group, or an aryl group, wherein each $R^7$ is independently a hydrogen, an alkyl group, or an aryl group, wherein n is 0 to 12, and wherein X comprises a sugar, a carbohydrate, or a salt thereof; and inhibiting or ameliorating a malady with the chemical compound wherein at least one of the maladies is an infection, a wound, a parasite, a virus, an inflammation, a renal disease, a periodontal disease, Feline Odontoclastic Resorptive Lesions, fat absorption, ovarian cancer, breast cancer, prostate cancer, or metal poisoning.

31. The chemical compound of claim 1, wherein at least one of the pharmaceutically active agents comprises a quinolone, and wherein the quinoline comprises a quinolonecarboxylic acid or a derivative thereof.

32. The chemical compound of claim 1, wherein at least one of the pharmaceutically active agents comprises a quinolone, and wherein the quinoline comprises a nalidixic acid or a derivative thereof.

33. The chemical compound of claim 1, wherein at least one of the pharmaceutically active agents comprises a quinolone, and wherein the quinoline comprises an enrofloxacin or a derivative thereof.

34. The chemical compound of claim 1, wherein at least one of the pharmaceutically active agents comprises a polymeric acid, and wherein the polymeric acid comprises a polyethyleneglycol acid.

35. The chemical compound of claim 1, further comprising Methoxypolyethylene glycol 5,000 acetic acid and/or Methoxypolyethylene glycol 5,000 propionic acid.

36. The chemical compound of claim 1, wherein at least one of the pharmaceutically active agents comprises a statin, and wherein the statin comprises an atorvastatin, a cerivastatin, an ezetimibe, a fluvastatin, a lovastatin, a mevastatin, a niacin, a pitavastatin, a pravastatin, a rosuvastatin, a simvastatin, or derivatives thereof.

37. The chemical compound of claim 1, wherein at least one of the pharmaceutically active agents comprises D-Gluconic Acid, Butyric Acid, Nalidixic Acid, Nicotinic Acid, Enrofloxacin, or derivatives thereof.

38. The chemical compound of claim 1, wherein at least one of the pharmaceutically active agents comprises a guanidine moiety, a quaternary ammonium moiety, or derivatives thereof.

39. The chemical compound of claim 1, wherein at least one of the pharmaceutically active agents comprises

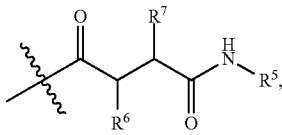

107

-continued

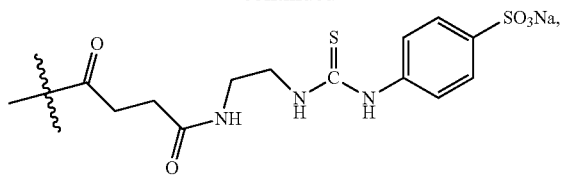

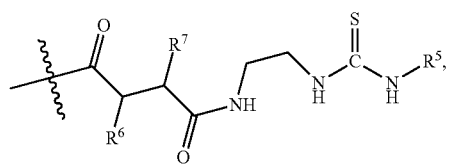

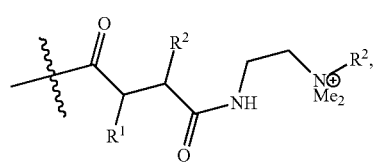

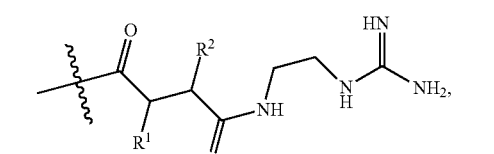

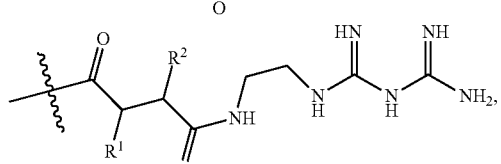

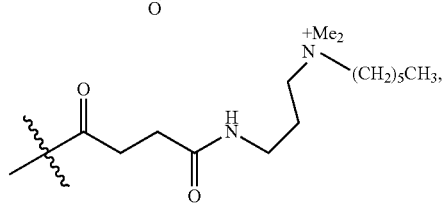

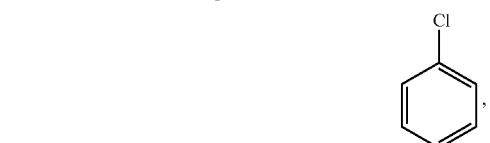

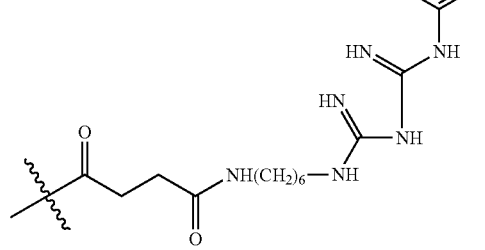

or derivatives thereof, wherein at least one of the $R^5$s comprises

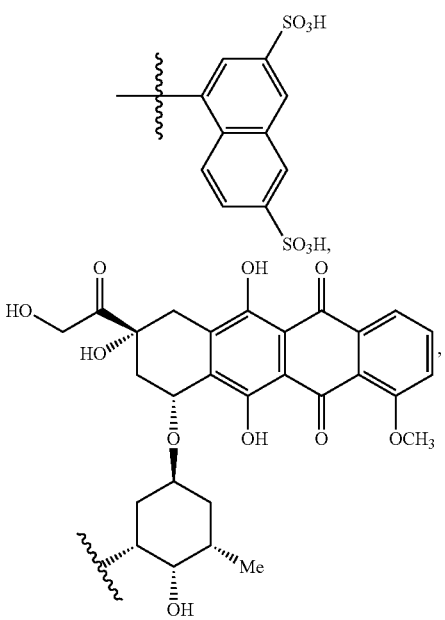

or a salt thereof.

40. The chemical compound of claim 1, wherein the chemical compound is part of a chemical composition, wherein the chemical composition further comprises at least one pharmaceutically active agent.

41. The chemical compound of claim 1, wherein the chemical compound is part of a chemical composition, wherein the chemical composition further comprises glycerol or propylene glycol.

42. A chemical composition comprising:
at least one polymer or at least one prepolymer; and
a chemical compound, wherein the chemical compound comprises a structure (Ia):

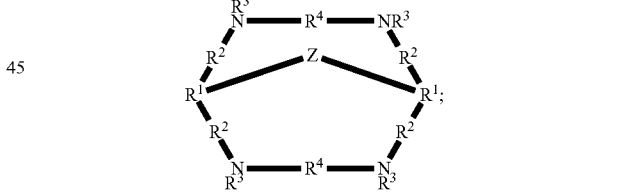

(Ia)

wherein each $R^1$ is independently N, $N^+H$, or $N^+R^3$;
wherein each $R^2$ is independently an alkyl group, or a substituted alkyl group;
wherein each $R^3$ is independently a hydrogen, a pharmaceutically active agent, an alkyl-aryl group, a substituted alkyl-aryl group, an alkyl group, a substituted alkyl group, an aryl group, a substituted aryl group, a heterocycle group, a substituted heterocycle group, an alkene, an ether, a hydrophilic group, a polyethyleneglycol, a polyethyleneimine, or any combination of these;
wherein each $R^4$ is independently an aryl group or a substituted aryl group, wherein when $R^4$ is an aryl group the aryl group is a phenyl, a naphthyl, a biphenyl, a diphenylmethyl, or a benzophenone, and wherein when $R^4$ is a substituted aryl group the substituted aryl group is a phenyl having at least one substituent, a naphthyl having at least one substituent, a biphenyl having at least one substituent, a diphenylmethyl having at least one substituent, or a benzophenone having at least one substituent;

wherein Z comprises at least one bridge, wherein at least one of the bridges comprises —$R^2$—$NR^3$—$R^4$—$NR^3$—$R^2$—, and wherein each bridge independently couples $R^1$ to $R^1$;

wherein each of the heterocycle groups independently comprises a 5-7-membered monocyclic ring or a 7-10-membered bicyclic heterocyclic ring, and wherein the heterocycle group comprises carbon atoms and 1-4 heteroatoms;

wherein each of the substituted alkyl groups independently comprises at least one substituent and wherein each substituent is independently an aryl, an acyl, an alkyl, a halogen, an alkylhalo, a hydroxy, an amino, an alkoxy, an alkylamino, an acylamino, an acyloxy, an aryloxy, an aryloxyalkyl, a mercapto, a saturated cyclic hydrocarbon, an unsaturated cyclic hydrocarbon, and/or a heterocycle;

wherein each of the substituted heterocycle groups independently comprises at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;

wherein each of the hydrophilic groups independently comprises a hydroxyl, a methoxy, a carboxylic acid, an ester of a carboxylic acid, an amide, an amino, a cyano, an isocyano, an ammonium salt, a sulfonium salts, a phosphonium salt, a mono-alkyl substituted amino groups, a di-alkyl substituted amino group, a polypropyleneglycol, a polyethylene glycol, an epoxy group, an acrylate, a sulfonamide, a nitro, a —OP(O)($OCH_2CH_2N^+R^3R^3R^3$)$O^-$, a guanidinium, an aminate, an acrylamide, a pyridinium, a piperidine, a polymethylene chains substituted with an alcohol, a carboxylate, an acrylate, or a methacrylate, an alkyl chain having internal amino or substituted amino groups comprising internal —NH—, —NC(O)$R^3$—, or —NC(O)CH═$CH_2$— groups, a polycaprolactone, a polycaprolactone diol, a poly(acetic acid), a poly(vinyl acetate), a poly(2-vinyl pyridine), a cellulose ester, a cellulose hydroxylether, a poly(L-lysine hydrobromide), a poly(itaconic acid), a poly(maleic acid), a poly(styrenesulfonic acid), a poly(aniline), or a poly(vinyl phosphonic acid); and at least two pharmaceutically active agents per chemical compound, wherein at least one of the pharmaceutically active agents is configured to inhibit and/or ameliorate at least one malady, wherein at least one of the pharmaceutically active agents is covalently bound to the chemical compound or is a counter ion to a salt of the chemical compound, and wherein at least one of the pharmaceutically active agents comprises a statin, a quinolone, a doxorubicin hydrochloride, a guanidine moiety, a butyrate, a butyric acid, a polymeric acid, a quaternary ammonium moiety, an alkyl sulfonic acid, an aryl sulfonic acid, a nicotinic acid,

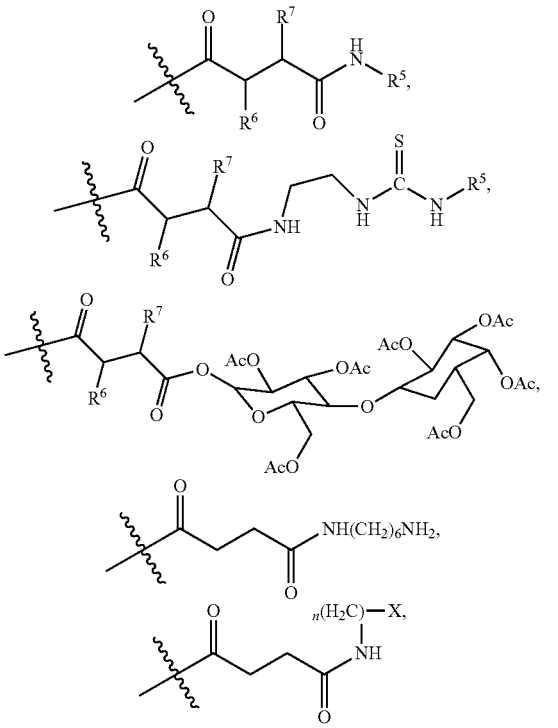

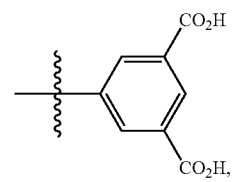

or derivatives thereof, wherein at least one of the $R^5$s comprises

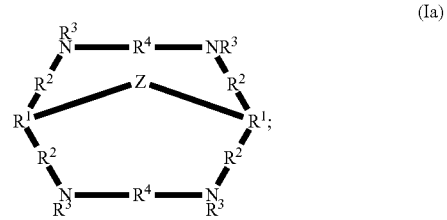

or a salt thereof, wherein each $R^6$ is independently a hydrogen, an alkyl group, or an aryl group, wherein each $R^7$ is independently a hydrogen, an alkyl group, or an aryl group, wherein n is 0 to 12, and wherein X comprises a sugar, a carbohydrate, or a salt thereof.

43. A chemical composition comprising:
at least one alcohol; and
a chemical compound, wherein the chemical compound comprises a structure (Ia):

(Ia)

wherein each $R^1$ is independently N, $N^+H$, or $N^+R^3$;
wherein each $R^2$ is independently an alkyl group, or a substituted alkyl group;
wherein each $R^3$ is independently a hydrogen, a pharmaceutically active agent, an alkyl-aryl group, a substituted alkyl-aryl group, an alkyl group, a substituted alkyl group, an aryl group, a substituted aryl group, a heterocycle group, a substituted heterocycle group, an alkene, an ether, a hydrophilic group, a polyethyleneglycol, a polyethyleneimine, or any combination of these;

wherein each $R^4$ is independently an aryl group or a substituted aryl group, wherein when $R^4$ is an aryl group the aryl group is a phenyl, a naphthyl, a biphenyl, a diphenylmethyl, or a benzophenone, and wherein when $R^4$ is a substituted aryl group the substituted aryl group is a phenyl having at least one substituent, a naphthyl having at least one substituent, a biphenyl having at least one substituent, a diphenylmethyl having at least one substituent, or a benzophenone having at least one substituent;

wherein Z comprises at least one bridge, wherein at least one of the bridges comprises —$R^2$—$NR^3$—$R^4$—$NR^3$—$R^2$—, and wherein each bridge independently couples $R^1$ to $R^1$;

wherein each of the heterocycle groups independently comprises a 5-7-membered monocyclic ring or a 7-10-membered bicyclic heterocyclic ring, and wherein the heterocycle group comprises carbon atoms and 1-4 heteroatoms;

wherein each of the substituted alkyl groups independently comprises at least one substituent and wherein each substituent is independently an aryl, an acyl, an alkyl, a halogen, an alkylhalo, a hydroxy, an amino, an alkoxy, an alkylamino, an acylamino, an acyloxy, an aryloxy, an aryloxyalkyl, a mercapto, a saturated cyclic hydrocarbon, an unsaturated cyclic hydrocarbon, and/or a heterocycle;

wherein each of the substituted heterocycle groups independently comprises at least one substituent and wherein each substituent is independently an alkyl, an aryl, an acyl, a halogen, an alkylhalo, a hydroxy, an amino, an alkoxy, an alkylamino, an acylamino, an acyloxy, an aryloxy, an aryloxyalkyl, a thioether, a heterocycle, a saturated cyclic hydrocarbon, and/or an unsaturated cyclic hydrocarbon;

wherein each of the hydrophilic groups independently comprises a hydroxyl, a methoxy, a carboxylic acid, an ester of a carboxylic acid, an amide, an amino, a cyano, an isocyano, an ammonium salt, a sulfonium salts, a phosphonium salt, a mono-alkyl substituted amino groups, a di-alkyl substituted amino group, a polypropyleneglycol, a polyethylene glycol, an epoxy group, an acrylate, a sulfonamide, a nitro, a —OP(O) (OCH$_2$CH$_2$N$^+$R$^3$R$^3$R$^3$)O$^-$, a guanidinium, an aminate, an acrylamide, a pyridinium, a piperidine, a polymethylene chains substituted with an alcohol, a carboxylate, an acrylate, or a methacrylate, an alkyl chain having internal amino or substituted amino groups comprising internal —NH—, —NC(O)R$^3$—, or —NC(O)CH═CH$_2$— groups, a polycaprolactone, a polycaprolactone diol, a poly(acetic acid), a poly(vinyl acetate), a poly(2-vinyl pyridine), a cellulose ester, a cellulose hydroxylether, a poly(L-lysine hydrobromide), a poly(itaconic acid), a poly(maleic acid), a poly(styrenesulfonic acid), a poly(aniline), or a poly(vinyl phosphonic acid); and at least two pharmaceutically active agents per chemical compound, wherein at least one of the pharmaceutically active agents is configured to inhibit and/or ameliorate at least one malady, wherein at least one of the pharmaceutically active agents is covalently bound to the chemical compound or is a counter ion to a salt of the chemical compound, and wherein at least one of the pharmaceutically active agents comprises a statin, a quinolone, a doxorubicin hydrochloride, a guanidine moiety, a butyrate, a butyric acid, a polymeric acid, a quaternary ammonium moiety, an alkyl sulfonic acid, an aryl sulfonic acid, a nicotinic acid,

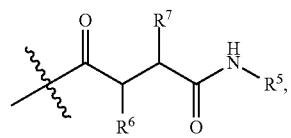

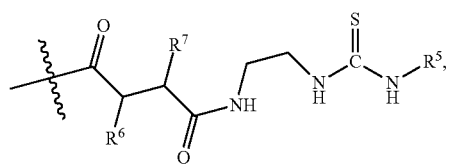

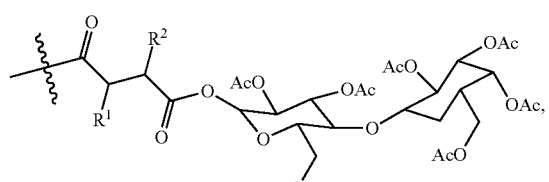

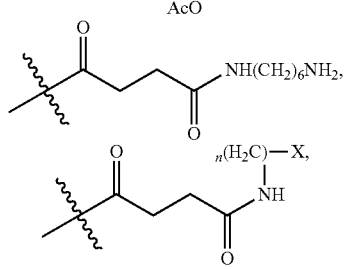

or derivatives thereof, wherein at least one of the $R^5$s comprises

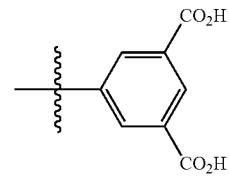

or a salt thereof, wherein each $R^6$ is independently a hydrogen, an alkyl group, or an aryl group, wherein each $R^7$ is independently a hydrogen, an alkyl group, or an aryl group, wherein n is 0 to 12, and wherein X comprises a sugar, a carbohydrate, or a salt thereof.

44. The chemical composition of claim 43, wherein at least one of the alcohols comprises glycerol or propylene glycol.

45. The chemical compound of claim 1, wherein at least one of the pharmaceutically active agents comprises

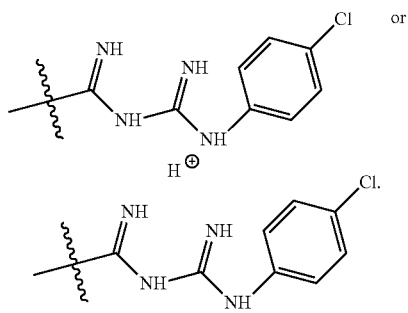

46. The chemical compound of claim 1, wherein each of the aryl groups independently comprises a phenyl, a naphthyl, a biphenyl, a diphenylmethyl, or a benzophenone.

47. The chemical compound of claim 1, wherein each of the substituted aryl groups independently comprises a phenyl having at least one substituent, a naphthyl having at least one substituent, a biphenyl having at least one substituent, a diphenylmethyl having at least one substituent, or a benzophenone having at least one substituent.

* * * * *